United States Patent
Logan (12)

(10) Patent No.: US 7,157,240 B2
(45) Date of Patent: Jan. 2, 2007

(54) MID 4460, A HUMAN TYROSINE PHOSPHATASE FAMILY MEMBER AND USES THEREFOR

(75) Inventor: Thomas Joseph Logan, Needham, MA (US)

(73) Assignee: Bayer Healthcare AG, Leverkusen (DE)

( * ) Notice: Subject to any disclaimer, the term of this patent is extended or adjusted under 35 U.S.C. 154(b) by 591 days.

(21) Appl. No.: 10/245,539

(22) Filed: Sep. 17, 2002

(65) Prior Publication Data

US 2003/0077638 A1 Apr. 24, 2003

Related U.S. Application Data

(60) Provisional application No. 60/323,018, filed on Sep. 18, 2001.

(51) Int. Cl.
*C12Q 1/42* (2006.01)

(52) U.S. Cl. ............ 435/21; 435/194; 435/252.3; 435/252.33; 435/320.1; 435/69.2; 536/23.2

(58) Field of Classification Search .......... 435/21, 435/196, 252.3, 320.1; 536/23.2
See application file for complete search history.

(56) References Cited

U.S. PATENT DOCUMENTS 6,436,685 B1 * 8/2002 Acton .................. 435/196
6,607,879 B1   8/2003 Cocks et al. ............. 435/6

FOREIGN PATENT DOCUMENTS

WO   WO 00/75339 A1   12/2000
WO   WO 01/61031 A2    8/2001
WO   WO 01/94629 A2   12/2001

OTHER PUBLICATIONS

Matozaki et al. [J. Biol. Chem. 269 (3): 2075-2081 (1994)].*

Sequence alignment between Accession No. A49724 and Applicants' SEQ ID Nos. 2 showing 100% identity.*

Sequence alignment between Accession No. D15049 and Applicants' SEQ ID Nos. 1 showing 100% identity.*

Takashi Matozaki, et al., "Molecular Cloning of a Human Transmembrane-Type Protein Tyrosine Phosphatase and Its Expression in Gastrointestinal Cancers," Journal of Biological Chemistry, 269(3); 2075-2081, 1994.

Strausberg, R., Sep. 12, 1997 (sequence) GenBank [online] Bethesda, MD, USA: National Center for Biotechnology Information [retrieved Aug. 19, 2003]. Retrieved from the Internet URL: http://www.ncbi.nlm.nih.gov/>. GenBank Accession No. AA573849.

Strausberg, R., Jul. 13, 2000 (sequence) GenBank [online] Bethesda, MD, USA: National Center for Biotechnology Information [retrieved Aug. 19, 2003]. Retrieved from the Internet URL: http://www.ncbi.nlm.nih.gov/>. GenBank Accession No. BE304621.

Myers, R. M., "Human STS SHGC-10956, Sequence Tagged Site", Jan. 4, 1996 (sequence) GenBank [online] Bethesda, MD, USA: National Center for Biotechnology Information [retrieved Aug. 19, 2003]. Retrieved from the Internet URL: http://www.ncbi.nlm.nih.gov/>. GenBank Accession No. G13498.

* cited by examiner

*Primary Examiner*—Tekchand Saidha
(74) *Attorney, Agent, or Firm*—Banner & Witcoff, Ltd.

(57) ABSTRACT

The invention provides isolated nucleic acids molecules, designated MID 4460 nucleic acid molecules, which encode novel tyrosine phosphatase family members. The invention also provides antisense nucleic acid molecules, recombinant expression vectors containing MID 4460 nucleic acid molecules, host cells into which the expression vectors have been introduced, and nonhuman transgenic animals in which a MID 4460 gene has been introduced or disrupted. The invention still further provides isolated MID 4460 proteins, fusion proteins, antigenic peptides and anti-MID 4460 antibodies. Diagnostic and therapeutic methods utilizing compositions of the invention are also provided.

14 Claims, 9 Drawing Sheets cDNA Sequence of MID 4460 (SEQ ID NO:1)
```
CTAGGCCTGGGACTCCTGGGTCCCCGGCAGTGTCTGGAGGCATGGCTGGGGCTGGCGGGG
GCCTCGGGGTCTGGGGGAACCTGGTGCTGCTGGGCCTGTGCAGCTGGACAGGGGCCAGGG
CGCCTGCCCCCAACCCAGGGAGGAACCTGACAGTGGAGACTCAGACCACCAGCTCCATCT
CCCTGAGCTGGGAGGTCCCCGATGGCCTAGACTCACAGAACTCCAACTACTGGGTTCAGT
GTACTGGAGACGGCGGCACAACAGAGACTCGAAACACAACAGCCACCAACGTCACCGTGG
ATGGCCTTGGACCCGGGTCATTGTATACGTGTTCTGTGTGGGTGGAGAAAGACGGAGTAA
ATAGCTCTGTGGGGACTGTCACTACTGCCACAGCTCCCAACCCAGTGAGGAACCTGAGAG
TGGAGGCTCAGACCAACAGCTCCATCGCCCTGACCTGGGAGGTCCCCGACGGCCCAGACC
CACAGAACTCCACCTACGGGGTTGAGTACACTGGAGATGGTGGCAGAGCAGGGACTCGAA
GCACAGCACACACTAACATCACCGTGGATGGACTTGAACCCGGGTGTTTGTATGCGTTTT
CCATGTGGGTGGGAAAGAATGGAATCAACAGCTCCCGGGAGACTCGAAATGCCACCACAG
CTCACAACCCAGTGAGGAAACCTGAGAGTGGAGGCTCAGACCACCAGCTCCATCTCCCTG
AGCTGGGAGGTCCCCGATGGCACAGACCCACAGAACTCGACCTACTGCGTACGAGTGCAC
TGGAGATGGTGGCAGAACAGAGACTCGAAACACAACAGACACCAGAGTCACCAGTGGATG
GCCTTGGACCCGGGTCATTGTATACGTGTTCTGTGTGGGTGGAGAAAGACGGAGTAAATA
GCTCCTCGTGGAGATTGGTAACTAGTACCACAGCTCCCAACCCAGTGAGAAACCTGACAG
TGGAGGCTCAGACCAACAGCTCCATCGCCCTGACCTGGGAGGTCCCCGATGGCCCAGACC
CACAGAACTCCACCTACGGGGTTGAGTACACTGGAGATGGTGGCAGAGCAGGGACTCGAA
GCACAGCACACACCAACATCACCGTGGATAGACTTGAACCCGGGTGTTTGTATGTGTTTT
CCGTGTGGGTGGGAAGAATGGAATCAACAGCTCCCGGGAGACTCGAAATGCCACCACAG
CCCCCAACCCAGTGAGAAACCTCCATATGGAGACTCAGACCAACAGCTCCATCGCCCTAT
GCTGGGAAGTCCCCGATGGCCCATACCCTCAGGACTACACCTACTGGGTAGGGTACACTG
GAGACGGTGGTGGCACAGAGACCCGAAACACAACAAATACCAGTGTGACAGCTGAGAGAC
TTGAGCCCGGAACCTTGTACACATTCTCTGTATGGGCAGAAAAAAATGGAGCACGTGGCT
CCAGGCAGAATGTCAGCATCTCCACAGTCCCCAACGCAGTGACAAGCCTCAGCAAGCAGG
ACTGGACCAACAGCACCATTGCTTTGCGCTGGACAGCTCCCCAGGGCCCAGGCCAGTCTT
CCTACAGCTACTGGGTCTCATGGGTCAGGGAAGGCATGACTGACCCCAGGACCCAAAGCA
CCTCAGGTACTGACATCACCCTAAAGGAACTGGAAGCTGGCAGCCTGTACCACCTCACCG
TCTGGGCCGAGAGGAATGAGGTCAGAGGCTATAACAGCACCCTCACTGCAGCCACTGCTC
CCAATGAGGTCACAGATCTCCAGAATGAAACTCAGACTAAGAACTCAGTCATGCTGTGGT
GGAAGCCCCTGGAGACCCCCACTCTCAGTTGTACGTATACTGGGTCCAGTGGGCCAGCA
AGGGACATCCCCGGAGGGGGCAAGATCCCCAAGCGAATTGGGTCAACCAGACCAGCAGGA
CCAATGAGACGTGGTACAAAGTGGAGGCCCTGGAACCCGGGACGTTGTACAATTTCACCG
TGTGGGCAGAGAGGAATGACGTAGCCAGTTCCACGCAGAGCCTCTGTGCGTCCACATACC
CAGACACAGTCACCATCACTTCCTGTGTCAGCACCTCAGCGGGCTATGGAGTCAACTTGA
TCTGGTCCTGCCCCCAGGGAGGCTACGAGGCCTTTGAGTTGGAGGTGGGAGGACAGCGGG
GCTCCCAGGACAGATCTTCATGTGGGGAGGCTGTGTCTGTGTTGGGTCTCGGGCCGGCTC
GGTCCTACCCAGCCACCATCACGACCATCTGGGACGGAATGAAGGTCGTGTCTCACTCTG
TGGTCTGCCACACCGAGAGTGCAGGGGTCATTGCCGGAGCCTTTGTGGGCATCCTCCTGT
TTCTCATCCTCGTGGGCCTGCTGATTTTCTTCCTGAAGAGGAGGAATAAGAAGAAGCAGC
AGAAACCAGAACTCAGGGATCTGGTCTTTAGCTCCCCAGGGGACATCCCAGCTGAAGACT
TCGCTGACCACGTCAGGAAGAATGAGAGGGACAGCAACTGTGGTTTTGCAGACGAGTACC
AGCAACTCTCCCTGGTGGGCCACAGCCAGTCTCAGATGGTGGCTTCGGCTTCAGAGAACA
ACGCCAAGAACCGCTACAGAAATGTGCTGCCCTATGACTGGTCCCGGGTGCCCCTGAAGC
CATCCATGAGGAGCCAGGCTCTGACTACATCAATGCCAGCTTCATGCCCGGTCTCTGGA
GCCCCAGGAGTTCATTGCAACCCAGGGTCCCCTGCCACAGACAGTGGGTGACTTCTGGC
GCCTGGTGTGGGAACAGCAGAGCCACACCCTGGTCATGCTGACCAACTGCATGGAGGCCG
GCCGGGTGAAGTGTGAGCATTACTGGCCTCTGGACTCGCAGCCCTGCACCCATGGGCACC
TGCGGGTAACCCTGGTAGGTGAGGAAGTGATGGAGAACTGGACGGTGCGGGAACTGCTGC
TCCTCCAGGTGGAGGAGCAGAAGACACTGTCTGTGCGCCAATTCCACTACCAGGCCTGGC
CGGATCACGGCGTTCCCTCCTCCCCAGACACCTTGCTGGCTTTCTGGAGGATGCTTCGGC
AGTGGCTGGATCAGACCATGGAGGGAGGCCCACCCATTGTGCACTGCAGTGCTGGCGTGG
GTCGCACAGGAACCCTCATTGCCCTGGACGTCCTGCTCCGGCAGCTGCAGTCCGAGGGTC
TCCTTGGGCCCTTCAGCTTTGTAAGGAAGATGAGAGAGAGTCGGCCGTTGATGGTGCAGA
CTGAGGCTCAGTACGTATTCCTGCATCAGTGCATCTGCGGTTCCTCCAACAGTCAGCCCA
GGCCCCAGCCGAGAAGGAAGTCCCGTATGAGGATGTCGAAAACCTCATCTACGAGAACGT
```

Figure 1a

```
GGCCGCCATCCAGGCCCACAAGTTGGAGGTCTAAGTGACGAGGGGGCTGGGTCGGCAGCC
CAGGCATCCTCAAGCTCTGGACACCCACTTGAGCCCAGATTCCTGGAAGAGCAGAGGGCT
GGGCTCCCAGACTCCTGGGTGCTGTGGGAGGAGGGGGCTGGTATCCCAAACTCTGGTTTC
CCCAGGAGAGAGTGGTCTGGTGGGCTTCAGATGAGTCCTATGGGAGCTGGGGATCTGGAT
TCCTGGTTCCCTGAAGGAGGAGAGGGATGATAGCTTGGATTCCCTAGGTCTTTCCAGGAT
GCAGAAAGAAACAGGCTGGGGCCTGGATTCTGAGGCAGGAAGGAATTTGGGTCTGGAGTT
CTGGCTACTTGAGGACCAAAGGCAGGAAGGATCCTGCCTTGATTTTACTTCAGAAACCAA
ATCAGTCTTCTATAATCTGGGGTCGGAGGGAGTCCCTGTGCCCAAGGTCTCTCTGCACCC
CACCATCCACATGTATTTTTCCTTCTATCCCATAATTTATTAAATCACTGTTCTCCCCAG
```

Predicted Amino Acid Sequence of MID 4460 (SEQ ID NO:2)

```
MAGAGGGLGVWGNLVLLGLCSWTGARAPAPNPGRNLTVETQTTSSISLSWEVPDGLDSQN
SNYWVQCTGDGGTTETRNTTATNVTVDGLGPGSLYTCSVWVEKDGVNSSVGTVTTATAPN
PVRNLRVEAQTNSSIALTWEVPDGPDPQNSTYGVEYTGDGGRAGTRSTAHTNITVDGLEP
GCLYAFSMWVGKNGINSSRETRNATTAHNPVRKPESGGSDHQLHLPELGGPRWHRPTELD
LLRTSALEMVAEQRLETQQTPESPVDGLGPGSLYTCSVWVEKDGVNSSSWRLVTSTTAPN
PVRNLTVEAQTNSSIALTWEVPDGPDPQNSTYGVEYTGDGGRAGTRSTAHTNITVDRLEP
GCLYVFSVWVGKNGINSSRETRNATTAPNPVRNLHMETQTNSSIALCWEVPDGPYPQDYT
YWVGYTGDGGGTETRNTTNTSVTAERLEPGTLYTFSVWAEKNGARGSRQNVSISTVPNAV
TSLSKQDWTNSTIALRWTAPQGPGQSSYSYWVSWVREGMTDPRTQSTSGTDITLKELEAG
SLYHLTVWAERNEVRGYNSTLTAATAPNEVTDLQNETQTKNSVMLWWKAPGDPHSQLYVY
WVQWASKGHPRRGQDPQANWVNQTSRTNETWYKVEALEPGTLYNFTVWAERNDVASSTQS
LCASTYPDTVTITSCVSTSAGYGVNLIWSCPQGGYEAFELEVGGQRGSQDRSSCGEAVSV
LGLGPARSYPATITTIWDGMKVVSHSVVCHTESAGVIAGAFVGILLFLILVGLLIFFLKR
RNKKKQQKPELRDLVFSSPGDIPAEDFADHVRKNERDSNCGFADEYQQLSLVGHSQSQMV
ASASENNAKNRYRNVLPYDWSRVPLKPIHEEPGSDYINASFMPGLWSPQEFIATQGPLPQ
TVGDFWRLVWEQQSHTLVMLTNCMEAGRVKCEHYWPLDSQPCTHGHLRVTLVGEEVMENW
TVRELLLLQVEEQKTLSVRQFHYQAWPDHGVPSSPDTLLAFWRMLRQWLDQTMEGGPPIV
HCSAGVGRTGTLIALDVLLRQLQSEGLLGPFSFVRKMRESRPLMVQTEAQYVFLHQCICG
SSNSQPRPQPRRKSRMRMSKTSSTRTWPPSRPTSWRSK
```

Coding Sequence for GPCR 18636 (SEQ ID NO:3)

```
                                                          ATGGCTGGGGCTGGCGGGG
GCCTCGGGGTCTGGGGGAACCTGGTGCTGCTGGGCCTGTGCAGCTGGACAGGGGCCAGGG
CGCCTGCCCCCAACCCAGGGAGGAACCTGACAGTGGAGACTCAGACCACCAGCTCCATCT
CCCTGAGCTGGGAGGTCCCCGATGGCCTAGACTCACAGAACTCCAACTACTGGGTTCAGT
GTACTGGAGACGGCGGCACAACAGAGACTCGAAACACAACAGCCACCAACGTCACCGTGG
ATGGCCTTGGACCCGGGTCATTGTATACGTGTTCTGTGTGGGTGGAGAAAGACGGAGTAA
ATAGCTCTGTGGGGACTGTCACTACTGCCACAGCTCCCAACCCAGTGAGGAACCTGAGAG
TGGAGGCTCAGACCAACAGCTCCATCGCCCTGACCTGGGAGGTCCCCGACGGCCCAGACC
CACAGAACTCCACCTACGGGGTTGAGTACACTGGAGATGGTGGCAGAGCAGGGACTCGAA
GCACAGCACACACTAACATCACCGTGGATGGACTTGAACCCGGGTGTTTGTATGCGTTTT
CCATGTGGGTGGGAAAGAATGGAATCAACAGCTCCCGGGAGACTCGAAATGCCACCACAG
CTCACAACCCAGTGAGGAAACCTGAGAGTGGAGGCTCAGACCACCAGCTCCATCTCCCTG
AGCTGGGAGGTCCCCGATGGCACAGACCCACAGAACTCGACCTACTGCGTACGAGTGCAC
TGGAGATGGTGGCAGAACAGAGACTCGAAACACAACAGACACCAGAGTCACCAGTGGATG
GCCTTGGACCCGGGTCATTGTATACGTGTTCTGTGTGGGTGGAGAAAGACGGAGTAAATA
GCTCCTCGTGGAGATTGGTAACTAGTACCACAGCTCCCAACCCAGTGAGAAACCTGACAG
TGGAGGCTCAGACCAACAGCTCCATCGCCCTGACCTGGGAGGTCCCCGATGGCCCAGACC
CACAGAACTCCACCTACGGGGTTGAGTACACTGGAGATGGTGGCAGAGCAGGGACTCGAA
GCACAGCACACACCAACATCACCGTGGATAGACTTGAACCCGGGTGTTTGTATGTGTTTT
CCGTGTGGGTGGGAAGAATGGAATCAACAGCTCCCGGGAGACTCGAAATGCCACCACAG
CCCCCAACCCAGTGAGAAACCTCCATATGGAGACTCAGACCAACAGCTCCATCGCCCTAT
GCTGGGAAGTCCCCGATGGCCCATACCCTCAGGACTACACCTACTGGGTAGGGTACACTG
GAGACGGTGGTGGCACAGAGACCCGAAACACAACAAATACCAGTGTGACAGCTGAGAGAC
```

Figure 1b

```
TTGAGCCCGGAACCTTGTACACATTCTCTGTATGGGCAGAAAAAAATGGAGCACGTGGCT
CCAGGCAGAATGTCAGCATCTCCACAGTCCCCAACGCAGTGACAAGCCTCAGCAAGCAGG
ACTGGACCAACAGCACCATTGCTTTGCGCTGGACAGCTCCCCAGGGCCCAGGCCAGTCTT
CCTACAGCTACTGGGTCTCATGGGTCAGGGAAGGCATGACTGACCCCAGGACCCAAAGCA
CCTCAGGTACTGACATCACCCTAAAGGAACTGGAAGCTGGCAGCCTGTACCACCTCACCG
TCTGGGCCGAGAGGAATGAGGTCAGAGGCTATAACAGCACCCTCACTGCAGCCACTGCTC
CCAATGAGGTCACAGATCTCCAGAATGAAACTCAGACTAAGAACTCAGTCATGCTGTGGT
GGAAGGCCCCTGGAGACCCCCACTCTCAGTTGTACGTATACTGGGTCCAGTGGGCCAGCA
AGGGACATCCCCGGAGGGGCAAGATCCCCAAGCGAATTGGGTCAACCAGACCAGCAGGA
CCAATGAGACGTGGTACAAAGTGGAGGCCCTGGAACCCGGGACGTTGTACAATTTCACCG
TGTGGGCAGAGAGGAATGACGTAGCCAGTTCCACGCAGAGCCTCTGTGCGTCCACATACC
CAGACACAGTCACCATCACTTCCTGTGTCAGCACCTCAGCGGGCTATGGAGTCAACTTGA
TCTGGTCCTGCCCCCAGGGAGGCTACGAGGCCTTTGAGTTGGAGGTGGGAGGACAGCGGG
GCTCCCAGGACAGATCTTCATGTGGGGAGGCTGTGTCTGTGTTGGGTCTCGGGCCGGCTC
GGTCCTACCCAGCCACCATCACGACCATCTGGGACGGAATGAAGGTCGTGTCTCACTCTG
TGGTCTGCCACACCGAGAGTGCAGGGGTCATTGCCGGAGCCTTTGTGGGCATCCTCCTGT
TTCTCATCCTCGTGGGCCTGCTGATTTTCTTCCTGAAGAGGAGGAATAAGAAGAAGCAGC
AGAAACCAGAACTCAGGGATCTGGTCTTTAGCTCCCCAGGGGACATCCCAGCTGAAGACT
TCGCTGACCACGTCAGGAAGAATGAGAGGGACAGCAACTGTGGTTTTGCAGACGAGTACC
AGCAACTCTCCCTGGTGGGCCACAGCCAGTCTCAGATGGTGGCTTCGGCTTCAGAGAACA
ACGCCAAGAACCGCTACAGAAATGTGCTGCCCTATGACTGGTCCCGGGTGCCCCTGAAGC
CCATCCATGAGGAGCCAGGCTCTGACTACATCAATGCCAGCTTCATGCCCGGTCTCTGGA
GCCCCAGGAGTTCATTGCAACCCAGGGTCCCCTGCCACAGACAGTGGGTGACTTCTGGC
GCCTGGTGTGGGAACAGCAGAGCCACACCCTGGTCATGCTGACCAACTGCATGGAGGCCG
GCCGGGTGAAGTGTGAGCATTACTGGCCTCTGGACTCGCAGCCCTGCACCCATGGGCACC
TGCGGGTAACCCTGGTAGGTGAGGAAGTGATGGAGAACTGGACGGTGCGGGAACTGCTGC
TCCTCCAGGTGGAGGAGCAGAAGACACTGTCTGTGCGCCAATTCCACTACCAGGCCTGGC
CGGATCACGGCGTTCCCTCCTCCCCAGACACCTTGCTGGCTTTCTGGAGGATGCTTCGGC
AGTGGCTGGATCAGACCATGGAGGGAGGCCCACCCATTGTGCACTGCAGTGCTGGCGTGG
GTCGCACAGGAACCCTCATTGCCCTGGACGTCCTGCTCCGGCAGCTGCAGTCCGAGGGTC
TCCTTGGGCCCTTCAGCTTTGTAAGGAAGATGAGAGAGAGTCGGCCGTTGATGGTGCAGA
CTGAGGCTCAGTACGTATTCCTGCATCAGTGCATCTGCGGTTCCTCCAACAGTCAGCCCA
GGCCCCAGCCGAGAAGGAAGTCCCGTATGAGGATGTCGAAAACCTCATCTACGAGAACGT
GGCCGCCATCCAGGCCCACAAGTTGGAGGTCTAAGTGA
```

Amino Acid Sequence of Mature Form of MID 4460 (SEQ ID NO:4)

RAPAPNPGRNLTVETQTTSSISLSWEVPDGLDSQNSNYWVQCTGDGGTTETRNTTATNVT
VDGLGPGSLYTCSVWVEKDGVNSSVGTVTTATAPNPVRNLRVEAQTNSSIALTWEVPDGP
DPQNSTYGVEYTGDGGRAGTRSTAHTNITVDGLEPGCLYAFSMWVGKNGINSSRETRNAT
TAHNPVRKPESGGSDHQLHLPELGGPRWHRPTELDLLRTSALEMVAEQRLETQQTPESPV
DGLGPGSLYTCSVWVEKDGVNSSSWRLVTSTTAPNPVRNLTVEAQTNSSIALTWEVPDGP
DPQNSTYGVEYTGDGGRAGTRSTAHTNITVDRLEPGCLYVFSVWVGKNGINSSRETRNAT
TAPNPVRNLHMETQTNSSIALCWEVPDGPYPQDYTYWVGYTGDGGGTETRNTTNTSVTAE
RLEPGTLYTFSVWAEKNGARGSRQNVSISTVPNAVTSLSKQDWTNSTIALRWTAPQGPGQ
SSYSYWVSWVREGMTDPRTQSTSGTDITLKELEAGSLYHLTVWAERNEVRGYNSTLTAAT
APNEVTDLQNETQTKNSVMLWWKAPGDPHSQLYVYWVQWASKGHPRRGQDPQANWVNQTS
RTNETWYKVEALEPGTLYNFTVWAERNDVASSTQSLCASTYPDTVTITSCVSTSAGYGVN
LIWSCPQGGYEAFELEVGGQRGSQDRSSCGEAVSVLGLGPARSYPATITTIWDGMKVVSH
SVVCHTESAGVIAGAFVGILLFLILVGLLIFFLKRRNKKQQKPELRDLVFSSPGDIPAE
DFADHVRKNERDSNCGFADEYQQLSLVGHSQSQMVASASENNAKNRYRNVLPYDWSRVPL
KPIHEEPGSDYINASFMPGLWSPQEFIATQGPLPQTVGDFWRLVWEQQSHTLVMLTNCME
AGRVKCEHYWPLDSQPCTHGHLRVTLVGEEVMENWTVRELLLLQVEEQKTLSVRQFHYQA
WPDHGVPSSPDTLLAFWRMLRQWLDQTMEGGPPIVHCSAGVGRTGTLIALDVLLRQLQSE
GLLGPFSFVRKMRESRPLMVQTEAQYVFLHQCICGSSNSQPRPQPRRKSRMRMSKTSSTR
TWPPSRPTSWRSK

Figure 1c

```
Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - -
HMM file:                /prod/ddm/seqanal/PFAM/pfam6.2/Pfam
Sequence file:           /prod/ddm/wspace/orfanal/oa-script.20761.seq
- - - - - - - - - - - - - - - - - - - - - - - - - - - - - - - - - - - -
  Query:  4460
Scores for sequence family classification (score includes all domains):
Model          Description                                Score    E-value  N
--------       -----------                                -----    -------  ---
Y_phosphatase  Protein-tyrosine phosphatase               396.1    3.5e-115  1
fn3            Fibronectin type III domain                153.6    3.4e-42   6

Parsed for domains:
Model          Domain   seq-f seq-t    hmm-f hmm-t       score  E-value
--------       ------   ----- -----    ----- -----       -----  -------
fn3             1/6        28   108 ..     1    84 []    35.2  1.5e-06
fn3             2/6       119   201 ..     1    84 []    35.2  1.5e-06
fn3             3/6       299   381 ..     1    84 []    36.1  7.9e-07
fn3             4/6       388   469 ..     1    84 []    27.1  0.00042
fn3             5/6       477   559 ..     1    84 []    22.7  0.0089
fn3             6/6       567   656 ..     1    84 []    35.2  1.5e-06
Y_phosphatase   1/1       846  1080 ..     1   264 []   396.1  3.5e-115

Alignments of top-scoring domains:
fn3: domain 1 of 6, from 28 to 108: score 35.2, E = 1.5e-06
                   *->P.saP.tnltvtdvtstsltlsWsppt.gngpitgYevtyRqpkngg
                      P + P++nltv+ +t++s++lsW+ p++ ++  ++Y v++    ++g
         4460    28  PaPNPgRNLTVETQTTSSISLSWEVPDgLDSQNSNYWVQC-T--GDG  71 ewmneltvpgtttsytltgLkPgteYevrVqAvnggGGpeS<-*
                   +++e + +  t ++t+ gL Pg+ Y+ +V            S
         4460    72  GTTETRNTTAT-NVTVDGLGPGSLYTCSVWVEKDG--VNS          108 fn3: domain 2 of 6, from 119 to 201: score 35.2, E = 1.5e-06
                   *->PsaPtnltvtdvtstsltlsWsppt.gngpitgYevtyRqpknggew
                      P +++nl+v+++t +s+ l+W+ p++++    + Y v+y    ++g+
         4460   119  PNPVRNLRVEAQTNSSIALTWEVPDgPDPQNSTYGVEY-T--GDGGR 162
                   neltvpgtttsytltgLkPgteYevrVq.AvnggG.GpeS<-*
                   + + +t + t+ gL+Pg   Y ++        ng+ +++e+
         4460   163  AGTRSTAHT-NITVDGLEPGCLYAFSMWvGKNGINsSRET         201 fn3: domain 3 of 6, from 299 to 381: score 36.1, E = 7.9e-07
                   *->PsaPtnltvtdvtstsltlsWsppt.gngpitgYevtyRqpknggew
                      P +++nltv+++t +s+ l+W+ p++++    + Y v+y    ++g+
         4460   299  PNPVRNLTVEAQTNSSIALTWEVPDgPDPQNSTYGVEY-T--GDGGR 342
                   neltvpgtttsytltgLkPgteYevrVq.AvnggG.GpeS<-*
                   + + +t + t+  L+Pg  Y+++V       ng+ +++e+
         4460   343  AGTRSTAHT-NITVDRLEPGCLYVFSVWvGKNGINsSRET         381 fn3: domain 4 of 6, from 388 to 469: score 27.1, E = 0.00042
                   *->PsaPtnltvtdvtstsltlsWsppt.gngpitgYevtyRqpknggew
                      P +++nl+ + +t +s+ l W+ p+++         Y  v y    ++gg
         4460   388  PNPVRNLHMETQTNSSIALCWEVPDgPYPQDYTYWVGY-TGDGGG-- 431
                   neltvpgtttsytltgLkPgteYevrVqAvnggG.GpeS<-*
                   +e + + +t s+t + L+Pgt Y+++V A ++g +G +
         4460   432  TETRNTTNT-SVTAERLEPGTLYTFSVWAEKNGArGSRQ         469
fn3: domain 5 of 6, from 477 to 559: score 22.7, E = 0.0089
                   *->PsaPtnltvtdvtstsltlsWsppt.gngpitgYevtyRqpknggew
                      P a+t l+   d t +++ l+W++p +++      +Y v++   ++  ++
```

Figure 3a

```
4460    477    PNAVTSLSKQDWTNSTIALRWTAPQgPGQSSYSYWVSW-VREGMTDP  522
                      neltvpgtttsytltgLkPgteYevrVqAvnggG.GpeS<-*
                      ++++ +gt     tl+ L++g+ Y+++V A   ++ +G   S
        4460    523   RTQSTSGTD--ITLKELEAGSLYHLTVWAERNEVrGYNS         559 fn3: domain 6 of 6, from 567 to 656: score 35.2, E = 1.5e-06
                      *->PsaPtnltvtdvtstsltlsWsppt.gngpitgYevtyRqpkngge.
                         P ++t+l+ + +t +s+ l W++p ++++ +  Y v++  +k+++ +
        4460    567    PNEVTDLQNETQTKNSVMLWWKAPGdPHSQLYVYWVQW-ASKGHPRr   612

.......wneltvpgtttsytltgLkPgteYevrVqAvnggGGpeS<-*
                      +++++ +w+++t    ++t y ++ L+Pgt Y+++V A   ++   +S
        4460    613   gqdpqanWVNQTSRTNETWYKVEALEPGTLYNFTVWAERND--VAS    656

Y_phosphatase: domain 1 of 1, from 846 to 1080: score 396.1, E = 3.5e-115
                      *->NkkKNRYkdIlPYDhsRVkLtpidgeegSDYINAsyIkyIdGykqkk
                         N  KNRY+++lPYD sRV L+pi +e+gSDYINAs   +++G    ++
        4460    846    NNAKNRYRNVLPYDWSRVPLKPIHEEPGSDYINAS---FMPGLWSPQ   889 asYIATQGPLpSnTveDFWRMvWENqnsaiIVMlTrlvErgreKCdqYWP
                      +  +IATQGPLp   Tv+DFWR vWE q s++ VMlT++ E+gr+KC  +YWP
        4460    890    E-FIATQGPLP-QTVGDFWRLVWE-QQSHTLVMLTNCMEAGRVKCEHYWP   936 degegEndsetyGdisVtlkseevvledytvRtleltntgagegQdkerd
                      +           ++t+G+++Vtl+  eev  +e  +tvR+l l   +  +
        4460    937    LDSQ----PCTHGHLRVTLVGEEV-MENWTVRELLLLQVEEQ--------   973 etRevtqfhytgWPDhrgvPespkslIkfirqvrksqeqsgpsaGasdgP
                      +t+ v+qfhy +WPDh gvP+sp+ ll+f r   r + +q+ +        gP
        4460    974    KTLSVRQFHYQAWPDH-GVPSSPDTLLAFWRMLRQWLDQTMEG-----GP  1017 ivVHCSAGvGRTGTFialdimleqleaegppsDvVdvfqtVkslRsQRpg
                      +VHCSAGvGRTGT+iald +l ql++eg        + +f +V+++R   Rp
        4460   1018    PIVHCSAGVGRTGTLIALDVLLRQLQSEG----LLGPFSFVRKMRESRPL  1063 mVQTeeQYvFiYdAile<-*
                      mVQTe+QYvF++++i
        4460   1064    MVQTEAQYVFLHQCICG      1080
```

Figure 3b

View Prodom PD312226

>PD312226 p2001.1 (1) // H PHOSPHATASE TYROSINE TRANSMEMBRANE-TYPE
         Length = 217

Score = 1181 (420.8 bits), Expect = 3.9e-120, P = 3.9e-120
 Identities = 217/217 (100%), Positives = 217/217 (100%)

Query:   540 GSLYHLTVWAERNEVRGYNSTLTAATAPNEVTDLQNETQTKNSVMLWWKAPGDPHSQLYV 599
             GSLYHLTVWAERNEVRGYNSTLTAATAPNEVTDLQNETQTKNSVMLWWKAPGDPHSQLYV
Sbjct:     1 GSLYHLTVWAERNEVRGYNSTLTAATAPNEVTDLQNETQTKNSVMLWWKAPGDPHSQLYV 60

Query:   600 YWVQWASKGHPRRGQDPQANWVNQTSRTNETWYKVEALEPGTLYNFTVWAERNDVASSTQ 659
             YWVQWASKGHPRRGQDPQANWVNQTSRTNETWYKVEALEPGTLYNFTVWAERNDVASSTQ
Sbjct:    61 YWVQWASKGHPRRGQDPQANWVNQTSRTNETWYKVEALEPGTLYNFTVWAERNDVASSTQ 120

Query:   660 SLCASTYPDTVTITSCVSTSAGYGVNLIWSCPQGGYEAFELEVGGQRGSQDRSSCGEAVS 719
             SLCASTYPDTVTITSCVSTSAGYGVNLIWSCPQGGYEAFELEVGGQRGSQDRSSCGEAVS
Sbjct:   121 SLCASTYPDTVTITSCVSTSAGYGVNLIWSCPQGGYEAFELEVGGQRGSQDRSSCGEAVS 180

Query:   720 VLGLGPARSYPATITTIWDGMKVVSHSVVCHTESAGV 756
             VLGLGPARSYPATITTIWDGMKVVSHSVVCHTESAGV
Sbjct:   181 VLGLGPARSYPATITTIWDGMKVVSHSVVCHTESAGV 217

Figure 4

```
>gi|475004|dbj|BAA03645| (D15049) protein tyrosine phosphatase precursor [Homo
     sapiens] >pir|A49724|A49724 protein-tyrosine-phosphatase (EC
     3.1.3.48), receptor type H precursor - human
     Length = 1118

Plus Strand HSPs:

Score = 6029 (2759.6 bits), Expect = 0.0, P = 0.0
  Identities = 1118/1118 (100%), Positives = 1118/1118 (100%), Frame = +3

Query:     42 MAGAGGGLGVWGNLVLLGLCSWTGARAPAPNPGRNLTVETQTTSSISLSWEVPDGLDSQN 221
              MAGAGGGLGVWGNLVLLGLCSWTGARAPAPNPGRNLTVETQTTSSISLSWEVPDGLDSQN
Sbjct:      1 MAGAGGGLGVWGNLVLLGLCSWTGARAPAPNPGRNLTVETQTTSSISLSWEVPDGLDSQN  60

Query:    222 SNYWVQCTGDGGTTETRNTTATNVTVDGLGPGSLYTCSVWVEKDGVNSSVGTVTTATAPN 401
              SNYWVQCTGDGGTTETRNTTATNVTVDGLGPGSLYTCSVWVEKDGVNSSVGTVTTATAPN
Sbjct:     61 SNYWVQCTGDGGTTETRNTTATNVTVDGLGPGSLYTCSVWVEKDGVNSSVGTVTTATAPN 120

Query:    402 PVRNLRVEAQTNSSIALTWEVPDGPDPQNSTYGVEYTGDGGRAGTRSTAHTNITVDGLEP 581
              PVRNLRVEAQTNSSIALTWEVPDGPDPQNSTYGVEYTGDGGRAGTRSTAHTNITVDGLEP
Sbjct:    121 PVRNLRVEAQTNSSIALTWEVPDGPDPQNSTYGVEYTGDGGRAGTRSTAHTNITVDGLEP 180

Query:    582 GCLYAFSMWVGKNGINSSRETRNATTAHNPVRKPESGGSDHQLHLPELGGPRWHRPTELD 761
              GCLYAFSMWVGKNGINSSRETRNATTAHNPVRKPESGGSDHQLHLPELGGPRWHRPTELD
Sbjct:    181 GCLYAFSMWVGKNGINSSRETRNATTAHNPVRKPESGGSDHQLHLPELGGPRWHRPTELD 240

Query:    762 LLRTSALEMVAEQRLETQQTPESPVDGLGPGSLYTCSVWVEKDGVNSSSWRLVTSTTAPN 941
              LLRTSALEMVAEQRLETQQTPESPVDGLGPGSLYTCSVWVEKDGVNSSSWRLVTSTTAPN
Sbjct:    241 LLRTSALEMVAEQRLETQQTPESPVDGLGPGSLYTCSVWVEKDGVNSSSWRLVTSTTAPN 300

Query:    942 PVRNLTVEAQTNSSIALTWEVPDGPDPQNSTYGVEYTGDGGRAGTRSTAHTNITVDRLEP 1121
              PVRNLTVEAQTNSSIALTWEVPDGPDPQNSTYGVEYTGDGGRAGTRSTAHTNITVDRLEP
Sbjct:    301 PVRNLTVEAQTNSSIALTWEVPDGPDPQNSTYGVEYTGDGGRAGTRSTAHTNITVDRLEP 360

Query:   1122 GCLYVFSVWVGKNGINSSRETRNATTAPNPVRNLHMETQTNSSIALCWEVPDGPYPQDYT 1301
              GCLYVFSVWVGKNGINSSRETRNATTAPNPVRNLHMETQTNSSIALCWEVPDGPYPQDYT
Sbjct:    361 GCLYVFSVWVGKNGINSSRETRNATTAPNPVRNLHMETQTNSSIALCWEVPDGPYPQDYT 420

Query:   1302 YWVGYTGDGGGTETRNTTNTSVTAERLEPGTLYTFSVWAEKNGARGSRQNVSISTVPNAV 1481
              YWVGYTGDGGGTETRNTTNTSVTAERLEPGTLYTFSVWAEKNGARGSRQNVSISTVPNAV
Sbjct:    421 YWVGYTGDGGGTETRNTTNTSVTAERLEPGTLYTFSVWAEKNGARGSRQNVSISTVPNAV 480

Query:   1482 TSLSKQDWTNSTIALRWTAPQGPGQSSYSYWVSWVREGMTDPRTQSTSGTDITLKELEAG 1661
              TSLSKQDWTNSTIALRWTAPQGPGQSSYSYWVSWVREGMTDPRTQSTSGTDITLKELEAG
Sbjct:    481 TSLSKQDWTNSTIALRWTAPQGPGQSSYSYWVSWVREGMTDPRTQSTSGTDITLKELEAG 540

Query:   1662 SLYHLTVWAERNEVRGYNSTLTAATAPNEVTDLQNETQTKNSVMLWWKAPGDPHSQLYVY 1841
              SLYHLTVWAERNEVRGYNSTLTAATAPNEVTDLQNETQTKNSVMLWWKAPGDPHSQLYVY
Sbjct:    541 SLYHLTVWAERNEVRGYNSTLTAATAPNEVTDLQNETQTKNSVMLWWKAPGDPHSQLYVY 600

Query:   1842 WVQWASKGHPRRGQDPQANWVNQTSRTNETWYKVEALEPGTLYNFTVWAERNDVASSTQS 2021
              WVQWASKGHPRRGQDPQANWVNQTSRTNETWYKVEALEPGTLYNFTVWAERNDVASSTQS
Sbjct:    601 WVQWASKGHPRRGQDPQANWVNQTSRTNETWYKVEALEPGTLYNFTVWAERNDVASSTQS 660

Query:   2022 LCASTYPDTVTITSCVSTSAGYGVNLIWSCPQGGYEAFELEVGGQRGSQDRSSCGEAVSV 2201
              LCASTYPDTVTITSCVSTSAGYGVNLIWSCPQGGYEAFELEVGGQRGSQDRSSCGEAVSV
Sbjct:    661 LCASTYPDTVTITSCVSTSAGYGVNLIWSCPQGGYEAFELEVGGQRGSQDRSSCGEAVSV 720
```

Figure 5a

```
Query:  2202  LGLGPARSYPATITTIWDGMKVVSHSVVCHTESAGVIAGAFVGILLFLILVGLLIFFLKR  2381
              LGLGPARSYPATITTIWDGMKVVSHSVVCHTESAGVIAGAFVGILLFLILVGLLIFFLKR
Sbjct:   721  LGLGPARSYPATITTIWDGMKVVSHSVVCHTESAGVIAGAFVGILLFLILVGLLIFFLKR   780

Query:  2382  RNKKKQQKPELRDLVFSSPGDIPAEDFADHVRKNERDSNCGFADEYQQLSLVGHSQSQMV  2561
              RNKKKQQKPELRDLVFSSPGDIPAEDFADHVRKNERDSNCGFADEYQQLSLVGHSQSQMV
Sbjct:   781  RNKKKQQKPELRDLVFSSPGDIPAEDFADHVRKNERDSNCGFADEYQQLSLVGHSQSQMV   840

Query:  2562  ASASENNAKNRYRNVLPYDWSRVPLKPIHEEPGSDYINASFMPGLWSPQEFIATQGPLPQ  2741
              ASASENNAKNRYRNVLPYDWSRVPLKPIHEEPGSDYINASFMPGLWSPQEFIATQGPLPQ
Sbjct:   841  ASASENNAKNRYRNVLPYDWSRVPLKPIHEEPGSDYINASFMPGLWSPQEFIATQGPLPQ   900

Query:  2742  TVGDFWRLVWEQQSHTLVMLTNCMEAGRVKCEHYWPLDSQPCTHGHLRVTLVGEEVMENW  2921
              TVGDFWRLVWEQQSHTLVMLTNCMEAGRVKCEHYWPLDSQPCTHGHLRVTLVGEEVMENW
Sbjct:   901  TVGDFWRLVWEQQSHTLVMLTNCMEAGRVKCEHYWPLDSQPCTHGHLRVTLVGEEVMENW   960

Query:  2922  TVRELLLLQVEEQKTLSVRQFHYQAWPDHGVPSSPDTLLAFWRMLRQWLDQTMEGGPPIV  3101
              TVRELLLLQVEEQKTLSVRQFHYQAWPDHGVPSSPDTLLAFWRMLRQWLDQTMEGGPPIV
Sbjct:   961  TVRELLLLQVEEQKTLSVRQFHYQAWPDHGVPSSPDTLLAFWRMLRQWLDQTMEGGPPIV  1020

Query:  3102  HCSAGVGRTGTLIALDVLLRQLQSEGLLGPFSFVRKMRESRPLMVQTEAQYVFLHQCICG  3281
              HCSAGVGRTGTLIALDVLLRQLQSEGLLGPFSFVRKMRESRPLMVQTEAQYVFLHQCICG
Sbjct:  1021  HCSAGVGRTGTLIALDVLLRQLQSEGLLGPFSFVRKMRESRPLMVQTEAQYVFLHQCICG  1080

Query:  3282  SSNSQPRPQPRRKSRMRMSKTSSTRTWPPSRPTSWRSK  3395
              SSNSQPRPQPRRKSRMRMSKTSSTRTWPPSRPTSWRSK
Sbjct:  1081  SSNSQPRPQPRRKSRMRMSKTSSTRTWPPSRPTSWRSK  1118
```

Figure 5b

MID 4460, A HUMAN TYROSINE PHOSPHATASE FAMILY MEMBER AND USES THEREFOR

RELATED APPLICATIONS

This application claims priority to U.S. provisional application No. 60/323,018, filed on Sep. 18, 2001, the contents of which are incorporated herein by reference.

BACKGROUND OF THE INVENTION

Phoshpate tightly associated with protein has been known since the late nineteenth century. Since then, a variety of covalent linkages of phosphate to proteins have been found. The most common involve esterification of phosphate to serine and threonine, with smaller amounts being covalently linked to lysine, arginine, histidine, aspartic acid, glutamic acid, and cysteine. The occurrence of phosphorylated proteins implies the existence of one or more protein kinases capable of phosphorylating amino acid residues on proteins, and also of protein phosphatases capable of hydrolyzing phosphorylated amino acid residues on proteins.

Protein kinases play critical roles in the regulation of biochemical and morphological changes associated with cellular growth and division (D'Urso, G. et al. (1990) Science 250: 786–791; Birchmeier, C. et al. (1993) Bioessays 15: 185–189). They serve as growth factor receptors and signal transducers and have been implicated in cellular transformation and malignancy (Hunter, T. et al. (1992) Cell 70: 375–387; Posada, J. et al. (1992) Mol. Biol. Cell 3: 583–592; Hunter, T. et al. (1994) Cell 79: 573–582). For example, protein kinases have been shown to participate in the transmission of signals from growth-factor receptors (Sturgill, T. W. et al. (1988) Nature 344: 715–718; Gomez, N. et al. (1991) Nature 353: 170–173), control of entry of cells into mitosis (Nurse, P. (1990) Nature 344: 503–508; Maller, J. L. (1991) Curr. Opin. Cell Biol. 3–269–275) and regulation of actin bundling (Husain-Chishti, A. et al. (1988) Nature 334: 718–721).

The overall level, in cells, of protein tyrosine phosphorylation, as well as the phosphorylated state of any given protein, arises from the balance of Protein Tyrosine Kinase (PTK) and Protein Tyrosine Phosphatase (PTPase) activities. Thus PTPases have been proposed as key regulatory elements of cell growth control (Hunter, 1989, Cell 58:1013–1016).

PTKs were discovered and characterized more than one decade earlier than PTPases and in the last few years a large number of studies has led to the identification of many new PTPases and some of them have been accurately characterized. In addition, findings on the biological role of some PTPases in cells have recently been reported (Pondaven, 1991, Adv Prot Phosphatases 6:35–57). Current work suggests that PTKs and PTPases are equally important in many biological processes ranging from cell growth control to cell differentiation and development. In particular, the oncogenic potential of PTKs and the ability of PTPases to counteract PTK oncogenic activation by antiproliferative action suggests that the genes coding for PTPases, in many instances, may be considered tumor-suppressing genes or even anti-oncogenes The existence of PTPases was first predicted to explain the rapid loss of phosphorylation of in vitro phosphorylated membrane proteins (Carpenter et al., 1979, J. Biol. Chem. 254:4884–4891). The main PTPase in human placenta (PTP1B) was purified to homogeneity and sequenced (Tonks et al., 1988, J. Biol. Chem. 263:6722–2730; Charbonneau et al., 1989, Proc. Natl. Acad. Sci. USA 86:5252–5256). Sequence homology between the catalytic domain of PTP1B and the leukocyte common antigen (LCA, or CD45) was demonstrated, indicating that PTPases can be considered a family of structurally related molecules.

The effects of many growth factors such as NGF, BDNF, NT3, FGF, insulin and IGF1 are known to be mediated by high-affinity receptors with tyrosine kinases activity (Fantl et al. Annu. Rev. Biochem., 62 (1993) 453–481; Schlessinger and Ulrich Neuron, 9 (1992) 383–391; Ullrich and Schlessinger Cell, 61 (1990) 203–212). Expression of several tyrosine phosphatase genes has been detected in the brain (Jones et al. J. Biol. Chem., 264 (1989) 7747–7753), including RPTPα (Kaplan et al. Proc. Natl. Acad. Sci. USA, 87 91990) 7000–7004; Sap et al. Proc. Natl. Acad. Sci. USA, 87 (1990) 6112–6116), RNPTPX (Guan et al. Proc Natl. Acad. Sci. USA, 87 (19910) 1501–1505), STEP (Lombroso et al. Proc. Natl. Acad. Sci. USA, 88 (1991) 7242–7246), SH-PTP2 (Freeman et al. Proc. Natl. Acad. Sci. USA, 89 (1992) 11239–11243), MPTPδ (Mizuno et al. Mol. Cell. Biol., 13 (1993) 5513–5523), DPTP99A and DPTP10D (Yang et al. Cell, 67 (1991) 661–673).

Intraventricular administration of either NGF, BDNF, insulin or IGF1 prevents delayed neuronal death in the CA1 subfield of the hippocampus (Beck et al. J. Cereb Blood Flow Metab., 14 (1994) 689–692; Shigeno et al. J. Neurosci., 11 (1991) 2914–2919; Zhu and Auer J. Cereb. Blood Flow Metab., 14 (1994) 237–242).

Tyrosine kinase inhibitors block the tyrosine phosphorylation of MAP kinase (Blenis Proc. Natl. Acad. Sci. USA, 90 (1993) 5889–5892; Pelech and Sanghera Science, 257 (1992) 1335–1356) and prevent delayed neuronal death after forebrain ischemia (Kindy J. Cereb. Blood Flow Metab, 13 (1993) 372–377). During reperfusion after ischemia, tyrosine phosphorylation of proteins increases in the hippocampus but some proteins in the hippocampus are dephosphorylated (Campos-Gonzalez J. Neurochem., 59 (1992) 1955–1958; Hu and Wieloch J. Neurochem, 62 (1994) 1357–1367; Takano et al. J. Cereb. Blood Flow Metab., 15 (1995) 33–41). These observations suggest that tyrosine phosphorylation plays an important role in the delayed neuronal death which occurs as a result of ischemia-reperfusion injury.

A number of PTPases, in addition to the hydrolytic activity on phosphotyrosine, show some phosphoserine/phosphothreonine phosphatase activity. These enzymes, mostly localized in the nucleus and referred to as dual-specificity PTPases (dsPTPases), are emerging as a subclass of PTPases acting as important regulators of cell cycle control and mitogenic signal transduction possibly by controlling the activity of signal transduction proteins like ERK. In fact, they appear responsible for in vivo nuclear dephosphorylation and inactivation of nuclear dephosphorylation and inactivation of MAP kinases (Alessi et al., 1995, Curr Biol 5:195–283). These enzymes exhibit sequence identity to the vaccinia H-1 gene product, the first identified dsPTPase (Guan et al., 1991, Nature 350:359–362). Several dsPTPases differing from each other in length have been identified. These enzymes and the other PTPase subclasses share an active site sequence motif showing only a limited sequence homology beyond this region.

Given the importance of such protein tyrosine phosphatases in the regulation of the cell cycle, there exists a need to identify novel protein tyrosine phosphatases which function as modulators in the cell cycle such as the suppression of proliferation and whose aberrant function can result in disorders arising from improper cell cycle regulation such as cancer.

SUMMARY OF THE INVENTION

The present invention is based, in part, on the discovery of a novel tyrosine phosphatase family member, referred to herein as "MID 4460". The nucleotide sequence of a cDNA encoding MID 4460 is shown in SEQ ID NO:1, and the amino acid sequence of a MID 4460 polypeptide is shown in SEQ ID NO:2. In addition, the nucleotide sequence of the coding region is depicted in SEQ ID NO:3.

Accordingly, in one aspect, the invention features a nucleic acid molecule which encodes a MID 4460 protein or polypeptide, e.g., a biologically active portion of the MID 4460 protein. In a preferred embodiment, the isolated nucleic acid molecule encodes a polypeptide having the amino acid sequence of SEQ ID NO:2. In other embodiments, the invention provides isolated MID 4460 nucleic acid molecules having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule which hybridizes under a stringent hybridization condition as described herein to a nucleic acid molecule comprising the nucleotide sequence of SEQ ID NO:1 NO:1 or SEQ ID NO:3, wherein the nucleic acid encodes a full length MID 4460 protein or an active fragment thereof.

In a related aspect, the invention further provides nucleic acid constructs which include a MID 4460 nucleic acid molecule described herein. In certain embodiments, the nucleic acid molecules of the invention are operatively linked to native or heterologous regulatory sequences. Also included are vectors and host cells containing the MID 4460 nucleic acid molecules of the invention e.g., vectors and host cells suitable for producing polypeptides.

In another related aspect, the invention provides nucleic acid fragments suitable as primers or hybridization probes for the detection of MID 4460-encoding nucleic acids.

In still another related aspect, isolated nucleic acid molecules that are antisense to a MID 4460 encoding nucleic acid molecule are provided.

In another aspect, the invention features MID 4460 polypeptides, and biologically active or antigenic fragments thereof that are useful, e.g., as reagents or targets in assays applicable to treatment and diagnosis of tyrosine phosphatase-associated or other MID 4460-associated disorders. In another embodiment, the invention provides MID 4460 polypeptides having a MID 4460 activity. Preferred polypeptides are MID 4460 proteins including at least one tyrosine phosphatase domain, and, preferably, having a MID 4460 activity, e.g., a MID 4460 activity as described herein.

In other embodiments, the invention provides MID 4460 polypeptides, e.g., a MID 4460 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under a stringent hybridization condition as described herein to a nucleic acid molecule comprising the nucleotide sequence of SEQ ID NO:1 or SEQ ID NO:3, wherein the nucleic acid encodes a full length MID 4460 protein or an active fragment thereof.

In a related aspect, the invention further provides nucleic acid constructs which include a MID 4460 nucleic acid molecule described herein.

In a related aspect, the invention provides MID 4460 polypeptides or fragments operatively linked to non-MID 4460 polypeptides to form fusion proteins.

In another aspect, the invention features antibodies and antigen-binding fragments thereof, that react with, or more preferably specifically or selectively bind MID 4460 polypeptides.

In another aspect, the invention provides methods of screening for compounds that modulate the expression or activity of the MID 4460 polypeptides or nucleic acids.

In still another aspect, the invention provides a process for modulating MID 4460 polypeptide or nucleic acid expression or activity, e.g., using the compounds identified in the screens described herein. In certain embodiments, the methods involve treatment of conditions related to aberrant activity or expression of the MID 4460 polypeptides or nucleic acids, such as conditions or disorders involving aberrant or deficient tyrosine phosphatase function or expression. Examples of such disorders include, but are not limited to, cardiovascular disorders including, but not limited to, hypercholesterolemia and atherosclerosis, and liver disorders.

The invention also provides assays for determining the activity of or the presence or absence of MID 4460 polypeptides or nucleic acid molecules in a biological sample, including for disease diagnosis.

In a further aspect, the invention provides assays for determining the presence or absence of a genetic alteration in a MID 4460 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a MID 4460 molecule. In one embodiment, the capture probe is a nucleic acid, e.g., a probe complementary to a MID 4460 nucleic acid sequence. In another embodiment, the capture probe is a polypeptide, e.g., an antibody specific for MID 4460 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIGS. 1a–c depicts a cDNA sequence (SEQ ID NO:1) and predicted amino acid sequence (SEQ ID NO:2) of human MID 4460. The methionine-initiated open reading frame of human MID 4460 (without the 5' and 3' untranslated regions of SEQ ID NO:1) is shown also as the coding sequence, SEQ ID NO:3. The amino acid sequence of the mature protein with the signal sequence cleaved is shown as SEQ ID NO:4.

FIGS. 3a–b depicts an alignment of the tyrosine phosphatase domain of human MID 4460 with a consensus amino acid sequence derived from a hidden Markov model (HMM) from PFAM. The upper sequence is the consensus amino acid sequence SEQ ID NO:10), while the lower amino acid sequence corresponds to amino acids 846 to 1080 of SEQ ID NO:2.

FIG. 4 depicts a BLAST alignment of the human MID 4460 tyrosine phosphatase domain with a consensus amino acid sequence of a domain derived from the ProDomain database ("Full Name of Prodom description;" No. PD312226; ProDomain Release 2001.1; http://www.toulouse.inra.fr/prodom.html). The lower sequence is amino acid residues 1 to 217 of the 217 amino acid PD3 12226 consensus sequence (SEQ ID NO:11), while the upper amino acid sequence corresponds to the tyrosine phosphatase domain of human MID 4460, amino acid residues 540 to 756 of SEQ ID NO:2. The BLAST algorithm identifies multiple local alignments between the consensus amino acid sequence and human MID 4460.

FIGS. 5a–b depicts a GAP alignment of human MID 4460 with protein-tyrosine phosphatase (EC 3.1.3.48), receptor type H precursor (SAP-1; D15049 in Genbank). The lower sequence in the figure is amino acids 1 to 1118 of human MID 4460 (SEQ ID NO:2) while the upper sequence is amino acids 42 to 3395 of D15049 (which is 100% identical to amino acids 1 to 1118 of SEQ ID NO:2). GAP alignments use a matrix made by matblas from blosum62.iij.

DETAILED DESCRIPTION OF THE INVENTION

Figure 2:
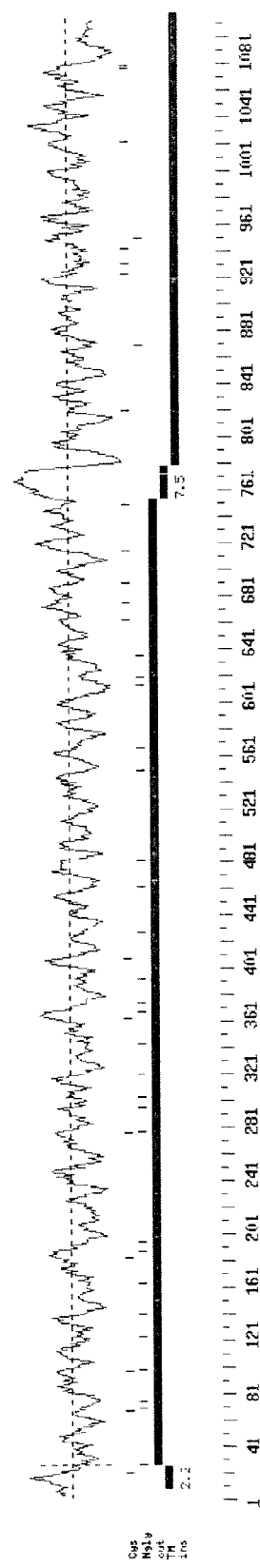
FIG. 2 depicts a hydropathy plot of human MID 4460. Relatively hydrophobic residues are shown above the dashed horizontal line, and relatively hydrophilic residues are below the dashed horizontal line. The cysteine residues (cys) are indicated by short vertical lines just below the hydropathy trace. The numbers corresponding to the amino acid sequence of human MID 4460 are indicated. Polypeptides of the invention include fragments which include: all or part of a hydrophobic sequence, e.g., a sequence above the dashed line, e.g., the sequence from about amino acid 1 to 25, from about 85 to 100, from about 355 to 365, from about 710 to 720, from about 750 to 775, and from about 1020 to 1040 of SEQ ID NO:2; all or part of a hydrophilic sequence, e.g., a sequence below the dashed line, e.g., the sequence from about amino acid 65 to 85, from about 140 to 175, from about 190 to 225, from about 230 to 240, from about 250 to 265, from about 315 to 350, from about 365 to 395, from about 402 to 422, from about 420 to 435, from about 450 to 470, from about 480 to 488, from about 495 to 505, from about 510 to 525, from about 540 to 558, from about 561 to 580, from about 595 to 630, from about 700 to 715, from about 773 to 790, from about 800 to 818, from about 835 to 855, from about 921 to 945, from about 995 to 1015, and from about 1075 to 1118 of SEQ ID NO:2; a sequence which includes a Cys, or a glycosylation site.

The human MID 4460 sequence (FIG. 1a; SEQ ID NO:1), which is approximately 3900 nucleotides long including untranslated regions, contains a predicted methionine-initiated coding sequence of about 3357 nucleotides, including the termination codon (nucleotides indicated as coding of SEQ ID NO:1 in FIGS. 1a–c; SEQ ID NO:3). The coding sequence encodes a 1118 amino acid protein (SEQ ID NO:2). The human MID 4460 protein of SEQ ID NO:2 and FIG. 2 includes an amino-terminal hydrophobic amino acid sequence, consistent with a signal sequence, of about 25 amino acids (from amino acid 1 to about amino acid 25 of SEQ ID NO:2, PSORT, Nakai and Kanehisa (1992) *Genomics* 14:897–911), which upon cleavage results in the production of a mature protein form. This mature protein form is approximately 1093 amino acid residues in length (from about amino acid 26 to amino acid 1118 of SEQ ID NO:2).

Human MID 4460 contains the following regions or other structural features (for general information regarding PFAM identifiers, PS prefix and PF prefix domain identification numbers, refer to Sonnhammer et al. (1997) *Protein* 28:405–420 and http://www.psc.edu/general/software/packages/pfam/pfam.html):

a fibronectin type III domain (PFAM Accession Number PF00041) located at about amino acid residues 28 to 108, 119 to 201, 299 to 381, 388 to 469, 477 to 559, 567 to 656 of SEQ ID NO:2;

a protein-tyrosine phosphatase domain (PFAM Accession Number PF00102) located at about amino acid residues 846 to 1080 of SEQ ID NO:2;

a phosphatase hydrolase glycoprotein repeat transmembrane signal precursor protein domain (ProDom No. PD016388) located at about amino acid residues 20 to 756 of SEQ ID NO:2;

a phosphatase hydrolase protein-tyrosine PTPase domain (ProDom No. PD061758) located at about amino acid residues 31 to 1027 of SEQ ID NO:2;

a phosphatase tyrosine SAP-1 receptor-type PTP precursor cancer-associated hydrolase protein-tyrosine domain (ProDom No. PD127840) located at about amino acid residues 779 to 814 of SEQ ID NO:2;

a phosphatase type hydrolase non-receptor PTPase tyrosine phosphotyrosine domain (ProDom No. PD097276) located at about amino acid residues 783 to 865 of SEQ ID NO:2;

a phosphatase hydrolase tyrosine repeat osteotesticular precursor cell signal glycoprotein transmembrane domain (ProDom No. PD038230) located at about amino acid residues 797 to 954 of SEQ ID NO:2;

a hydrolase phosphatase receptor tyrosine protein-tyrosine precursor signal immunoglobulin domain transmembrane domain (ProDom No. PD333871) located at about amino acid residues 917 to 1027 of SEQ ID NO:2;

a hydrolase R09E10.2 similar T22C1.8 F54F12.1 F36H1.3 protein-tyrosine phosphatase H06104.5 domain (ProDom No. PD028836) located at about amino acid residues 971 to 1978 of SEQ ID NO:2;

a H phosphatase tyrosine transmembrane domain (ProDom No. PD312226) located at about amino acid residues 27 to 756 of SEQ ID NO:2;

two transmembrane domains (predicted by MEMSAT, Jones et al. (1994) *Biochemistry* 33:3038–3049) at about amino acids 8 to 25 and 754 to 778 of SEQ ID NO:2 or at about amino acids 59 to 76 and 729 to 753 of the mature protein (SEQ ID NO:4);

a tyrosine specific protein phosphatase active site located at about amino acids 1020 to 1032 (VHCSAGVGRTGTL) of SEQ ID NO:2;

five dileucine motifs (PSORT, http://psort.nibb.ac.jp.) located at about amino acids 965 to 966, 966 to 967, 967 to 968, 998 to 999,and 1038 to 1039 of SEQ ID NO:2;

nine protein kinase C phosphorylation sites (Prosite PS00005) located at about amino acids 197 to 199 (SSR), 289 to 291 (SWR), 377 to 379 (SSR), 533 to 535 (TLK), 624 to 626 (TSR), 961 to 963 (TVR), 977 to 979 (SVR), 1103 to 1105 (STR), and 1114 to 1116 (SWR) of SEQ ID NO:2;

seventeen casein kinase II phosphorylation sites (Prosite PS00006) located at about amino acids 197 to 200 (SSRE), 237 to 240 (TELD), 245 to 248 (SALE), 263 to 266 (SPVD), 377 to 380 (SSRE), 484 to 487 (SKQD), 528 to 531 (SGTD), 533 to 536 (TLKE), 665 to 668 (TYPD), 713 to 716 (SCGE), 735 to 738 (TIWD), 798 to 801 (SPGD), 842 to 845 (SASE), 887 to 890 (SPQE), 901 to 904 (TVGD), 961 to 964 (TVRE), and 993 to 996 (SSPD) of SEQ ID NO:2;

one cAMP/cGMP-dependent protein kinase phosphorylation sites (Prosite PS00004) located at about amino acids 1091 to 1094 (RRKS) of SEQ ID NO:2;

one tyrosine kinase phosphorylation site (Prosite PS00007) located at about amino acids 626 to 632 (RT-NETWY);

twenty-seven N-glycosylation sites (Prosite PS00001) located at about amino acids 35 to 38 (NLTV), 78 to 81 (NTTA), 83 to 86 (NVTV), 107 to 110 (NSSV), 132 to 135 (NSSI), 149 to 152 (NSTY), 172 to 175 (NITV), 196 to 199 (NSSR), 203 to 206 (NATT), 286 to 289 (NSSS), 304 to 307 (NLTV), 312 to 315 (NSSI), 329 to 332 (NSTY), 352 to 355 (NITV), 376 to 379 (NSSR), 383 to 386 (NATT), 401 to 404 (NSSI), 436 to 439 (NTTN), 470 to 473 (NVSI), 490 to 493 (NSTI), 558 to 561 (NSTL), 575 to 578 (NETQ), 622 to 625 (NQTS), 628 to 631 (NETW), 644 to 647 (NFTV), 878 to 881 (NASF), and 959 to 962 (NWTV) of SEQ ID NO:2; and twenty-six N-myristoylation sites (Prosite PS00008) located at about amino acids 3 to 8 (GAGGGL), 9 to 14 (GVWGNL), 72 to 77 (GTTETR), 88 to 93 (GLGPGS), 105 to 110 (GVNSSV), 111 to 116 (GTVTTA), 153 to 158 (GVEYTG), 160 to 165 (GGRAGT), 177 to 182 (GLEPGC), 194 to 199 (GINSSR), 267 to 272 (GLGPGS), 284 to 289 (GVNSSS), 333 to 338 (GVEYTG), 340 to 345 (GGRAGT), 374 to 379 (GINSSR), 430 to 435 (GGTETR), 450 to 455 (GTLYTF), 463 to 468 (GARGSR), 529 to 534 (GTDITL), 640 to 645 (GTLYNF), 693 to 698 (GGYEAF), 703 to 708 (GGQRGS), 722 to 727 (GLGPAR), 755 to 760 (GVIAGA), 1025 to 1030 (GVGRTG), and 1080 to 1085 (GSSNSQ) of SEQ ID NO:2.

The MID 4460 protein contains a significant number of structural characteristics in common with members of the tyrosine phosphatase family and the fibronectin family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologs of non-human origin, e.g., rat or mouse proteins. Members of a family also can have common functional characteristics.

As used herein, the term "tyrosine phosphatase" or "PTPase" includes a protein or polypeptide which is capable of catalyzing the hydrolysis of a phosphate ester bond of a phosphorylated tyrosine, serine, or threonine residue, preferably the phosphorylated amino acid residue is part of a peptide, polypeptide, or protein.

Members of a tyrosine phosphatase family of proteins are characterized by a receptor-like extracellular regions connected to the intracellular (catalytic) domains by a short transmembrane segment (Streuli and Saito, 1993, *Adv. Prot. Phosphatases* 7:67–94). The non-transmembrane (cytoplasmic) PTPases typically include at least one catalytic domain (Koch et al. 1991, *Science* 252:1013–1016). An alignment of the MID 4460 protein with protein tyrosine phosphatase precursor (EC 3.1.3.48), receptor type H precursor is shown in FIG. 5 and demonstrates about 100% sequence identity between the two sequences (as calculated in matblas from the blosum62.iij matrix).

A MID 4460 polypeptide can include a "protein-tyrosine phosphatase domain" or regions homologous with a "protein-tyrosine phosphatase domain". A MID 4460 polypeptide can include or further include a "fibronectin type III domain" or regions homologous with a "fibronectin type III domain," and at least one catalytic region.

As used herein, the term "protein-tyrosine phosphatase domain" includes an amino acid sequence of about 200 to 400 amino acid residues in length and having a bit score for the alignment of the sequence to the protein-tyrosine phosphatase domain (HMM) of at least 300. Preferably a protein-tyrosine phosphatase domain mediates the catalysis of the hydrolysis of a phosphate ester bond. Preferably, a protein-tyrosine phosphatase domain includes at least about 100 to 500 amino acids, more preferably about 200 to 300 amino acid residues, or about 250 to 300 amino acids and has a bit score for the alignment of the sequence to the protein-tyrosine phosphatase domain (HMM) of at least 300, 350, 375, or greater. A protein-tyrosine. phosphatase domain is capable of catalyzing the hydrolysis of a phosphate ester bond. The protein-tyrosine phosphatase domain can include a Prosite tyrosine specific protein phosphatase active site signature sequence PS00383, which has L,I,V,M, or F at position 1: HCXXGXXX (SEQ ID NO:9) at positions 2–9; S, T, or C at position 10; S, T, A, G, or P at position 11; X at position 12; and L, I, V, M, F, or Y at position 13, or sequences homologous thereto. In the above conserved signature sequence, and other motifs or signature sequences described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (( )) indicate the number of residues represented by the accompanying amino acid. The protein-tyrosine phosphatase domain is located in the C-terminal cytoplasmic domain of human MID 4460 polypeptide and which corresponds to about amino acids 1020 to 1032 of SEQ ID NO:2. The protein-tyrosine phosphatase domain (HMM) has been assigned the PFAM Accession Number PF00102 (http://genome.wustl.edulPfaml.html). Additionally, the protein-tyrosine phosphatase domain (HMM) has been assigned the SMART identifier ptp_7 or PTPc_3 (http://smart.embl-heidelberg.de/). As used herein, the "protein-tyrosine phosphatase domain" is a portion of the human MID 4460 protein which is homologous, e.g., at least about 84%, 85%, 86%, 87%, 88%, 89%, 90%, 91%, 92%, 93%, 94%, 95%, 96%, 97%, 98%, or 99% identical to either or both of the following ProDom family "H phosphatase tyrosine transmembrane-type" domain (ProDomain Release 2001.1; http://www.toulouse.inra.fr/prodom.html, FIG. 4). An alignment of the protein-tyrosine phosphatase domain (amino acids 1 to 217 of SEQ ID NO:2) of human MID 4460 with PD312226 derived from a BLAST search model shows 100% identity (as calculated in ProDomain from the blosum62 matrix, FIG. 4). An alignment of the protein-tyrosine phosphatase domain (amino acids 846 to 1080 of SEQ ID NO:2) of human MID 4460 with the Pfam protein-tyrosine consensus amino acid sequence (SEQ ID NO:10) derived from a hidden Markov model is depicted in FIG. 3.

In a preferred embodiment, a MID 4460 polypeptide or protein has a "protein tyrosine phosphatase domain" or a region which includes at least about 200 to 300, more preferably about 250 to 300, or 275 to 300 amino acid residues and has at least about 60%, 70%, 80%, 90%, 95%, 99%, or 100% homology with a "protein tyrosine phosphatase domain domain," e.g., the protein tyrosine phosphatase domain of human MID 4460 (e.g., residues 846 to 1080 of SEQ ID NO:2).

To identify the presence of a "protein tyrosine phosphatase" domain in a MID 4460 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405–420 and a detailed description of HMMs can be found, for example, in Gribskov et al. (1990) *Meth. Enzymol.*183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference. A search was performed against the HMM database resulting in the identification of a "protein-tyrosine phosphatase" domain in the amino acid sequence of human MID 4460 at about residues 846 to 1080 of SEQ ID NO:2 (see FIG. 1).

An additional method to identify the presence of a "protein tyrosine phosphatase" domain in a MID 4460 protein sequence, and make the determination that a polypeptide or protein of interest has a particular profile, the amino acid sequence of the protein can be searched against a SMART database (Simple Modular Architecture Research Tool, http://smart.embl-heidelberg.de/) of HMMs as described in Schultz et al. (1998), *Proc. Natl. Acad. Sci. USA* 95:5857 and Schultz et al. (2000) *Nucl. Acids Res* 28:231. The database contains domains identified by profiling with the hidden Markov models of the HMMer2 search program (Durbin et al. (1998) *Biological sequence analysis: probabilistic models of proteins and nucleic acids.* Cambridge University Press.; http://hmmer.wustl.edu/). The database also is extensively annotated and monitored by experts to enhance accuracy. A search was performed against the HMM database resulting in the identification of a "protein tyrosine kinase" domain in the amino acid sequence of human MID 4460 at about residues 821 to 1083 of SEQ ID NO:2 (see FIG. 1).

For further identification of domains in a MID 4460 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263–267). The ProDom protein domain database consists of an automatic compilation of homologous domains. Current versions of ProDom are built using recursive PSI-BLAST searches (Altschul et al. (1997) *Nucleic Acids Res.* 25:3389–3402; Gouzy et al. (1999) *Computers and Chemistry* 23:333–340) of the SWISS-PROT 38 and TREMBL protein databases. The database automatically generates a consensus sequence for each domain. A BLAST search was performed against the HMM database resulting in the identification of a "protein tyrosine phosphatase" domain in the amino acid sequence of human MID 4460 at about residues 27 to 756 of SEQ ID NO:2 (see FIG. 1).

A MID 4460 molecule can further include a fibronectin type III domain, preferably two, three, four, five, or six fibronectin type III domains at about residues 28 to 108, about 119 to 201, about 299 to 381, about 388 to 469, about 477 to 559, and about 567 to 656 of SEQ ID NO:2.

A MID 4460 polypeptide can include at least one, preferably two "transmembrane domains" or regions homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95%, or more of the amino acids of a transmembrane domain are hydrophobic, e.g., leucines, isoleucines, tyrosines, or tryptophans. Transmembrane domains typically have alpha-helical structures and are described in, for example, Zagotta et al., (1996) *Annual Rev. Neurosci.* 19:235–263, the contents of which are incorporated herein by reference. The transmembrane domains of human MID 4460 is located at about residues 8 to 25 and 754 to 778 of SEQ ID NO:2 or at about residues 59 to 76 and 729 to 753 of SEQ ID NO:4.

In a preferred embodiment, a MID 4460 polypeptide or protein has at least one, preferably two "transmembrane domains" or a region which includes at least about 12 to 35 more preferably about 14 to 30 or 15 to 25 amino acid residues and has at least about 60%, 70% 80% 90% 95%, 99%, or 100% homology with a "transmembrane domain," e.g., the transmembrane domains of human MID 4460 (e.g., residues 8 to 25 and 754 to 778 of SEQ ID NO:2). The transmembrane domain of human MID 4460 is visualized in the hydropathy plot (FIG. 2) as regions of about 15 to 25 amino acids where the hydropathy trace is mostly above the horizontal line.

To identify the presence of a "transmembrane" domain in a MID 4460 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

A MID 4460 polypeptide can include at least one, preferably two "non-transmembrane regions." As used herein, the term "non-transmembrane region" includes an amino acid sequence not identified as a transmembrane domain. The non-transmembrane regions in MID 4460 are located at about amino acids 1 to 754 and 778 to 1118 of SEQ ID NO:2. The non-transmembrane region may be cytoplasmic or extracellular. The extracellular portion (about amino acids 1 to 754 of SEQ ID NO:2) may be act as an adhesion molecule, may bind a specific ligand, and/or may be important in cell-to-cell contact. The cytoplasmic portion (about amino acids 778 to 1118 of SEQ ID NO:2) may contain the catalytic domain.

The non-transmembrane regions of MID 4460 include at least one cytoplasmic region. When located at the C-terminus, the cytoplasmic region is referred to herein as the "C-terminal cytoplasmic domain." As used herein, an "C-terminal cytoplasmic domain" includes an amino acid sequence having about 1 to 400, preferably about 1 to 375, more preferably about 1 to 350, or even more preferably about 1 to 340 amino acid residues in length, is located inside of a cell or within the cytoplasm of a cell and has catalytic domain. The N-terminal amino acid residue of an "C-terminal cytoplasmic domain" is adjacent to an C-terminal amino acid residue of a transmembrane domain in a MID 4460 protein. For example, an C-terminal cytoplasmic domain is located at about amino acid residues 778 to 1118 of SEQ ID NO:2.

In a preferred embodiment, a MID 4460 polypeptide or protein has a C-terminal cytoplasmic domain or a region which includes at least about 300, preferably about 300 to 400, and more preferably about 300 to 350 amino acid residues and has at least about 60%, 70%, 80%, 90%, 95%, 99%, or 100% homology with a "C-terminal cytoplasmic domain", e.g., the C-terminal cytoplasmic domain of human MID 4460 (e.g., residues 778 to 1118 of SEQ ID NO:2).

The non-transmembrane regions of MID 4460 include at least one extracellular region. When located at the N-terminus, the extracellular region is referred to herein as the "N-terminal extracellular domain." As used herein, an "N-terminal extracellular domain" includes an amino acid sequence having about 1 to 800, preferably about 1 to 775, more preferably about 1 to 760, or even more preferably about 1 to 754 amino acid residues in length, is located inside of a cell or within the cytoplasm of a cell and has catalytic domain. The C-terminal amino acid residue of an "N-terminal extracellular domain" is adjacent to an N-terminal amino acid residue of a transmembrane domain in a MID 4460 protein. For example, an N-terminal extracellular domain is located at about amino acid residues 1 to 754 of SEQ ID NO:2.

In a preferred embodiment, a MID 4460 polypeptide or protein has an N-terminal extracellular domain or a region which includes about 1 to 800, preferably about 1 to 775, and more preferably about 1 to 750 amino acid residues and has at least about 60%, 70% 80% 90% 95%, 99%, or 100% homology with an "N-terminal extracellular domain," e.g., the N-terminal extracellular domain of human MID 4460 (e.g., residues 1 to 754 of SEQ ID NO:2).

A human MID 4460 protein can further include a dileucine motif (e.g., residues 965 to 966, 966 to 967, 967 to 968, 998 to 999, and 1038 to 1039 of SEQ ID NO:2) and/or a tyrosine specific protein phosphatase active site sequence (e.g., residues 1020 to 1032 of SEQ ID NO:2).

A MID 4460 family member can include at least one, two, three, four, five, or six fibronectin type III domains or at least one protein tyrosine phosphatase domain or transmembrane or non-transmembrane domains. A MID 4460 family member can include at least one tyrosine specific protein phosphatase active site sequence (Prosite PS00383). Furthermore, a MID 4460 family member can include at least one, two, three, four, five, six, seven, eight, nine, ten, eleven, twelve, thirteen, fourteen, fifteen, sixteen, preferably seventeen casein kinase II phosphorylation sites (Prosite PS00006); at least one, two, three, four, five, six, seven, eight, and preferably nine protein kinase C phosphorylation sites (Prosite PS00005); at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, and preferably twenty-seven N-glycosylation site (Prosite PS00001); at least one cAMP/cGMP protein kinase phosphorylation site (Prosite PS00004); at least one tyrosine kinase phosphorylation site (Prosite PS00007); and at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, and preferably twenty-six N-myristoylation sites (Prosite PS00008).

As the MID 4460 polypeptides of the invention can modulate MID 4460-mediated activities, they can be useful for developing novel diagnostic and therapeutic agents for tyrosine phosphatase-associated or other MID 4460-associated disorders, as described below.

As used herein, a "tyrosine phosphatase-associated activity" includes an activity which involves catalysis of the hydrolysis reaction of a phosphate ester bond. The activity may also involve the interaction of a phosphatase protein with a target molecule such as a phosphorylated protein or peptide. Members of the family can play a role in cardiovascular disease or neoplastic diseases.

As used herein, a "MID 4460 activity", "biological activity of MID 4460" or "functional activity of MID 4460", refers to an activity exerted by a MID 4460 protein, polypeptide or nucleic acid molecule on e.g., a MID 4460-responsive cell or on a MID 4460 substrate, e.g., a protein substrate, as determined in vivo or in vitro. In one embodiment, a MID 4460 activity is a direct activity, such as an association with a MID 4460 target molecule. A "target molecule" or "binding partner" is a molecule with which a MID 4460 protein binds or interacts in nature. In an exemplary embodiment, MID 4460 is a receptor and enzyme for a phosphorylated substrate. The binding of a ligand to the receptor portion of MID 4460 may regulate the phosphatase activity of the protein. The enzymatic portion may bind to a substrate containing a phosphorylated amino acid residue such as a tyrosine, threonine, or serine, and catalyze the hydrolysis of the phosphoester bond.

A MID 4460 activity can also be an indirect activity, e.g., a cellular signaling activity mediated by interaction of the MID 4460 protein with a MID 4460 receptor. Based on the above-described sequence structures and similarities to molecules of known function, the MID 4460 molecules of the present invention can have similar biological activities as tyrosine phosphatase family members. For example, the MID 4460 proteins of the present invention can have one or more of the following activities: (1) the ability to catalyze the hydrolysis of a phosphoester bond; (2) the ability to bind a ligand; (3) the ability to dephosphorylate a phosphorylated protein; (4) the ability to mediate signal tranduction; and (5) the ability to act as an adhesion molecule.

The MID 4460 molecules of the invention can modulate the activities of cells in tissues where they are expressed. For example, MID 4460 mRNA is expressed in liver, heart, colon, pancreas, brain, spleen, and small intestines. Accordingly, the MID 4460 molecules of the invention can act as therapeutic or diagnostic agents for cardiovascular, hepatic, gastrointestinal, or neurological disorders.

Thus, the MID 4460 molecules can act as novel diagnostic targets and therapeutic agents for controlling one or more cardiovascular or other tyrosine phosphatase disorders. As used herein, "tyrosine phosphatase disorders" are diseases or disorders whose pathogenesis is caused by, is related to, or is associated with aberrant or deficient tyrosine phosphatase protein function or expression. Examples of such disorders, e.g., tyrosine phosphatase-associated or other MID 4460-associated disorders, include but are not limited to, cellular proliferative and/or differentiative disorders, immune e.g., inflammatory, disorders, cardiovascular disorders, endothelial cell disorders, or liver disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

The MID 4460 molecules can be used to treat cardiovascular disorders in part because tyrosine phosphatase family members are found in the heart and liver. The MID 4460 may be used to affect the biosynthesis of lipid risk factors (e.g., HDL, LDL, triglycerides) associated with athersclerosis. As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also can include an endothelial cell disorder.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The MID 4460 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease, and Reed-Sternberg disease.

Aberrant expression and/or activity of MID 4460 molecules can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by MID 4460 molecules in bone cells, e.g. osteoclasts and osteoblasts, that can in turn result in bone formation and degeneration. For example, MID 4460 molecules can support different activities of bone resorbing osteoclasts such as the stimulation of differentiation of monocytes and mononuclear phagocytes into osteoclasts. Accordingly, MID 4460 molecules that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The MID 4460 nucleic acid and protein of the invention can be used to treat and/or diagnose a variety of immune, e.g., inflammatory, (e.g. respiratory inflammatory) disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, MID 4460 molecules can play an important role in the etiology of certain viral diseases, including but not limited to Hepatitis B, Hepatitis C, and Herpes Simplex Virus (HSV). Modulators of MID 4460 activity could be used to control viral diseases. The modulators can be used in the treatment and/or diagnosis of viral infected tissue or virus-associated tissue fibrosis, especially liver and liver fibrosis. Also, MID 4460 modulators can be used in the treatment and/or diagnosis of virus-associated carcinoma, especially hepatocellular cancer.

Additionally, MID 4460 can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields (1987) *Pain*, New York:McGraw-Hill); pain associated with musculoskeletal disorders, e.g., joint pain; tooth pain; headaches; pain associated with surgery; pain related to irritable bowel syndrome; or chest pain.

The MID 4460 protein, fragments thereof, and derivatives and other variants of the sequence in SEQ ID NO:2 thereof are collectively referred to as "polypeptides or proteins of the invention" or "MID 4460 polypeptides or proteins". Nucleic acid molecules encoding such polypeptides or proteins are collectively referred to as "nucleic acids of the invention" or "MID 4460 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, N.Y., 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a MID 4460 protein, preferably a mammalian MID 4460 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of MID 4460 protein having less than about 30%, 20%, 10% and more preferably 5% (by dry weight), of non-MID 4460 protein (also referred to herein as a "contaminating protein"), or of chemical precursors or non-MID 4460 chemicals. When the MID 4460 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of MID 4460 (e.g., the sequence of SEQ ID NO:1 or 3) without abolishing or more preferably, without substantially altering a biological activity, whereas an "essential" amino acid residue results in such a change. For example, amino acid residues that are conserved among the polypeptides of the present invention, e.g., those present in the protein tyrosine phosphatase or fibronectin domains, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a MID 4460 protein is preferably replaced with another amino acid residue from the same side chain family. Alternatively, in another embodiment, mutations can be introduced randomly along all or part of a MID 4460 coding sequence, such as by saturation mutagenesis, and the resultant mutants can be screened for MID 4460 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a MID 4460 protein includes a fragment of a MID 4460 protein which participates in an interaction between a MID 4460 molecule and a non-MID 4460 molecule. Biologically active portions of a MID 4460 protein include peptides comprising amino acid sequences sufficiently homologous to or derived from the amino acid sequence of the MID 4460 protein, e.g., the amino acid sequence shown in SEQ ID NO:2, which include fewer amino acids than the full length MID 4460 protein, and exhibit at least one activity of a MID 4460 protein. Typically, biologically active portions comprise a domain or motif with at least one activity of the MID 4460 protein, e.g., the ability to catalyze the hydrolysis of a phosphoester bond. A biologically active portion of a MID 4460 protein can be a polypeptide which is, for example, 10, 25, 50, 100, 200 or more amino acids in length. Biologically active portions of a MID 4460 protein can be used as targets for developing agents which modulate a MID 4460 mediated activity, e.g., the ability to catalyze the hydrolysis of a phosphoester bond.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the MID 4460 amino acid sequence of SEQ ID NO:2 having 1118 amino acid residues, at least 30%, preferably at least 40%, more preferably at least 50%, even more preferably at least 60%, and even more preferably at least 70%, 80%, or 90% amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215: 403–10. BLAST nucleotide searches can be performed with the NBLAST program, score=100, wordlength=12 to obtain nucleotide sequences homologous to MID 4460 nucleic acid molecules of the invention. BLAST protein searches can be performed with the XBLAST program, score=50, wordlength=3 to obtain amino acid sequences homologous to MID 4460 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov.

Particular MID 4460 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a MID 4460 polypeptide described herein, e.g., a full length MID 4460 protein or a fragment thereof, e.g., a biologically active portion of MID 4460 protein. Also included is a nucleic acid fragment suitable for use as a hybridization probe, which can be used, e.g., to identify a nucleic acid molecule encoding a polypeptide of the invention, MID 4460 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of this nucleotide sequence. In one embodiment, the nucleic acid molecule includes sequences encoding the human MID 4460 protein (i.e., "the coding region" of SEQ ID NO:1, as shown in SEQ ID NO:3), as well as 5' untranslated sequences (nucleotides 1 to 42 of SEQ ID NO:1) and 3' untranslated sequences (nucleotides 3399 to 3900 of SEQ ID NO:1). Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 846 to 1080 of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or 3, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

MID 4460 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a MID 4460 protein, e.g., an immunogenic or biologically active portion of a MID 4460 protein. A fragment can comprise those nucleotides of SEQ ID NO:1, which encode a protein tyrosine phosphatase domain or a fibronectin type III domain of human MID 4460. The nucleotide sequence determined from the cloning of the MID 4460 gene allows for the generation of probes and primers designed for use in identifying and/or cloning other MID 4460 family members, or fragments thereof, as well as MID 4460 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a MID 4460 nucleic acid fragment can include a sequence corresponding to a protein tyrosine phosphatase domain or a fibronectin type III domain, as described herein.

MID 4460 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a signal sequence from about amino acid 1 to 25 of SEQ ID NO:2; a N-terminal extracellular domain from about amino acid 1 to 754 or 26 to 754 of SEQ ID NO:2; a transmembrane domain from about amino acid 754 to 778 of SEQ ID NO:2; a C-terminal cytoplasmic domain from about amino acid 778 to 1118 of SEQ ID NO:2; a fibronectin type III domain from about amino acid 28 to 108, 119 to 201, 299 to 381, 388 to 469, 477 to 559, or 567 to 656 of SEQ ID NO:2; a protein-tyrosine phosphatase domain from about amino acid 846 to 1080, 977 to 1080, or 821 to 1083 of SEQ ID NO:2.

In another embodiment a set of primers is provided, e.g., primers suitable for use in a PCR, which can be used to amplify a selected region of a MID 4460 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a cytoplasmic domain from about amino acid 778 to 1118 of SEQ ID NO:2; a transmembrane domain from about amino acid 754 to 778 of SEQ ID NO:2; an extracellular domain from about amino acid 1 to 754 or 26 to 754 of SEQ ID NO:2; a mature protein from about amino acid 26 to 1118 of SEQ ID NO:2; a protein tyrosine phosphatase domain from about amino acid 821 to 1083 of SEQ ID NO:2; a protein tyrosine phosphatase domain from about amino acid 977 to 1080 of SEQ ID NO:2; a protein tyrosine phosphatase domain from about amino acid 846 to 1080 of SEQ ID NO:2; a fibronectin type III domain from about amino acid 30 to 109, 119 to 198, 299 to 378, 388 to 467, 477 to 556, or 567 to 657 of SEQ ID NO:2.

A nucleic acid fragment can encode an epitope bearing region of a polypeptide described herein.

A nucleic acid fragment encoding a "biologically active portion of a MID 4460 polypeptide" can be prepared by isolating a portion of the nucleotide sequence of SEQ ID NO:1 or 3, which encodes a polypeptide having a MID 4460 biological activity (e.g., the biological activities of the MID 4460 proteins are described herein), expressing the encoded portion of the MID 4460 protein (e.g., by recombinant expression in vitro) and assessing the activity of the encoded portion of the MID 4460 protein. For example, a nucleic acid fragment encoding a biologically active portion of MID 4460 includes a protein tyrosine phosphatase domain, e.g., amino acid residues about 846 to 1080 of SEQ ID NO:2. A nucleic acid fragment encoding a biologically active portion of a MID 4460 polypeptide, can comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900 or more nucleotides in length and hybridizes under stringent hybridization conditions to a nucleic acid molecule of SEQ ID NO:1 or SEQ ID NO:3.

MID 4460 Nucleic Acid Variants

The invention further encompasses nucleic acid molecules that differ from the nucleotide sequence shown in SEQ ID NO:1 or SEQ ID NO:3. Such differences can be due to degeneracy of the genetic code and result in a nucleic acid which encodes the same MID 4460 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10%, or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under stringent conditions, to the nucleotide sequence shown in SEQ ID NO 2 or a fragment of the sequence. Nucleic acid molecules corresponding to orthologs, homologs, and allelic variants of the MID 4460 cDNAs of the invention can further be isolated by mapping to the same chromosome or locus as the MID 4460 gene.

Preferred variants include those that are correlated with the ability to catalyze the hydrolysis of a phosphate ester bond of a substrate or the ability to bind a ligand.

Allelic variants of MID 4460, e.g., human MID 4460, include both functional and non-functional proteins. Functional allelic variants are naturally occurring amino acid sequence variants of the MID 4460 protein within a population that maintain the ability to catalyze the hydrolysis of a phosphate ester bond or to bind a ligand. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the MID 4460, e.g., human MID 4460, protein within a population that do not have the ability to catalyze the hydrolysis of a phosphate ester bond or bind a ligand. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other MID 4460 family members and, thus, which have a nucleotide sequence which differs from the MID 4460 sequences of SEQ ID NO:1 or SEQ ID NO:3 are intended to be within the scope of the invention.

Antisense Nucleic Acid Molecules, Ribozymes and Modified MID 4460 Nucleic Acid Molecules In another aspect, the invention features, an isolated nucleic acid molecule which is antisense to MID 4460. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire MID 4460 coding strand, or to only a portion thereof (e.g., the coding region of human MID 4460 corresponding to SEQ ID NO:3). In another embodiment, the antisense nucleic acid molecule is antisense to a "non-coding region" of the coding strand of a nucleotide sequence encoding MID 4460 (e.g., the 5' and 3' untranslated regions).

An antisense nucleic acid can be designed such that it is complementary to the entire coding region of MID 4460 mRNA, but more preferably is an oligonucleotide which is antisense to only a portion of the coding or noncoding region of MID 4460 mRNA. For example, the antisense oligonucleotide can be complementary to the region surrounding the translation start site of MID 4460 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a MID 4460 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a MID 4460-encoding nucleic acid can include one or more sequences complementary to the nucleotide sequence of a MID 4460 cDNA disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) *Nature* 334: 585–591). For example, a derivative of a Tetrahymena L-19 IVS RNA can be constructed in which the nucleotide sequence of the active site is complementary to the nucleotide sequence to be cleaved in a MID 4460-encoding mRNA. See, e.g., Cech et al. U.S. Pat. No. 4,987,071; and Cech et al. U.S. Pat. No. 5,116,742. Alternatively, MID 4460 mRNA can be used to select a catalytic RNA having a specific ribonuclease activity from a pool of RNA molecules. See, e.g., Bartel and Szostak (1993) *Science* 261: 1411–1418.

MID 4460 gene expression can be inhibited by targeting nucleotide sequences complementary to the regulatory region of the MID 4460 (e.g., the MID 4460 promoter and/or enhancers) to form triple helical structures that prevent transcription of the MID 4460 gene in target cells. See generally, Helene (1991) *Anticancer Drug Des.* 6:569–84; Helene (1992) *Ann. N.Y. Acad. Sci.* 660:27–36; and Maher (1992) *Bioassays* 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A MID 4460 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci.* 93: 14670–675.

PNAs of MID 4460 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of MID 4460 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup et al. (1996) supra)); or as probes or primers for DNA sequencing or hybridization (Hyrup et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a MID 4460 nucleic acid of the invention, two complementary regions one having a fluorophore and one a quencher such that the molecular beacon is useful for quantitating the presence of the MID 4460 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated MID 4460 Polypeptides

In another aspect, the invention features, an isolated MID 4460 protein, or fragment, e.g., a biologically active portion, for use as immunogens or antigens to raise or test (or more generally to bind) anti-MID 4460 antibodies. MID 4460 protein can be isolated from cells or tissue sources using standard protein purification techniques. MID 4460 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present in a native cell.

In a preferred embodiment, a MID 4460 polypeptide has one or more of the following characteristics:

it has the ability to catalyze the hydrolysis of a phosphate ester bond, bind a ligand, dephosphorylate the MID 4460 target protein, transduce a signal, elevate HDL levels, decrease LDL levels, and reduce atherosclerosis;

it has a molecular weight, e.g., a deduced molecular weight, preferably ignoring any contribution of post translational modifications, amino acid composition or other physical characteristic of a MID 4460 polypeptide, e.g., a polypeptide of SEQ ID NO:2;

it has an overall sequence similarity of at least 60%, preferably at least 70%, more preferably at least 80, 90, or 95%, with a polypeptide of SEQ ID NO:2;

it is expressed in at least the following human tissues and cell lines: at high levels in liver and colon, at medium levels in heart, pancreas, brain, spleen, and small intestines;

it has a protein tyrosine phosphatase domain which is preferably about 70%, 80%, 90% or 95% identical to amino acid residues about 846 to 1080 of SEQ ID NO:2;

it has a fibronectin type III domain which is preferably about 70%, 80%, 90% or 95% identical to amino acid residues about 28 to 108, 119 to 201, 299 to 381, 388 to 469, 477 to 559, or 567 to 656 of SEQ ID NO:2; and it has at least one, two, three, four, five, six, seven, eight, nine, ten, eleven, twelve, thirteen, fourteen, fifteen, sixteen, seventeen, preferably eighteen, and most preferably nineteen of the cysteines found in the amino acid sequence of the native protein.

In a preferred embodiment the MID 4460 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the protein-tyrosine phosphatase domain at about residues 846 to 1080 of SEQ ID NO:2; the fibronectin type III domain at about residues 28 to 108, 119 to 201, 299 to 381, 388 to 469, 477 to 559, or 567 to 656 of SEQ ID NO:2; the transmembrane domain at about residues 754 to 778 of SEQ ID NO:2; the extracellular domain at about residues 1 to 754 of SEQ ID NO:2; or the intracellular domain at about residues 778 to 1118 of SEQ ID NO:2. In another embodiment one or more differences are in the protein-tyrosine phosphatase domain at about residues 846 to 1080 of SEQ ID NO:2; the fibronectin type III domain at about residues 28 to 108, 119 to 201, 299 to 381, 388 to 469, 477 to 559, 567 to 656 of SEQ ID NO:2; the transmembrane domain at about residues 754 to 778 of SEQ ID NO:2; the extracellular domain at about residues 1 to 754 of SEQ ID NO:2; or the intracellular domain at about residues 778 to 1118 of SEQ ID NO:2.

Other embodiments include a protein that contains one or more changes in amino acid sequence, e.g., a change in an amino acid residue which is not essential for activity. Such MID 4460 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2.

A MID 4460 protein or fragment is provided which varies from the sequence of SEQ ID NO:2 in regions defined by amino acids about 1 to 846 or 1080 to 1118 by at least one but by less than 15, 10 or 5 amino acid residues in the protein or fragment but which does not differ from SEQ ID NO:2 in regions defined by amino acids about 846 to 1080. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a MID 4460 protein includes a protein-tyrosine phosphatase domain. Moreover, other biologically active portions, in which other regions of the protein are deleted, can be prepared by recombinant techniques and evaluated for one or more of the functional activities of a native MID 4460 protein.

In a preferred embodiment, the MID 4460 protein has an amino acid sequence shown in SEQ ID NO:2. In other embodiments, the MID 4460 protein is sufficiently or substantially identical to SEQ ID NO:2. In yet another embodiment, the MID 4460 protein is sufficiently or substantially identical to SEQ ID NO:2 and retains the functional activity of the protein of SEQ ID NO:2, as described in detail in the subsections above.

MID 4460 Chimeric or Fusion Proteins

In another aspect, the invention provides MID 4460 chimeric or fusion proteins. As used herein, a MID 4460 "chimeric protein" or "fusion protein" includes a MID 4460 polypeptide linked to a non-MID 4460 polypeptide. A "non-MID 4460 polypeptide" refers to a polypeptide having an amino acid sequence corresponding to a protein which is not substantially homologous to the MID 4460 protein, e.g., a protein which is different from the MID 4460 protein and which is derived from the same or a different organism. The MID 4460 polypeptide of the fusion protein can correspond to all or a portion e.g., a fragment described herein of a MID 4460 amino acid sequence. In a preferred embodiment, a MID 4460 fusion protein includes at least one (or two) biologically active portion of a MID 4460 protein. The non-MID 4460 polypeptide can be fused to the N-terminus or C-terminus of the MID 4460 polypeptide.

The fusion protein can include a moiety which has a high affinity for a ligand. For example, the fusion protein can be a GST-MID 4460 fusion protein in which the MID 4460 sequences are fused to the C-terminus of the GST sequences. Such fusion proteins can facilitate the purification of recombinant MID 4460. Alternatively, the fusion protein can be a MID 4460 protein containing a heterologous signal sequence at its N-terminus. In certain host cells (e.g., mammalian host cells), expression and/or secretion of MID 4460 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The MID 4460 fusion proteins of the invention can be incorporated into pharmaceutical compositions and administered to a subject in vivo. The MID 4460 fusion proteins can be used to affect the bioavailability of a MID 4460 substrate. MID 4460 fusion proteins can be useful therapeutically for the treatment of disorders caused by, for example, (i) aberrant modification or mutation of a gene encoding a MID 4460 protein; (ii) mis-regulation of the MID 4460 gene; and (iii) aberrant post-translational modification of a MID 4460 protein.

Moreover, the MID 4460-fusion proteins of the invention can be used as immunogens to produce anti-MID 4460 antibodies in a subject, to purify MID 4460 ligands and in screening assays to identify molecules which inhibit the interaction of MID 4460 with a MID 4460 substrate.

Expression vectors are commercially available that already encode a fusion moiety (e.g., a GST polypeptide). A MID 4460-encoding nucleic acid can be cloned into such an expression vector such that the fusion moiety is linked in frame to the MID 4460 protein.

Variants of MID 4460 Proteins

In another aspect, the invention also features a variant of a MID 4460 polypeptide, e.g., which functions as an agonist (mimetics) or as an antagonist. Variants of the MID 4460 proteins can be generated by mutagenesis, e.g., discrete point mutation, the insertion or deletion of sequences or the truncation of a MID 4460 protein. An agonist of the MID 4460 proteins can retain substantially the same, or a subset, of the biological activities of the naturally occurring form of a MID 4460 protein. An antagonist of a MID 4460 protein can inhibit one or more of the activities of the naturally occurring form of the MID 4460 protein by, for example, competitively modulating a MID 4460-mediated activity of a MID 4460 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the MID 4460 protein.

Variants of a MID 4460 protein can be identified by screening combinatorial libraries of mutants, e.g., truncation mutants, of a MID 4460 protein for agonist or antagonist activity.

Libraries of fragments e.g., N terminal, C terminal, or internal fragments, of a MID 4460 protein coding sequence can be used to generate a variegated population of fragments for screening and subsequent selection of variants of a MID 4460 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify MID 4460 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated MID 4460 library. For example, a library of expression vectors can be transfected into a cell line, e.g., a cell line, which ordinarily responds to MID 4460 in a substrate-dependent manner. The transfected cells are then contacted with MID 4460 and the effect of the expression of the mutant on signaling by the MID 4460 substrate can be detected, e.g., by measuring the hydrolysis of a phosphate ester bond in a substrate such as a peptide or protein. Plasmid DNA can then be recovered from the cells which score for inhibition, or alternatively, potentiation of signaling by the MID 4460 substrate, and the individual clones further characterized.

In another aspect, the invention features a method of making a MID 4460 polypeptide, e.g., a peptide having a non-wild type activity, e.g., an antagonist, agonist, or super agonist of a naturally occurring MID 4460 polypeptide, e.g., a naturally occurring MID 4460 polypeptide. The method includes altering the sequence of a MID 4460 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a MID 4460 polypeptide a biological activity of a naturally occurring MID 4460 polypeptide. The method includes altering the sequence, e.g., by substitution or deletion of one or more residues, of a MID 4460 polypeptide, e.g., altering the sequence of a non-conserved region, or a domain or residue described herein, and testing the altered polypeptide for the desired activity.

Anti-MID 4460 Antibodies

In another aspect, the invention provides an anti-MID 4460 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length MID 4460 protein or, antigenic peptide fragment of MID 4460 can be used as an immunogen or can be used to identify anti-MID 4460 antibodies made with other immunogens, e.g., cells, membrane preparations, and the like. The antigenic peptide of MID 4460 should include at least 8 amino acid residues of the amino acid sequence shown in SEQ ID NO:2 and encompasses an epitope of MID 4460. Preferably, the antigenic peptide includes at least 10 amino acid residues, more preferably at least 15 amino acid residues, even more preferably at least 20 amino acid residues, and most preferably at least 30 amino acid residues.

Fragments of MID 4460 which include residues about 65 to 85, from about 140 to 175, from about 190 to 225, from about 230 to 240, from about 250 to 265, from about 315 to 350, from about 365 to 395, from about 402 to 422, from about 420 to 435, from about 450 to 470, from about 480 to 488, from about 495 to 505, from about 510 to 525, from about 540 to 558, from about 561 to 580, from about 595 to 630, from about 700 to 715, from about 773 to 790, from about 800 to 818, from about 835 to 855, from about 921 to 945, from about 995 to 1015, and from about 1075 to 1118 of SEQ ID NO:2 can be used to make, e.g., used as immunogens or used to characterize the specificity of an antibody, antibodies against hydrophilic regions of the MID 4460 protein (see FIG. 2). Similarly, fragments of MID 4460 which include residues about 1 to 25, from about 85 to 100, from about 355 to 365, from about 710 to 720, from about 750 to 775, or about 1020 to 1040 of SEQ ID NO:2 can be used to make an antibody against a hydrophobic region of the MID 4460 protein; fragments of MID 4460 which include residues about 1 to 754, or a subset thereof, e.g. about residues 1 to 25, about residues 28 to 108, about residues 119 to 201, about residues 299 to 381, about residues 388 to 469, about residues 477 to 559, about residues 567 to 656, about residues 656 to 754 of SEQ ID NO:2 can be used to make an antibody against an extracellular region of the MID 4460 protein; fragments of MID 4460 which includes residues about 778 to 1118, about 846 to 1080, about 977 to 1080, or about 821 to 1083 of SEQ ID NO:2 can be used to make an antibody against an intracellular region of the MID 4460 protein; a fragment of MID 4460 which includes residues about 977 to 1080, about 821 to 1083, or about 846 to 1080 of SEQ ID NO:2 can be used to make an antibody against the protein-tyrosine phosphatase region of the MID 4460 protein; a fragment of MID 4460 which includes residues about 754 to 778 of SEQ ID NO:2 can be used to make an antibody against the transmembrane domain of the MID 4460 protein.

Antibodies reactive with, or specific or selective for, any of these regions, or other regions or domains described herein are provided.

Preferred epitopes encompassed by the antigenic peptide are regions of MID 4460 located on the surface of the protein, e.g., hydrophilic regions, as well as regions with high antigenicity. For example, an Emini surface probability analysis of the human MID 4460 protein sequence can be used to indicate the regions that have a particularly high probability of being localized to the surface of the MID 4460 protein and are thus likely to constitute surface residues useful for targeting antibody production.

In a preferred embodiment the antibody can bind to the extracellular portion of the MID 4460 protein, e.g., it can bind to a whole cell which expresses the MID 4460 protein. In another embodiment, the antibody binds an intracellular portion of the MID 4460 protein.

In a preferred embodiment the antibody binds an epitope on any domain or region on MID 4460 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559).

A humanized or complementarity determining region (CDR)-grafted antibody will have at least one or two, but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a MID 4460 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, (1987) *From Genes to Clones* (Verlagsgesellschaft, Weinheim, Germany). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison (1985) *Science* 229:1202–1207, by Oi et al. (1986) *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a MID 4460 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. (1986) *Nature* 321:552–525; Verhoeyan et al. (1988) *Science* 239:1534; Beidler et al. (1988) *J. Immunol.* 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585,089, the contents of which are hereby incorporated by reference. Other techniques for humanizing antibodies are described in Padlan et al. EP 519596 A1, published on Dec. 23, 1992.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

The anti-MID 4460 antibody can be a single chain antibody. A single-chain antibody (scFV) can be engineered as described in, for example, Colcher et al. (1999) *Ann. N Y Acad. Sci.* 880:263–80; and Reiter (1996) *Clin. Cancer Res.* 2:245–52. The single chain antibody can be dimerized or multimerized to generate multivalent antibodies having specificities for different epitopes of the same target MID 4460 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-MID 4460 antibody (e.g., monoclonal antibody) can be used to isolate MID 4460 by standard techniques, such as affinity chromatography or immunoprecipitation. Moreover, an anti-MID 4460 antibody can be used to detect MID 4460 protein (e.g., in a cellular lysate or cell supernatant) in order to evaluate the abundance and pattern of expression of the protein. Anti-MID 4460 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

In preferred embodiments, an antibody can be made by immunizing with a purified MID 4460 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native MID 4460 protein, only denatured or otherwise non-native MID 4460 protein, or which bind both, are within the invention. Antibodies with linear or conformational epitopes are within the invention. Conformational epitopes sometimes can be identified by identifying antibodies which bind to native but not denatured MID 4460 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a MID 4460 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., MID 4460 proteins, mutant forms of MID 4460 proteins, fusion proteins, and the like).

The recombinant expression vectors of the invention can be designed for expression of MID 4460 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in MID 4460 activity assays, (e.g., direct assays or competitive assays described in detail below), or to generate antibodies specific or selective for MID 4460 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman (1990) Gene Expression Technology: Methods in Enzymology 185, Academic Press, San Diego, Calif. 119–128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

The MID 4460 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al., (1986) Reviews—Trends in Genetics 1:1.

Another aspect the invention provides a host cell which includes a nucleic acid molecule described herein, e.g., a MID 4460 nucleic acid molecule within a recombinant expression vector or a MID 4460 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a MID 4460 protein can be expressed in bacterial cells such as E. coli, insect cells, yeast or mammalian cells (such as Chinese hamster ovary (CHO) cells or CV-1 origin, SV-40 (COS) cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a MID 4460 protein. Accordingly, the invention further provides methods for producing a MID 4460 protein using the host cells of the invention. In one embodiment, the method includes culturing the host cell of the invention (into which a recombinant expression vector encoding a MID 4460 protein has been introduced) in a suitable medium such that a MID 4460 protein is produced. In another embodiment, the method further includes isolating a MID 4460 protein from the medium or the host cell.

In another aspect, the invention features, a cell or purified preparation of cells which include a MID 4460 transgene, or which otherwise misexpress MID 4460. The cell preparation can consist of human or non-human cells, e.g., rodent cells, e.g., mouse or rat cells, rabbit cells, or pig cells. In preferred embodiments, the cell or cells include a MID 4460 transgene, e.g., a heterologous form of a MID 4460, e.g., a gene derived from humans (in the case of a non-human cell). The MID 4460 transgene can be misexpressed, e.g., overexpressed or underexpressed. In other preferred embodiments, the cell or cells include a gene which misexpresses an endogenous MID 4460, e.g., a gene the expression of which is disrupted, e.g., a knockout. Such cells can serve as a model for studying disorders which are related to mutated or misexpressed MID 4460 alleles or for use in drug screening.

In another aspect, the invention features, a human cell, e.g., a hematopoietic stem cell, transformed with nucleic acid which encodes a subject MID 4460 polypeptide.

Also provided are cells, preferably human cells, e.g., human hematopoietic or fibroblast cells, in which an endogenous MID 4460 is under the control of a regulatory sequence that does not normally control the expression of the endogenous MID 4460 gene. The expression characteristics of an endogenous gene within a cell, e.g., a cell line or microorganism, can be modified by inserting a heterologous DNA regulatory element into the genome of the cell such that the inserted regulatory element is operably linked to the endogenous MID 4460 gene. For example, an endogenous MID 4460 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a MID 4460 protein and for identifying and/or evaluating modulators of MID 4460 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous MID 4460 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a MID 4460 protein to particular cells. A transgenic founder animal can be identified based upon the presence of a MID 4460 transgene in its genome and/or expression of MID 4460 mRNA in tissues or cells of the animals. A transgenic founder animal can then be used to breed additional animals carrying the transgene. Moreover, transgenic animals carrying a transgene encoding a MID 4460 protein can further be bred to other transgenic animals carrying other transgenes.

MID 4460 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a MID 4460 protein (e.g., via a recombinant expression vector in a host cell in gene therapy applications), to detect a MID 4460 mRNA (e.g., in a biological sample) or a genetic alteration in a MID 4460 gene, and to modulate MID 4460 activity, as described further below. The MID 4460 proteins can be used to treat disorders characterized by insufficient or excessive production of a MID 4460 substrate or production of MID 4460 inhibitors. In addition, the MID 4460 proteins can be used to screen for naturally occurring MID 4460 substrates, to screen for drugs or compounds which modulate MID 4460 activity, as well as to treat disorders characterized by insufficient or excessive production of MID 4460 protein or production of MID 4460 protein forms which have decreased, aberrant or unwanted activity compared to MID 4460 wild type protein (e.g., aberrant or deficient phosphatase function or expression). Moreover, the anti-MID 4460 antibodies of the invention can be used to detect and isolate MID 4460 proteins, regulate the bioavailability of MID 4460 proteins, and modulate MID 4460 activity.

A method of evaluating a compound for the ability to interact with, e.g., bind, a subject MID 4460 polypeptide is provided. The method includes: contacting the compound with the subject MID 4460 polypeptide; and evaluating ability of the compound to interact with, e.g., to bind or form a complex with the subject MID 4460 polypeptide. This method can be performed in vitro, e.g., in a cell free system, or in vivo, e.g., in a two-hybrid interaction trap assay. This method can be used to identify naturally occurring molecules which interact with subject MID 4460 polypeptide. It can also be used to find natural or synthetic inhibitors of subject MID 4460 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to MID 4460 proteins, have a stimulatory or inhibitory effect on, for example, MID 4460 expression or MID 4460 activity, or have a stimulatory or inhibitory effect on, for example, the expression or activity of a MID 4460 substrate. Compounds thus identified can be used to modulate the activity of target gene products (e.g., MID 4460 genes) in a therapeutic protocol, to elaborate the biological function of the target gene product, or to identify compounds that disrupt normal target gene interactions.

In one embodiment, the invention provides assays for screening candidate or test compounds which are substrates of a MID 4460 protein or polypeptide or a biologically active portion thereof. In another embodiment, the invention provides assays for screening candidate or test compounds which bind to or modulate the activity of a MID 4460 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909–13; Erb et al. (1994) *Proc. Natl. Acad. Sci. USA* 91:11422–426; Zuckermann et al. (1994). *J. Med. Chem.* 37:2678–85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233–51.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner USP '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a MID 4460 protein or biologically active portion thereof is contacted with a test compound, and the ability of the test compound to modulate MID 4460 activity is determined. Determining the ability of the test compound to modulate MID 4460 activity can be accomplished by monitoring, for example, the hydrolysis of a phosphate ester of a substrate of MID 4460. The cell, for example, can be of mammalian origin, e.g., human.

The ability of the test compound to modulate MID 4460 binding to a compound, e.g., a MID 4460 substrate, or to bind to MID 4460 can also be evaluated. This can be accomplished, for example, by coupling the compound, e.g., the substrate, with a radioisotope or enzymatic label such that binding of the compound, e.g., the substrate, to MID 4460 can be determined by detecting the labeled compound, e.g., substrate, in a complex. Alternatively, MID 4460 could be coupled with a radioisotope or enzymatic label to monitor the ability of a test compound to modulate MID 4460 binding to a MID 4460 substrate in a complex. For example, compounds (e.g., MID 4460 substrates) can be labeled with $^{125}I$, $^{14}C$, $^{35}S$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a MID 4460 substrate) to interact with MID 4460 with or without the labeling of any of the interactants can be evaluated. For example, a microphysiometer can be used to detect the interaction of a compound with MID 4460 without the labeling of either the compound or the MID 4460. McConnell et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and MID 4460.

In yet another embodiment, a cell-free assay is provided in which a MID 4460 protein or biologically active portion thereof is contacted with a test compound and the ability of the test compound to bind to the MID 4460 protein or biologically active portion thereof is evaluated. Preferred biologically active portions of the MID 4460 proteins to be used in assays of the present invention include fragments which participate in interactions with non-MID 4460 molecules, e.g., fragments with high surface probability scores.

Soluble and/or membrane-bound forms of isolated proteins (e.g., MID 4460 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the MID 4460 protein to bind to a target molecule can be accomplished using real-time Biomolecular Interaction Analysis (BIA) (see, e.g., Sjolander and Urbaniczky (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either MID 4460, an anti-MID 4460 antibody or its target molecule to facilitate separation of complexed from uncomplexed forms of one or both of the proteins, as well as to accommodate automation of the assay. Binding of a test compound to a MID 4460 protein, or interaction of a MID 4460 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/MID 4460 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or MID 4460 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of MID 4460 binding or activity determined using standard techniques.

Other techniques for immobilizing either a MID 4460 protein or a target molecule on matrices include using conjugation of biotin and streptavidin. Biotinylated MID 4460 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with MID 4460 protein or target molecules but which do not interfere with binding of the MID 4460 protein to its target molecule. Such antibodies can be derivatized to the wells of the plate, and unbound target or MID 4460 protein trapped in the wells by antibody conjugation. Methods for detecting such complexes, in addition to those described above for the GST-immobilized complexes, include immunodetection of complexes using antibodies reactive with the MID 4460 protein or target molecule, as well as enzyme-linked assays which rely on detecting an enzymatic activity associated with the MID 4460 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18:284–7); chromatography (gel filtration chromatography, ion-exchange chromatography); electrophoresis (see, e.g., Ausubel et al., eds. (1999) *Current Protocols in Molecular Biology*, J. Wiley, New York.); and immunoprecipitation (see, for example, Ausubel et al., eds. (1999) *Current Protocols in Molecular Biology*, J. Wiley, New York). Such resins and chromatographic techniques are known to one skilled in the art (see, e.g., Heegaard (1998) *J Mol Recognit* 11:141–8; Hage and Tweed (1997) *J Chromatogr B Biomed Sci Appl.* 699:499–525). Further, fluorescence energy transfer can also be conveniently utilized, as described herein, to detect binding without further purification of the complex from solution.

In a preferred embodiment, the assay includes contacting the MID 4460 protein or biologically active portion thereof with a known compound which binds MID 4460 to form an assay mixture, contacting the assay mixture with a test compound, and determining the ability of the test compound to interact with a MID 4460 protein, wherein determining the ability of the test compound to interact with a MID 4460 protein includes determining the ability of the test compound to preferentially bind to MID 4460 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the MID 4460 genes herein identified. In an alternative embodiment, the invention provides methods for determining the ability of the test compound to modulate the activity of a MID 4460 protein through modulation of the activity of a downstream effector of a MID 4460 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the MID 4460 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with MID 4460 ("MID 4460-binding proteins" or "MID 4460-bp") and are involved in MID 4460 activity. Such MID 4460-bps can be activators or inhibitors of signals by the MID 4460 proteins or MID 4460 targets as, for example, downstream elements of a MID 4460-mediated signaling pathway.

The two-hybrid system is based on the modular nature of most transcription factors, which consist of separable DNA-binding and activation domains. Briefly, the assay utilizes two different DNA constructs. In one construct, the gene that codes for a MID 4460 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: MID 4460 protein can be the fused to the activator domain.) If the "bait" and the "prey" proteins are able to interact, in vivo, forming a MID 4460-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MID 4460 protein.

In another embodiment, modulators of MID 4460 expression are identified. For example, a cell or cell free mixture is contacted with a candidate compound and the expression of MID 4460 mRNA or protein evaluated relative to the level of expression of MID 4460 mRNA or protein in the absence of the candidate compound. When expression of MID 4460 mRNA or protein is greater in the presence of the candidate compound than in its absence, the candidate compound is identified as a stimulator of MID 4460 mRNA or protein expression. Alternatively, when expression of MID 4460 mRNA or protein is less (statistically significantly less) in the presence of the candidate compound than in its absence, the candidate compound is identified as an inhibitor of MID 4460 mRNA or protein expression. The level of MID 4460 mRNA or protein expression can be determined by methods described herein for detecting MID 4460 mRNA or protein.

In another aspect, the invention pertains to a combination of two or more of the assays described herein. For example, a modulating agent can be identified using a cell-based or a cell free assay, and the ability of the agent to modulate the activity of a MID 4460 protein can be confirmed in vivo, e.g., in an animal such as an animal model for aberrant or deficient phosphatase function or expression or for cardiovascular disease.

This invention further pertains to novel agents identified by the above-described screening assays. Accordingly, it is within the scope of this invention to further use an agent identified as described herein (e.g., a MID 4460 modulating agent, an antisense MID 4460 nucleic acid molecule, a MID 4460-specific antibody, or a MID 4460-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate MID 4460 with a disease; (ii) identify an individual from a minute biological sample (tissue typing); and (iii) aid in forensic identification of a biological sample. These applications are described in the subsections below.

Chromosome Mapping

The MID 4460 nucleotide sequences or portions thereof can be used to map the location of the MID 4460 genes on a chromosome. This process is called chromosome mapping. Chromosome mapping is useful in correlating the MID 4460 sequences with genes associated with disease.

Briefly, MID 4460 genes can be mapped to chromosomes by preparing PCR primers (preferably 15–25 bp in length) from the MID 4460 nucleotide sequences. These primers can then be used for PCR screening of somatic cell hybrids containing individual human chromosomes. Only those hybrids containing the human gene corresponding to the MID 4460 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919–924).

Other mapping strategies e.g., in situ hybridization (described in Fan et al. (1990) *Proc. Natl. Acad. Sci. USA*, 87:6223–27), pre-screening with labeled flow-sorted chromosomes, and pre-selection by hybridization to chromosome specific cDNA libraries can be used to map MID 4460 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature*, 325:783–787.

Moreover, differences in the DNA sequences between individuals affected and unaffected with a disease associated with the MID 4460 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

MID 4460 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272, 057).

Furthermore, the sequences of the present invention can also be used to determine the actual base-by-base DNA sequence of selected portions of an individual's genome. Thus, the MID 4460 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from MID 4460 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial MID 4460 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The MID 4460 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such MID 4460 probes can be used to identify tissue by species and/or by organ type.

In a similar fashion, these reagents, e.g., MID 4460 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes MID 4460.

Such disorders include, e.g., a disorder associated with the misexpression of MID 4460 gene; a disorder of the hepatic or cardiovascular system.

The method includes one or more of the following:

detecting, in a tissue of the subject, the presence or absence of a mutation which affects the expression of the MID 4460 gene, or detecting the presence or absence of a mutation in a region which controls the expression of the gene, e.g., a mutation in the 5' control region;

detecting, in a tissue of the subject, the presence or absence of a mutation which alters the structure of the MID 4460 gene;

detecting, in a tissue of the subject, the misexpression of the MID 4460 gene, at the mRNA level, e.g., detecting a non-wild type level of an mRNA;

detecting, in a tissue of the subject, the misexpression of the gene, at the protein level, e.g., detecting a non-wild type level of a MID 4460 polypeptide.

In preferred embodiments the method includes: ascertaining the existence of at least one of: a deletion of one or more nucleotides from the MID 4460 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the MID 4460 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the MID 4460 gene; the presence of a non-wild type splicing pattern of a messenger RNA transcript of the gene; or a non-wild type level of MID 4460.

Methods of the invention can be used prenatally or to determine if a subject's offspring will be at risk for a disorder.

In preferred embodiments the method includes determining the structure of a MID 4460 gene, an abnormal structure being indicative of risk for the disorder.

In preferred embodiments the method includes contacting a sample from the subject with an antibody to the MID 4460 protein or a nucleic acid, which hybridizes specifically with the gene. These and other embodiments are discussed below.

Diagnostic and Prognostic Assays

The presence, level, or absence of MID 4460 protein or nucleic acid in a biological sample can be evaluated by obtaining a biological sample from a test subject and contacting the biological sample with a compound or an agent capable of detecting MID 4460 protein or nucleic acid (e.g., mRNA, genomic DNA) that encodes MID 4460 protein such that the presence of MID 4460 protein or nucleic acid is detected in the biological sample. The term "biological sample" includes tissues, cells and biological fluids isolated from a subject, as well as tissues, cells and fluids present within a subject. A preferred biological sample is serum. The level of expression of the MID 4460 gene can be measured in a number of ways, including, but not limited to: measuring the mRNA encoded by the MID 4460 genes; measuring the amount of protein encoded by the MID 4460 genes; or measuring the activity of the protein encoded by the MID 4460 genes.

The level of mRNA corresponding to the MID 4460 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length MID 4460 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to MID 4460 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the MID 4460 genes.

The level of mRNA in a sample that is encoded by one of MID 4460 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189–193), self sustained sequence replication (Guatelli et al., (1990) Proc. Natl. Acad. Sci. USA 87:1874–1878), transcriptional amplification system (Kwoh et al., (1989), Proc. Natl. Acad. Sci. USA 86:1173–1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the MID 4460 gene being analyzed.

In another embodiment, the methods further contacting a control sample with a compound or agent capable of detecting MID 4460 mRNA, or genomic DNA, and comparing the presence of MID 4460 mRNA or genomic DNA in the control sample with the presence of MID 4460 mRNA or genomic DNA in the test sample.

A variety of methods can be used to determine the level of protein encoded by MID 4460. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect MID 4460 protein in a biological sample in vitro as well as in vivo. In vitro techniques for detection of MID 4460 protein include enzyme linked immunosorbent assays (ELISAs), immunoprecipitations, immunofluorescence, enzyme immunoassay (EIA), radioimmunoassay (RIA), and Western blot analysis. In vivo techniques for detection of MID 4460 protein include introducing into a subject a labeled anti-MID 4460 antibody. For example, the antibody can be labeled with a radioactive marker whose presence and location in a subject can be detected by standard imaging techniques.

In another embodiment, the methods further include contacting the control sample with a compound or agent capable of detecting MID 4460 protein, and comparing the presence of MID 4460 protein in the control sample with the presence of MID 4460 protein in the test sample.

The invention also includes kits for detecting the presence of MID 4460 in a biological sample. For example, the kit can include a compound or agent capable of detecting MID 4460 protein or mRNA in a biological sample; and a standard. The compound or agent can be packaged in a suitable container. The kit can further comprise instructions for using the kit to detect MID 4460 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted MID 4460 expression or activity. As used herein, the term "unwanted" includes an unwanted phenomenon involved in a biological response such as pain or deregulated cell proliferation.

In one embodiment, a disease or disorder associated with aberrant or unwanted MID 4460 expression or activity is identified. A test sample is obtained from a subject and MID 4460 protein or nucleic acid (e.g., mRNA or genomic DNA) is evaluated, wherein the level, e.g., the presence or absence, of MID 4460 protein or nucleic acid is diagnostic for a subject having or at risk of developing a disease or disorder associated with aberrant or unwanted MID 4460 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted MID 4460 expression or activity. For example, such methods can be used to determine whether a subject can be effectively treated with an agent for a cardiovascular disorder such as atherosclerosis, hypercholesterolemia, angina, coronary artery disease, stroke, etc.

The methods of the invention can also be used to detect genetic alterations in a MID 4460 gene, thereby determining if a subject with the altered gene is at risk for a disorder characterized by misregulation in MID 4460 protein activity or nucleic acid expression, such as a cardiovascular disorder. In preferred embodiments, the methods include detecting, in a sample from the subject, the presence or absence of a genetic alteration characterized by at least one of an alteration affecting the integrity of a gene encoding a MID 4460-protein, or the mis-expression of the MID 4460 gene. For example, such genetic alterations can be detected by ascertaining the existence of at least one of 1) a deletion of one or more nucleotides from a MID 4460 gene; 2) an addition of one or more nucleotides to a MID 4460 gene; 3) a substitution of one or more nucleotides of a MID 4460 gene, 4) a chromosomal rearrangement of a MID 4460 gene; 5) an alteration in the level of a messenger RNA transcript of a MID 4460 gene, 6) aberrant modification of a MID 4460 gene, such as of the methylation pattern of the genomic DNA, 7) the presence of a non-wild type splicing pattern of a messenger RNA transcript of a MID 4460 gene, 8) a non-wild type level of a MID 4460-protein, 9) allelic loss of a MID 4460 gene, and 10) inappropriate post-translational modification of a MID 4460-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the MID 4460-gene. This method can include the steps of collecting a sample of cells from a subject, isolating nucleic acid (e.g., genomic, mRNA or both) from the sample, contacting the nucleic acid sample with one or more primers which specifically hybridize to a MID 4460 gene under conditions such that hybridization and amplification of the MID 4460 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a MID 4460 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in MID 4460 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Human Mutation* 7: 244–255; Kozal et al. (1996) *Nature Medicine* 2: 753–759). For example, genetic mutations in MID 4460 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the MID 4460 gene and detect mutations by comparing the sequence of the sample MID 4460 with the corresponding wild-type (control) sequence. Automated sequencing procedures can be utilized when performing the diagnostic assays (Naeve et al. (1995) *Biotechniques* 19:448–53), including sequencing by mass spectrometry.

Other methods for detecting mutations in the MID 4460 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217: 286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in MID 4460 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in MID 4460 genes. For example, single strand conformation polymorphism (SSCP) can be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control MID 4460 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification can also be performed using Taq ligase for amplification (Barany (1991) *Proc. Natl. Acad. Sci USA* 88:189–93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a MID 4460 gene.

Use of MID 4460 Molecules as Surrogate Markers

The MID 4460 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the MID 4460 molecules of the invention can be detected, and can be correlated with one or more biological states in vivo. For example, the MID 4460 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The MID 4460 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a MID 4460 marker) transcription or expression, the amplified marker can be in a quantity which is more readily detectable than the drug itself. Also, the marker can be more easily detected due to the nature of the marker itself; for example, using the methods described herein, anti-MID 4460 antibodies can be employed in an immune-based detection system for a MID 4460 protein marker, or MID 4460-specific radiolabeled probes can be used to detect a MID 4460 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am. J. Health-Syst. Pharm.* 56 Suppl. 3: S16–S20.

The MID 4460 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., MID 4460 protein or RNA) for specific tumor markers in a subject, a drug or course of treatment can be selected that is optimized for the treatment of the specific tumor likely to be present in the subject. Similarly, the presence or absence of a specific sequence mutation in MID 4460 DNA can correlate with a MID 4460 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-MID 4460 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody, unconjugated or conjugated as described herein, can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted MID 4460 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the MID 4460 molecules of the present invention or MID 4460 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted MID 4460 expression or activity, by administering to the subject a MID 4460 or an agent which modulates MID 4460 expression or at least one MID 4460 activity. Subjects at risk for a disease which is caused or contributed to by aberrant or unwanted MID 4460 expression or activity can be identified by, for example, any or a combination of diagnostic or prognostic assays as described herein. Administration of a prophylactic agent can occur prior to the manifestation of symptoms characteristic of the MID 4460 aberrance, such that a disease or disorder is prevented or, alternatively, delayed in its progression. Depending on the type of MID 4460 aberrance, for example, a MID 4460, MID 4460 agonist or MID 4460 antagonist agent can be used for treating the subject. The appropriate agent can be determined based on screening assays described herein.

It is possible that some MID 4460 disorders can be caused, at least in part, by an abnormal level of gene product, or by the presence of a gene product exhibiting abnormal activity. As such, the reduction in the level and/or activity of such gene products would bring about the amelioration of disorder symptoms.

The MID 4460 molecules can act as novel diagnostic targets and therapeutic agents for controlling one or more of cardiovascular disorders, and liver disorders, all of which are described above. The molecules of the invention also can act as novel diagnostic targets and therapeutic agents for controlling one or more of cellular proliferative and/or differentiative disorders, disorders associated with bone metabolism, immune, e.g., inflammatory, disorders, endothelial cell disorders, viral diseases, pain disorders and metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The MID 4460 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) Crit Rev. in Oncol./Hemotol. 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Aberrant expression and/or activity of MID 4460 molecules can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by MID 4460 molecules in bone cells, e.g. osteoclasts and osteoblasts, that can in turn result in bone formation and degeneration. For example, MID 4460 molecules can support different activities of bone resorbing osteoclasts such as the stimulation of differentiation of monocytes and mononuclear phagocytes into osteoclasts. Accordingly, MID 4460 molecules that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The MID 4460 nucleic acid and protein of the invention can be used to treat and/or diagnose a variety of immune, e.g., inflammatory (e.g. respiratory inflammatory) disorders. Examples immune and inflammatory disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus, embolus, or plaque. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, coronary artery disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also can include an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, MID 4460 molecules can play an important role in the etiology of certain viral diseases, including but not limited to Hepatitis B, Hepatitis C and Herpes Simplex Virus (HSV). Modulators of MID 4460 activity could be used to control viral diseases. The modulators can be used in the treatment and/or diagnosis of viral infected tissue or virus-associated tissue fibrosis, especially liver and liver fibrosis. Also, MID 4460 modulators can be used in the treatment and/or diagnosis of virus-associated carcinoma, especially hepatocellular cancer.

Additionally, MID 4460 can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain,* New York:McGraw-Hill); pain associated with musculoskeletal disorders, e.g., joint pain; tooth pain; headaches; pain associated with surgery; pain related to irritable bowel syndrome; or chest pain.

As discussed, successful treatment of MID 4460 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of MID 4460 disorders.

Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by MID 4460 expression is through the use of aptamer molecules specific for MID 4460 protein. Aptamers are nucleic acid molecules having a tertiary structure which permits them to specifically or selectively bind to protein ligands (see, e.g., Osborne et al. (1997) *Curr. Opin. Chem Biol.* 1: 5–9; and Patel (1997) *Curr Opin Chem Biol* 1:32–46). Since nucleic acid molecules can in many cases be more conveniently introduced into target cells than therapeutic protein molecules can be, aptamers offer a method by which MID 4460 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of MID 4460 disorders. For a description of antibodies, see the Antibody section above.

In circumstances wherein injection of an animal or a human subject with a MID 4460 protein or epitope for stimulating antibody production is harmful to the subject, it is possible to generate an immune response against MID 4460 through the use of anti-idiotypic antibodies (see, for example, Herlyn (1999) *Ann Med* 31:66–78; and Bhattacharya-Chatterjee and Foon (1998) *Cancer Treat Res.* 94:51–68). If an anti-idiotypic antibody is introduced into a mammal or human subject, it should stimulate the production of anti-anti-idiotypic antibodies, which should be specific to the MID 4460 protein. Vaccines directed to a disease characterized by MID 4460 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate MID 4460 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate MID 4460 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89–94 and in Shea (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645–647. Through the use of isotope-labeling, the "free" concentration of compound which modulates the expression or activity of MID 4460 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al (1995) *Analytical Chemistry* 67:2142–2144.

Another aspect of the invention pertains to methods of modulating MID 4460 expression or activity for therapeutic purposes. Accordingly, in an exemplary embodiment, the modulatory method of the invention involves contacting a cell with a MID 4460 or agent that modulates one or more of the activities of MID 4460 protein activity associated with the cell. An agent that modulates MID 4460 protein activity can be an agent as described herein, such as a nucleic acid or a protein, a naturally-occurring target molecule of a MID 4460 protein (e.g., a MID 4460 substrate or receptor), a MID 4460 antibody, a MID 4460 agonist or antagonist, a peptidomimetic of a MID 4460 agonist or antagonist, or other small molecule.

In one embodiment, the agent stimulates one or MID 4460 activities. Examples of such stimulatory agents include active MID 4460 protein and a nucleic acid molecule encoding MID 4460. In another embodiment, the agent inhibits one or more MID 4460 activities. Examples of such inhibitory agents include antisense MID 4460 nucleic acid molecules, anti-MID 4460 antibodies, and MID 4460 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a MID 4460 protein or nucleic acid molecule. In one embodiment, the method involves administering an agent (e.g., an agent identified by a screening assay described herein), or combination of agents that modulates (e.g., up regulates or down regulates) MID 4460 expression or activity. In another embodiment, the method involves administering a MID 4460 protein or nucleic acid molecule as therapy to compensate for reduced, aberrant, or unwanted MID 4460 expression or activity.

Stimulation of MID 4460 activity is desirable in situations in which MID 4460 is abnormally downregulated and/or in which increased MID 4460 activity is likely to have a beneficial effect. For example, stimulation of MID 4460 activity is desirable in situations in which a MID 4460 is downregulated and/or in which increased MID 4460 activity is likely to have a beneficial effect. Likewise, inhibition of MID 4460 activity is desirable in situations in which MID 4460 is abnormally upregulated and/or in which decreased MID 4460 activity is likely to have a beneficial effect.

Pharmacogenomics

The MID 4460 molecules of the present invention, as well as agents, or modulators which have a stimulatory or inhibitory effect on MID 4460 activity (e.g., MID 4460 gene expression) as identified by a screening assay described herein can be administered to individuals to treat (prophylactically or therapeutically) MID 4460-associated disorders (e.g., aberrant or deficient phosphatase function or expression or cardiovascular disorder) associated with aberrant or unwanted MID 4460 activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a MID 4460 molecule or MID 4460 modulator as well as tailoring the dosage and/or therapeutic regimen of treatment with a MID 4460 molecule or MID 4460 modulator.

Pharmacogenomics deals with clinically significant hereditary variations in the response to drugs due to altered drug disposition and abnormal action in affected persons. See, for example, Eichelbaum et al. (1996) *Clin. Exp. Pharmacol. Physiol.* 23:983–985 and Linder et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a MID 4460 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a MID 4460 molecule or MID 4460 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a MID 4460 molecule or MID 4460 modulator, such as a modulator identified by one of the exemplary screening assays described herein.

The present invention further provides methods for identifying new agents, or combinations, that are based on identifying agents that modulate the activity of one or more of the gene products encoded by one or more of the MID 4460 genes of the present invention, wherein these products can be associated with resistance of the cells to a therapeutic agent. Specifically, the activity of the proteins encoded by the MID 4460 genes of the present invention can be used as a basis for identifying agents for overcoming agent resistance. By blocking the activity of one or more of the resistance proteins, target cells, e.g., human cells, will become sensitive to treatment with an agent to which the unmodified target cells were resistant.

Monitoring the influence of agents (e.g., drugs) on the expression or activity of a MID 4460 protein can be applied in clinical trials. For example, the effectiveness of an agent determined by a screening assay as described herein to increase MID 4460 gene expression, protein levels, or upregulate MID 4460 activity, can be monitored in clinical trials of subjects exhibiting decreased MID 4460 gene expression, protein levels, or downregulated MID 4460 activity. Alternatively, the effectiveness of an agent determined by a screening assay to decrease MID 4460 gene expression, protein levels, or downregulate MID 4460 activity, can be monitored in clinical trials of subjects exhibiting increased MID 4460 gene expression, protein levels, or upregulated MID 4460 activity. In such clinical trials, the expression or activity of a MID 4460 gene, and preferably, other genes that have been implicated in, for example, a tyrosine phosphatase-associated or another MID 4460-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses MID 4460 or from a cell or subject in which a MID 4460 mediated response has been elicited; contacting the array with a MID 4460 nucleic acid (preferably purified), a MID 4460 polypeptide (preferably purified), or an anti-MID 4460 antibody, and thereby evaluating the plurality of capture probes. Binding, e.g., in the case of a nucleic acid, hybridization with a capture probe at an address of the plurality, is detected, e.g., by a signal generated from a label attached to the MID 4460 nucleic acid, polypeptide, or antibody.

The capture probes can be a set of nucleic acids from a selected sample, e.g., a sample of nucleic acids derived from a control or non-stimulated tissue or cell.

The method can include contacting the MID 4460 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of MID 4460. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing MID 4460, e.g., analyzing structure, function, or relatedness to other nucleic acid or amino acid sequences. The method includes: providing a MID 4460 nucleic acid or amino acid sequence; comparing the MID 4460 sequence with one or more preferably a plurality of sequences from a collection of sequences, e.g., a nucleic acid or protein sequence database; to thereby analyze MID 4460.

The method can include evaluating the sequence identity between a MID 4460 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of MID 4460. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of MID 4460 molecules are provided in a variety of mediums to facilitate use thereof. A sequence can be provided as a manufacture, other than an isolated nucleic acid or amino acid molecule, which contains a MID 4460 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A MID 4460 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon MID 4460 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the MID 4460 sequence information.

A variety of data storage structures are available to a skilled artisan for creating a computer readable medium having recorded thereon a MID 4460 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the MID 4460 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a tyrosine phosphatase-associated or another MID 4460-associated disease or disorder or a pre-disposition to a tyrosine phosphatase-associated or another MID 4460-associated disease or disorder, wherein the method comprises the steps of determining MID 4460 sequence information associated with the subject and based on the MID 4460 sequence information, determining whether the subject has a tyrosine phosphatase-associated or another MID 4460-associated disease or disorder and/or recommending a particular treatment for the disease, disorder, or pre-disease condition.

The present invention further provides in an electronic system and/or in a network, a method for determining whether a subject has a tyrosine phosphatase-associated or another MID 4460-associated disease or disorder or a pre-disposition to a disease associated with MID 4460, wherein the method comprises the steps of determining MID 4460 sequence information associated with the subject, and based on the MID 4460 sequence information, determining whether the subject has a tyrosine phosphatase-associated or another MID 4460-associated disease or disorder or a pre-disposition to a tyrosine phosphatase-associated or another MID 4460-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a tyrosine phosphatase-associated or another MID 4460-associated disease or disorder or a pre-disposition to a tyrosine phosphatase-associated or another MID 4460-associated disease or disorder, said method comprising the steps of receiving MID 4460 sequence information from the subject and/or information related thereto, receiving phenotypic information associated with the subject, acquiring information from the network corresponding to MID 4460 and/or corresponding to a tyrosine phosphatase-associated or another MID 4460-associated disease or disorder, and based on one or more of the phenotypic information, the MID 4460 information (e.g., sequence information and/or information related thereto), and the acquired information, determining whether the subject has a tyrosine phosphatase-associated or another MID 4460-associated disease or disorder or a pre-disposition to a tyrosine phosphatase-associated or another MID 4460-associated disease or disorder. The method may further comprise the step of recommending a particular treatment for the disease, disorder, or pre-disease condition.

The present invention also provides a business method for determining whether a subject has a tyrosine phosphatase-associated or another MID 4460-associated disease or disorder or a pre-disposition to a tyrosine phosphatase-associated or another MID 4460-associated disease or disorder, said method comprising the steps of receiving information related to MID 4460 (e.g., sequence information and/or information related thereto), receiving phenotypic information associated with the subject, acquiring information from the network related to MID 4460 and/or related to a tyrosine phosphatase-associated or another MID 4460-associated disease or disorder, and based on one or more of the phenotypic information, the MID 4460 information, and the acquired information, determining whether the subject has a tyrosine phosphatase-associated or another MID 4460-associated disease or disorder or a pre-disposition to a tyrosine phosphatase-associated or another MID 4460-associated disease or disorder. The method may further comprise the step of recommending a particular treatment for the disease, disorder, or pre-disease condition.

The invention also includes an array comprising a MID 4460 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be MID 4460. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a tyrosine phosphatase-associated or another MID 4460-associated disease or disorder, progression of tyrosine phosphatase-associated or another MID 4460-associated disease or disorder, and processes, such a cellular transformation associated with the tyrosine phosphatase-associated or another MID 4460-associated disease or disorder.

The array is also useful for ascertaining the effect of the expression of a gene on the expression of other genes in the same cell or in different cells (e.g., acertaining the effect of MID 4460 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including MID 4460) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a MID 4460 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a MID 4460 sequence, or record, in computer readable form; comparing a second sequence to the MID 4460 sequence; thereby analyzing a sequence. Comparison can include comparing to sequences for sequence identity or determining if one sequence is included within the other, e.g., determining if the MID 4460 sequence includes a sequence being compared. In a preferred embodiment the MID 4460 or second sequence is stored on a first computer, e.g., at a first site and the comparison is performed, read, or recorded on a second computer, e.g., at a second site. E.g., the MID 4460 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

This invention is further illustrated by the following exemplification, which should not be construed as limiting.

EXEMPLIFICATION

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SuperScript™ Choice System following the manufacturer's instructions (Gibco-BRL). A negative control of RNA without reverse transcriptase was mock reverse transcribed for each RNA sample.

Human MID 4460 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human MID 4460 gene. Each human MID 4460 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2 microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human MID 4460 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human MID 4460 gene is normalized by subtracting the Ct value of the β-2 microglobulin gene to obtain a $_\Delta Ct$ value using the following formula: $_\Delta Ct = Ct_{human\ 59914\ and\ 59921} - Ct_{\beta-2\ microglobulin}$. Expression is then calibrated against a cDNA sample showing a comparatively low level of expression of the human MID 4460 gene. The $_\Delta Ct$ value for the calibrator sample is then subtracted from $_\Delta Ct$ for each tissue sample according to the following formula: $_{\Delta\Delta}Ct = _\Delta Ct_{sample} - _\Delta Ct_{calibrator}$. Relative expression is then calculated using the arithmetic formula given by $2^{-\Delta\Delta Ct}$. Expression of the target human MID 4460 gene in each of the tissues tested is then graphically represented as discussed in more detail below.

The results indicate significant MID 4460 expression in heart, pancreas, brain, colon, liver, spleen, and small intestine (see Tables below).

| Tissue | Expression |
|---|---|
| Phase 1.4.3 Expression of 4460.1 with beta2 | |
| Artery, normal | 0.165 |
| Vein, normal | 0 |
| Aortic SMC Early | 0.8327 |
| Coronary SMC | 1.1694 |
| Static HUVEC | 0.1216 |
| Shear HUVEC | 0.4766 |
| Heart, normal | 3.3538 |
| Heart, CHF | 0.5609 |
| Kidney | 0.2155 |
| Skeletal Muscle | 0.1524 |
| Adipose, normal | 0.0554 |
| Pancreas | 4.03 |
| Primary osteoblasts | 0 |
| Osteoclasts (diff.) | 0 |
| Skin normal | 0.0837 |
| Spinal cord, normal | 6.9441 |
| Brain, cortex normal | 7.0167 |
| Brain, hypothalamus | 5.9208 |
| Nerve | 0.0845 |
| DRG (Dorsal root ganglion) | 1.9196 |
| Resting PBMC | 0 |
| Glioblastoma | 0.2728 |
| Breast, normal | 0.6288 |
| Breast, tumor | 0.2125 |
| Ovary, normal | 0.4832 |
| Ovary, tumor | 0.1078 |
| Prostate, normal | 0.1393 |
| Prostate, tumor | 0.2358 |
| Epithelial cell (Prostate) | 1.0251 |
| Colon, normal | 14.885 |
| Colon, tumor | 24.7745 |
| Lung, normal | 0.0242 |
| Lung, tumor | 4.0721 |
| Lung, COPD | 0.0517 |
| Colon, IBD | 12.5602 |
| Liver, normal | 5.6796 |
| Liver, fibrosis | 9.585 |
| Dermal cells-fibroblasts | 0.1139 |
| Spleen, normal | 6.8723 |
| Tonsil, normal | 0.0236 |
| Lymph node | 0.0135 |
| Small Intestine | 4.8426 |
| Skin, decubitus | 0 |
| Synovium | 0.1336 |
| BM-MNC (Bone marrow) | 0.0027 |

| Tissue | Expression |
|---|---|
| Activated PBMC | 0 |
| 4460.1 Expression in Human Liver Panel | |
| PIT 278/Heart | 10.0616 |
| PIT 351/Kidney | 0.6647 |
| PIT 915/Skeletal Muscle | 0.7769 |
| NDR 63/Liver/Normal | 17.9484 |
| NDR 242/Liver/Normal | 8.0321 |
| PIT 260/Liver/Normal | 9.8545 |
| CHT 756/Liver/Normal | 7.9491 |
| MPI 146/Liver/Normal | 11.164 |
| CHT 902/Liver/Normal | 6.6843 |
| CHT 1679/Liver/Normal | 5.9826 |
| CHT 1420/Liver/Normal | 9.0054 |
| CHT 339/Liver/Normal | 7.6783 |
| CHT 1237/Liver/Normal | 3.6447 |
| PIT 45/Liver/Diseased | 10.0268 |
| PIT 292/Liver/Diseased | 22.8763 |
| CLN 784/Liver/Diseased | 3.9608 |
| NDR 752/Liver/Diseased | 11.0103 |

The contents of all references, patents and published patent applications cited throughout this application are incorporated herein by reference.

Equivalents

Those skilled in the art will recognize, or be able to ascertain using no more than routine experimentation, many equivalents to the specific embodiments of the invention described herein.

What is claimed is:

1. A method for identifying a candidate compound capable of treating a cardiovascular disorder, comprising
   combining a compound to be tested with a sample comprising a polypeptide
   comprising the amino acid sequence of SEQ ID NO:2, wherein the polypeptide has phosphatase activity under conditions suitable for the compound to modulate the activity of the polypeptide;
   ii) assaying the ability of the compound to modulate the activity of the polypeptide;
   iii) administering the compound identified to an animal, wherein the animal is an animal model for cardiovascular disorders; and
   iv) determining whether the compound modulates symptoms associated with cardiovascular disorders in the animal model;
thereby identifying a compound capable of treating a cardiovascular disorder.

2. The method of claim 1, wherein the compound is selected from the group consisting of a small organic molecule, a peptide and an antibody.

3. The method of claim 1, wherein the polypeptide further comprises heterologous sequences.

4. The method of claim 1, wherein the cardiovascular disorder is atherosclerosis.

5. The method of claim 1, wherein the sample is an isolated polypeptide or a cell comprising the polypeptide.

6. The method of claim 5, wherein the cell is a cell derived from heart tissue.

7. The method of claim 1, wherein the activity of the polypeptide is phosphatase activity.

8. A method for identifying a candidate compound capable of treating a cardiovascular disorder, comprising
   combining a compound to be tested with a sample comprising a polypeptide
   comprising the amino acid sequence of SEQ ID NO:2 under conditions suitable for the compound to modulate the activity of the polypeptide;
   ii) assaying the ability of the compound to modulate the activity of the polypeptide; and
   iii) administering the compound identified to an animal, wherein the animal is an animal model for cardiovascular disorders; and
   iv) determining whether the compound modulates symptoms associated with cardiovascular disorders in the animal model;
thereby identifying a compound capable of treating a cardiovascular disorder.

9. The method of claim 8, wherein the compound is selected from the group consisting of a small organic molecule, a peptide and an antibody.

10. The method of claim 8, wherein the polypeptide further comprises heterologous sequences.

11. The method of claim 8, wherein the cardiovascular disorder is atherosclerosis.

12. The method of claim 8, wherein the sample is an isolated polypeptide or a cell comprising the polypeptide.

13. The method of claim 12, wherein the cell is a cell derived from heart tissue.

14. The method of claim 8, wherein the activity of the polypeptide is phosphatase activity.

* * * * *

SEQUENCE LISTING

<160> NUMBER OF SEQ ID NOS: 11

<210> SEQ ID NO 1
<211> LENGTH: 3900
<212> TYPE: DNA
<213> ORGANISM: Homo sapiens

<400> SEQUENCE: 1

```
ctaggcctgg gactcctggg tccccggcag tgtctggagg catggctggg gctggcgggg      60
gcctcgggt  ctgggggaac  ctggtgctgc  tgggcctgtg  cagctggaca  ggggccaggg    120
cgcctgcccc caacccaggg aggaacctga cagtggagac tcagaccacc agctccatct     180
ccctgagctg ggaggtcccc gatggcctag actcacagaa ctccaactac tgggttcagt     240
gtactggaga cggcggcaca acagagactc gaaacacaac agccaccaac gtcaccgtgg     300
atggccttgg acccgggtca ttgtatacgt gttctgtgtg ggtggagaaa gacggagtaa     360
atagctctgt ggggactgtc actactgcca cagctcccaa cccagtgagg aacctgagag     420
tggaggctca gaccaacagc tccatcgccc tgacctggga ggtccccgac ggcccagacc     480
cacagaactc cacctacggg gttgagtaca ctggagatgg tggcagagca gggactcgaa     540
gcacagcaca cactaacatc accgtggatg gacttgaacc cgggtgtttg tatgcgtttt     600
ccatgtgggt gggaaagaat ggaatcaaca gctcccggga gactcgaaat gccaccacag     660
ctcacaaccc agtgaggaaa cctgagagtg gaggctcaga ccaccagctc catctccctg     720
agctgggagg tccccgatgg cacagaccca cagaactcga cctactgcgt acgagtgcac     780
tggagatggt ggcagaacag agactcgaaa cacaacagac accagagtca ccagtggatg     840
gccttggacc cgggtcattg tatacgtgtt ctgtgtgggt ggagaaagac ggagtaaata     900
gctcctcgtg gagattggta actagtacca cagctcccaa cccagtgaga aacctgacag     960
tggaggctca gaccaacagc tccatcgccc tgacctggga ggtccccgat ggcccagacc    1020
cacagaactc cacctacggg gttgagtaca ctggagatgg tggcagagca gggactcgaa    1080
gcacagcaca caccaacatc accgtggata gacttgaacc cgggtgtttg tatgtgtttt    1140
ccgtgtgggt gggaagaat ggaatcaaca gctcccggga gactcgaaat gccaccacag     1200
cccccaaccc agtgagaaac ctccatatgg agactcagac caacagctcc atcgccctat    1260
```

```
gctgggaagt ccccgatggc ccatacctc aggactacac ctactgggta gggtacactg    1320
gagacggtgg tggcacagag acccgaaaca caacaaatac cagtgtgaca gctgagagac    1380
ttgagcccgg aaccttgtac acattctctg tatgggcaga aaaaaatgga gcacgtggct    1440
ccaggcagaa tgtcagcatc tccacagtcc caacgcagt gacaagcctc agcaagcagg    1500
actggaccaa cagcaccatt gctttgcgct ggacagctcc ccagggccca ggccagtctt    1560
cctacagcta ctgggtctca tgggtcaggg aaggcatgac tgaccccagg acccaaagca    1620
cctcaggtac tgacatcacc ctaaaggaac tggaagctgg cagcctgtac cacctcaccg    1680
tctgggccga gaggaatgag gtcagaggct ataacagcac cctcactgca gccactgctc    1740
ccaatgaggt cacagatctc cagaatgaaa ctcagactaa gaactcagtc atgctgtggt    1800
ggaaggcccc tggagacccc cactctcagt tgtacgtata ctgggtccag tgggccagca    1860
agggacatcc ccggaggggg caagatcccc aagcgaattg ggtcaaccag accagcagga    1920
ccaatgagac gtggtacaaa gtggaggccc tggaacccgg gacgttgtac aatttcaccg    1980
tgtgggcaga gaggaatgac gtagccagtt ccacgcagag cctctgtgcg tccacatacc    2040
cagacacagt caccatcact tcctgtgtca gcacctcagc gggctatgga gtcaacttga    2100
tctggtcctg cccccaggga ggctacgagg cctttgagtt ggaggtggga ggacagcggg    2160
gctcccagga cagatcttca tgtggggagg ctgtgtctgt gttgggtctc gggccggctc    2220
ggtcctaccc agccaccatc acgaccatct gggacggaat gaaggtcgtg tctcactctg    2280
tggtctgcca caccgagagt gcaggggtca ttgccgagc ctttgtgggc atcctcctgt    2340
ttctcatcct cgtgggcctg ctgatttct cctgaagag gaggaataag aagaagcagc    2400
agaaaccaga actcagggat ctggtctta gctccccagg ggacatccca gctgaagact    2460
tcgctgacca cgtcaggaag aatgagaggg acagcaactg tggttttgca gacgagtacc    2520
agcaactctc cctggtgggc cacagccagt ctcagatggt ggcttcggct tcagagaaca    2580
acgccaagaa ccgctacaga aatgtgctgc cctatgactg gtcccgggtg ccctgaagc    2640 ccatccatga ggagccaggc tctgactaca tcaatgccag cttcatgccc ggtctctgga    2700
gcccccagga gttcattgca cccagggtc ccctgccaca gacagtgggt gacttctggc    2760
gcctggtgtg ggaacagcag agccacaccc tggtcatgct gaccaactgc atggaggccg    2820
gccgggtgaa gtgtgagcat tactggcctc tggactcgca gccctgcacc catgggcacc    2880
tgcgggtaac cctggtaggt gaggaagtga tggagaactg gacggtgcgg gaactgctgc    2940
tcctccaggt ggaggagcag aagacactgt ctgtgcgcca attccactac caggcctggc    3000
cggatcacgg cgttccctcc tccccagaca ccttgctggc tttctggagg atgcttcggc    3060
agtggctgga tcagaccatg gagggaggcc cacccattgt gcactgcagt gctggcgtgg    3120
gtcgcacagg aaccctcatt gccctggacg tcctgctccg gcagctgcag tccgagggtc    3180
tccttgggcc cttcagcttt gtaaggaaga tgagagagag tcggccgttg atggtgcaga    3240
ctgaggctca gtacgtattc ctgcatcagt gcatctgcgg ttcctccaac agtcagccca    3300
ggccccagcc gagaaggaag tcccgtatga ggatgtcgaa aacctcatct acgagaacgt    3360
ggccgccatc caggcccaca gttggaggt ctaagtgacg aggggctgg gtcggcagcc    3420 caggcatcct caagctctgg acacccactt gagcccagat cctggaagat cagagggct    3480 gggctcccag actcctgggt gctgtgggag aggggctg gtatcccaaa ctctggtttc    3540
cccaggagag agtggtctgg tgggcttcag atgagtccta tggagctggg ggatctggat    3600
tcctggttcc ctgaaggagg agagggatga tagcttggat tccctaggtc tttccaggat    3660
```

```
gcagaaagaa acaggctggg gcctggattc tgaggcagga aggaatttgg gtctggagtt    3720
ctggctactt gaggaccaaa ggcaggaagg atcctgcctt gattttactt cagaaaccaa    3780
atcagtcttc tataatctgg ggtcggaggg agtccctgtg cccaaggtct ctctgcaccc    3840
caccatccac atgtattttt ccttctatcc cataatttat taaatcactg ttctccccag    3900
```

<210> SEQ ID NO 2
<211> LENGTH: 1118
<212> TYPE: PRT
<213> ORGANISM: Homo sapiens

<400> SEQUENCE: 2

```
Met Ala Gly Ala Gly Gly Leu Gly Val Trp Gly Asn Leu Val Leu
 1               5                  10                  15

Leu Gly Leu Cys Ser Trp Thr Gly Ala Arg Ala Pro Ala Pro Asn Pro
                20                  25                  30

Gly Arg Asn Leu Thr Val Glu Thr Gln Thr Thr Ser Ser Ile Ser Leu
            35                  40                  45

Ser Trp Glu Val Pro Asp Gly Leu Asp Ser Gln Asn Ser Asn Tyr Trp
    50                  55                  60

Val Gln Cys Thr Gly Asp Gly Thr Thr Glu Thr Arg Asn Thr Thr
65                  70                  75                  80

Ala Thr Asn Val Thr Val Asp Gly Leu Gly Pro Gly Ser Leu Tyr Thr
                85                  90                  95

Cys Ser Val Trp Val Glu Lys Asp Gly Val Asn Ser Ser Val Gly Thr
            100                 105                 110

Val Thr Thr Ala Thr Ala Pro Asn Pro Val Arg Asn Leu Arg Val Glu
        115                 120                 125

Ala Gln Thr Asn Ser Ser Ile Ala Leu Thr Trp Glu Val Pro Asp Gly
    130                 135                 140

Pro Asp Pro Gln Asn Ser Thr Tyr Gly Val Glu Tyr Thr Gly Asp Gly
145                 150                 155                 160

Gly Arg Ala Gly Thr Arg Ser Thr Ala His Thr Asn Ile Thr Val Asp
                165                 170                 175

Gly Leu Glu Pro Gly Cys Leu Tyr Ala Phe Ser Met Trp Val Gly Lys
            180                 185                 190

Asn Gly Ile Asn Ser Ser Arg Glu Thr Arg Asn Ala Thr Thr Ala His
        195                 200                 205

Asn Pro Val Arg Lys Pro Glu Ser Gly Gly Ser Asp His Gln Leu His
    210                 215                 220

Leu Pro Glu Leu Gly Gly Pro Arg Trp His Arg Pro Thr Glu Leu Asp
225                 230                 235                 240

Leu Leu Arg Thr Ser Ala Leu Glu Met Val Ala Glu Gln Arg Leu Glu
                245                 250                 255

Thr Gln Gln Thr Pro Glu Ser Pro Val Asp Gly Leu Gly Pro Gly Ser
            260                 265                 270

Leu Tyr Thr Cys Ser Val Trp Val Glu Lys Asp Gly Val Asn Ser Ser
        275                 280                 285

Ser Trp Arg Leu Val Thr Ser Thr Ala Pro Asn Pro Val Arg Asn
    290                 295                 300

Leu Thr Val Glu Ala Gln Thr Asn Ser Ser Ile Ala Leu Thr Trp Glu
305                 310                 315                 320

Val Pro Asp Gly Pro Asp Pro Gln Asn Ser Thr Tyr Gly Val Glu Tyr
                325                 330                 335
```

```
Thr Gly Asp Gly Gly Arg Ala Gly Thr Arg Ser Thr Ala His Thr Asn
            340                 345                 350

Ile Thr Val Asp Arg Leu Glu Pro Gly Cys Leu Tyr Val Phe Ser Val
            355                 360                 365

Trp Val Gly Lys Asn Gly Ile Asn Ser Ser Arg Glu Thr Arg Asn Ala
            370                 375                 380

Thr Thr Ala Pro Asn Pro Val Arg Asn Leu His Met Glu Thr Gln Thr
385                 390                 395                 400

Asn Ser Ser Ile Ala Leu Cys Trp Glu Val Pro Asp Gly Pro Tyr Pro
                405                 410                 415

Gln Asp Tyr Thr Tyr Trp Val Gly Tyr Thr Gly Asp Gly Gly Gly Thr
            420                 425                 430

Glu Thr Arg Asn Thr Thr Asn Thr Ser Val Thr Ala Glu Arg Leu Glu
            435                 440                 445

Pro Gly Thr Leu Tyr Thr Phe Ser Val Trp Ala Glu Lys Asn Gly Ala
        450                 455                 460

Arg Gly Ser Arg Gln Asn Val Ser Ile Ser Thr Val Pro Asn Ala Val
465                 470                 475                 480

Thr Ser Leu Ser Lys Gln Asp Trp Thr Asn Ser Thr Ile Ala Leu Arg
                485                 490                 495

Trp Thr Ala Pro Gln Gly Pro Gly Gln Ser Ser Tyr Ser Tyr Trp Val
            500                 505                 510

Ser Trp Val Arg Glu Gly Met Thr Asp Pro Arg Thr Gln Ser Thr Ser
            515                 520                 525

Gly Thr Asp Ile Thr Leu Lys Glu Leu Glu Ala Gly Ser Leu Tyr His
        530                 535                 540

Leu Thr Val Trp Ala Glu Arg Asn Glu Val Arg Gly Tyr Asn Ser Thr
545                 550                 555                 560

Leu Thr Ala Ala Thr Ala Pro Asn Glu Val Thr Asp Leu Gln Asn Glu
                565                 570                 575

Thr Gln Thr Lys Asn Ser Val Met Leu Trp Trp Lys Ala Pro Gly Asp
            580                 585                 590

Pro His Ser Gln Leu Tyr Val Tyr Trp Val Gln Trp Ala Ser Lys Gly
        595                 600                 605

His Pro Arg Arg Gly Gln Asp Pro Gln Ala Asn Trp Val Asn Gln Thr
            610                 615                 620

Ser Arg Thr Asn Glu Thr Trp Tyr Lys Val Glu Ala Leu Glu Pro Gly
625                 630                 635                 640

Thr Leu Tyr Asn Phe Thr Val Trp Ala Glu Arg Asn Asp Val Ala Ser
                645                 650                 655

Ser Thr Gln Ser Leu Cys Ala Ser Thr Tyr Pro Asp Thr Val Thr Ile
            660                 665                 670

Thr Ser Cys Val Ser Thr Ser Ala Gly Tyr Gly Val Asn Leu Ile Trp
        675                 680                 685

Ser Cys Pro Gln Gly Gly Tyr Glu Ala Phe Glu Leu Glu Val Gly Gly
        690                 695                 700

Gln Arg Gly Ser Gln Asp Arg Ser Ser Cys Gly Glu Ala Val Ser Val
705                 710                 715                 720

Leu Gly Leu Gly Pro Ala Arg Ser Tyr Pro Ala Thr Ile Thr Thr Ile
                725                 730                 735

Trp Asp Gly Met Lys Val Val Ser His Ser Val Val Cys His Thr Glu
            740                 745                 750
```

```
Ser Ala Gly Val Ile Ala Gly Ala Phe Val Gly Ile Leu Leu Phe Leu
        755                 760                 765
Ile Leu Val Gly Leu Leu Ile Phe Phe Leu Lys Arg Arg Asn Lys Lys
        770                 775                 780
Lys Gln Gln Lys Pro Glu Leu Arg Asp Leu Val Phe Ser Ser Pro Gly
785                 790                 795                 800
Asp Ile Pro Ala Glu Asp Phe Ala Asp His Val Arg Lys Asn Glu Arg
                805                 810                 815
Asp Ser Asn Cys Gly Phe Ala Asp Glu Tyr Gln Gln Leu Ser Leu Val
                820                 825                 830
Gly His Ser Gln Ser Gln Met Val Ala Ser Ala Ser Glu Asn Asn Ala
                835                 840                 845
Lys Asn Arg Tyr Arg Asn Val Leu Pro Tyr Asp Trp Ser Arg Val Pro
        850                 855                 860
Leu Lys Pro Ile His Glu Glu Pro Gly Ser Asp Tyr Ile Asn Ala Ser
865                 870                 875                 880
Phe Met Pro Gly Leu Trp Ser Pro Gln Glu Phe Ile Ala Thr Gln Gly
                885                 890                 895
Pro Leu Pro Gln Thr Val Gly Asp Phe Trp Arg Leu Val Trp Glu Gln
                900                 905                 910
Gln Ser His Thr Leu Val Met Leu Thr Asn Cys Met Glu Ala Gly Arg
                915                 920                 925
Val Lys Cys Glu His Tyr Trp Pro Leu Asp Ser Gln Pro Cys Thr His
        930                 935                 940
Gly His Leu Arg Val Thr Leu Val Gly Glu Glu Val Met Glu Asn Trp
945                 950                 955                 960
Thr Val Arg Glu Leu Leu Leu Leu Gln Val Glu Glu Gln Lys Thr Leu
                965                 970                 975
Ser Val Arg Gln Phe His Tyr Gln Ala Trp Pro Asp His Gly Val Pro
                980                 985                 990
Ser Ser Pro Asp Thr Leu Leu Ala Phe Trp Arg Met Leu Arg Gln Trp
                995                1000                1005
Leu Asp Gln Thr Met Glu Gly Gly Pro Pro Ile Val His Cys Ser Ala
        1010                1015                1020
Gly Val Gly Arg Thr Gly Thr Leu Ile Ala Leu Asp Val Leu Leu Arg
1025                1030                1035                1040
Gln Leu Gln Ser Glu Gly Leu Leu Gly Pro Phe Ser Phe Val Arg Lys
                1045                1050                1055
Met Arg Glu Ser Arg Pro Leu Met Val Gln Thr Glu Ala Gln Tyr Val
                1060                1065                1070
Phe Leu His Gln Cys Ile Cys Gly Ser Ser Asn Ser Gln Pro Arg Pro
        1075                1080                1085
Gln Pro Arg Arg Lys Ser Arg Met Arg Met Ser Lys Thr Ser Ser Thr
        1090                1095                1100
Arg Thr Trp Pro Pro Ser Arg Pro Thr Ser Trp Arg Ser Lys
1105                1110                1115

<210> SEQ ID NO 3
<211> LENGTH: 3357
<212> TYPE: DNA
<213> ORGANISM: Homo sapiens
<220> FEATURE:
<221> NAME/KEY: CDS
<222> LOCATION: (1)...(3357)

<400> SEQUENCE: 3
```

```
atg gct ggg gct ggc ggg ggc ctc ggg gtc tgg ggg aac ctg gtg ctg      48
Met Ala Gly Ala Gly Gly Gly Leu Gly Val Trp Gly Asn Leu Val Leu
 1               5                  10                  15 ctg ggc ctg tgc agc tgg aca ggg gcc agg gcg cct gcc ccc aac cca      96
Leu Gly Leu Cys Ser Trp Thr Gly Ala Arg Ala Pro Ala Pro Asn Pro
             20                  25                  30 ggg agg aac ctg aca gtg gag act cag acc acc agc tcc atc tcc ctg     144
Gly Arg Asn Leu Thr Val Glu Thr Gln Thr Thr Ser Ser Ile Ser Leu
         35                  40                  45 agc tgg gag gtc ccc gat ggc cta gac tca cag aac tcc aac tac tgg     192
Ser Trp Glu Val Pro Asp Gly Leu Asp Ser Gln Asn Ser Asn Tyr Trp
 50                  55                  60 gtt cag tgt act gga gac ggc ggc aca aca gag act cga aac aca aca     240
Val Gln Cys Thr Gly Asp Gly Gly Thr Thr Glu Thr Arg Asn Thr Thr
 65                  70                  75                  80 gcc acc aac gtc acc gtg gat ggc ctt gga ccc ggg tca ttg tat acg     288
Ala Thr Asn Val Thr Val Asp Gly Leu Gly Pro Gly Ser Leu Tyr Thr
                 85                  90                  95 tgt tct gtg tgg gtg gag aaa gac gga gta aat agc tct gtg ggg act     336
Cys Ser Val Trp Val Glu Lys Asp Gly Val Asn Ser Ser Val Gly Thr
                100                 105                 110 gtc act act gcc aca gct ccc aac cca gtg agg aac ctg aga gtg gag     384
Val Thr Thr Ala Thr Ala Pro Asn Pro Val Arg Asn Leu Arg Val Glu
            115                 120                 125 gct cag acc aac agc tcc atc gcc ctg acc tgg gag gtc ccc gac ggc     432
Ala Gln Thr Asn Ser Ser Ile Ala Leu Thr Trp Glu Val Pro Asp Gly
        130                 135                 140 cca gac cca cag aac tcc acc tac ggg gtt gag tac act gga gat ggt     480
Pro Asp Pro Gln Asn Ser Thr Tyr Gly Val Glu Tyr Thr Gly Asp Gly
145                 150                 155                 160 ggc aga gca ggg act cga agc aca gca cac act aac atc acc gtg gat     528
Gly Arg Ala Gly Thr Arg Ser Thr Ala His Thr Asn Ile Thr Val Asp
                165                 170                 175 gga ctt gaa ccc ggg tgt ttg tat gcg ttt tcc atg tgg gtg gga aag     576
Gly Leu Glu Pro Gly Cys Leu Tyr Ala Phe Ser Met Trp Val Gly Lys
                180                 185                 190 aat gga atc aac agc tcc cgg gag act cga aat gcc acc aca gct cac     624
Asn Gly Ile Asn Ser Ser Arg Glu Thr Arg Asn Ala Thr Thr Ala His
            195                 200                 205 aac cca gtg agg aaa cct gag agt gga ggc tca gac cac cag ctc cat     672
Asn Pro Val Arg Lys Pro Glu Ser Gly Gly Ser Asp His Gln Leu His
        210                 215                 220 ctc cct gag ctg gga ggt ccc cga tgg cac aga ccc aca gaa ctc gac     720
Leu Pro Glu Leu Gly Gly Pro Arg Trp His Arg Pro Thr Glu Leu Asp
225                 230                 235                 240 cta ctg cgt acg agt gca ctg gag atg gtg gca gaa cag aga ctc gaa     768
Leu Leu Arg Thr Ser Ala Leu Glu Met Val Ala Glu Gln Arg Leu Glu
                245                 250                 255 aca caa cag aca cca gag tca cca gtg gat ggc ctt gga ccc ggg tca     816
Thr Gln Gln Thr Pro Glu Ser Pro Val Asp Gly Leu Gly Pro Gly Ser
                260                 265                 270 ttg tat acg tgt tct gtg tgg gtg gag aaa gac gga gta aat agc tcc     864
Leu Tyr Thr Cys Ser Val Trp Val Glu Lys Asp Gly Val Asn Ser Ser
            275                 280                 285 tcg tgg aga ttg gta act agt acc aca gct ccc aac cca gtg aga aac     912
Ser Trp Arg Leu Val Thr Ser Thr Thr Ala Pro Asn Pro Val Arg Asn
        290                 295                 300 ctg aca gtg gag gct cag acc aac agc tcc atc gcc ctg acc tgg gag     960
Leu Thr Val Glu Ala Gln Thr Asn Ser Ser Ile Ala Leu Thr Trp Glu
```

```
                    305                 310                 315                 320 gtc ccc gat ggc cca gac cca cag aac tcc acc tac ggg gtt gag tac              1008
Val Pro Asp Gly Pro Asp Pro Gln Asn Ser Thr Tyr Gly Val Glu Tyr
                    325                 330                 335 act gga gat ggt ggc aga gca ggg act cga agc aca gca cac acc aac              1056
Thr Gly Asp Gly Gly Arg Ala Gly Thr Arg Ser Thr Ala His Thr Asn
                340                 345                 350 atc acc gtg gat aga ctt gaa ccc ggg tgt ttg tat gtg ttt tcc gtg              1104
Ile Thr Val Asp Arg Leu Glu Pro Gly Cys Leu Tyr Val Phe Ser Val
            355                 360                 365 tgg gtg ggg aag aat gga atc aac agc tcc cgg gag act cga aat gcc              1152
Trp Val Gly Lys Asn Gly Ile Asn Ser Ser Arg Glu Thr Arg Asn Ala
        370                 375                 380 aca gcc ccc aac cca gtg aga aac ctc cat atg gag act cag acc                  1200
Thr Thr Ala Pro Asn Pro Val Arg Asn Leu His Met Glu Thr Gln Thr
385                 390                 395                 400 aac agc tcc atc gcc cta tgc tgg gaa gtc ccc gat ggc cca tac cct              1248
Asn Ser Ser Ile Ala Leu Cys Trp Glu Val Pro Asp Gly Pro Tyr Pro
                    405                 410                 415 cag gac tac acc tac tgg gta ggg tac act gga gac ggt ggt ggc aca              1296
Gln Asp Tyr Thr Tyr Trp Val Gly Tyr Thr Gly Asp Gly Gly Gly Thr
                420                 425                 430 gag acc cga aac aca aca aat acc agt gtg aca gct gag aga ctt gag              1344
Glu Thr Arg Asn Thr Thr Asn Thr Ser Val Thr Ala Glu Arg Leu Glu
            435                 440                 445 ccc gga acc ttg tac aca ttc tct gta tgg gca gaa aaa aat gga gca              1392
Pro Gly Thr Leu Tyr Thr Phe Ser Val Trp Ala Glu Lys Asn Gly Ala
        450                 455                 460 cgt ggc tcc agg cag aat gtc agc atc tcc aca gtc ccc aac gca gtg              1440
Arg Gly Ser Arg Gln Asn Val Ser Ile Ser Thr Val Pro Asn Ala Val
465                 470                 475                 480 aca agc ctc agc aag cag gac tgg acc aac agc acc att gct ttg cgc              1488
Thr Ser Leu Ser Lys Gln Asp Trp Thr Asn Ser Thr Ile Ala Leu Arg
                    485                 490                 495 tgg aca gct ccc cag ggc cca ggc cag tct tcc tac agc tac tgg gtc              1536
Trp Thr Ala Pro Gln Gly Pro Gly Gln Ser Ser Tyr Ser Tyr Trp Val
                500                 505                 510 tca tgg gtc agg gaa ggc atg act gac ccc agg acc caa agc acc tca              1584
Ser Trp Val Arg Glu Gly Met Thr Asp Pro Arg Thr Gln Ser Thr Ser
            515                 520                 525 ggt act gac atc acc cta aag gaa ctg gaa gct ggc agc ctg tac cac              1632
Gly Thr Asp Ile Thr Leu Lys Glu Leu Glu Ala Gly Ser Leu Tyr His
        530                 535                 540 ctc acc gtc tgg gcc gag agg aat gag gtc aga ggc tat aac agc acc              1680
Leu Thr Val Trp Ala Glu Arg Asn Glu Val Arg Gly Tyr Asn Ser Thr
545                 550                 555                 560 ctc act gca gcc act gct ccc aat gag gtc aca gat ctc cag aat gaa              1728
Leu Thr Ala Ala Thr Ala Pro Asn Glu Val Thr Asp Leu Gln Asn Glu
                    565                 570                 575 act cag act aag aac tca gtc atg ctg tgg tgg aag gcc cct gga gac              1776
Thr Gln Thr Lys Asn Ser Val Met Leu Trp Trp Lys Ala Pro Gly Asp
                580                 585                 590 ccc cac tct cag ttg tac gta tac tgg gtc cag tgg gcc agc aag gga              1824
Pro His Ser Gln Leu Tyr Val Tyr Trp Val Gln Trp Ala Ser Lys Gly
            595                 600                 605 cat ccc cgg agg ggg caa gat ccc caa gcg aat tgg gtc aac cag acc              1872
His Pro Arg Arg Gly Gln Asp Pro Gln Ala Asn Trp Val Asn Gln Thr
        610                 615                 620 agc agg acc aat gag acg tgg tac aaa gtg gag gcc ctg gaa ccc ggg              1920
```

```
Ser Arg Thr Asn Glu Thr Trp Tyr Lys Val Glu Ala Leu Glu Pro Gly
625                 630                 635                 640 acg ttg tac aat ttc acc gtg tgg gca gag agg aat gac gta gcc agt     1968
Thr Leu Tyr Asn Phe Thr Val Trp Ala Glu Arg Asn Asp Val Ala Ser
                    645                 650                 655 tcc acg cag agc ctc tgt gcg tcc aca tac cca gac aca gtc acc atc     2016
Ser Thr Gln Ser Leu Cys Ala Ser Thr Tyr Pro Asp Thr Val Thr Ile
            660                 665                 670 act tcc tgt gtc agc acc tca gcg ggc tat gga gtc aac ttg atc tgg     2064
Thr Ser Cys Val Ser Thr Ser Ala Gly Tyr Gly Val Asn Leu Ile Trp
        675                 680                 685 tcc tgc ccc cag gga ggc tac gag gcc ttt gag ttg gag gtg gga gga     2112
Ser Cys Pro Gln Gly Gly Tyr Glu Ala Phe Glu Leu Glu Val Gly Gly
    690                 695                 700 cag cgg ggc tcc cag gac aga tct tca tgt ggg gag gct gtg tct gtg     2160
Gln Arg Gly Ser Gln Asp Arg Ser Ser Cys Gly Glu Ala Val Ser Val
705                 710                 715                 720 ttg ggt ctc ggg ccg gct cgg tcc tac cca gcc acc atc acg acc atc     2208
Leu Gly Leu Gly Pro Ala Arg Ser Tyr Pro Ala Thr Ile Thr Thr Ile
                    725                 730                 735 tgg gac gga atg aag gtc gtg tct cac tct gtg gtc tgc cac acc gag     2256
Trp Asp Gly Met Lys Val Val Ser His Ser Val Val Cys His Thr Glu
            740                 745                 750 agt gca ggg gtc att gcc gga gcc ttt gtg ggc atc ctc ctg ttt ctc     2304
Ser Ala Gly Val Ile Ala Gly Ala Phe Val Gly Ile Leu Leu Phe Leu
        755                 760                 765 atc ctc gtg ggc ctg ctg att ttc ttc ctg aag agg agg aat aag aag     2352
Ile Leu Val Gly Leu Leu Ile Phe Phe Leu Lys Arg Arg Asn Lys Lys
    770                 775                 780 aag cag cag aaa cca gaa ctc agg gat ctg gtc ttt agc tcc cca ggg     2400
Lys Gln Gln Lys Pro Glu Leu Arg Asp Leu Val Phe Ser Ser Pro Gly
785                 790                 795                 800 gac atc cca gct gaa gac ttc gct gac cac gtc agg aag aat gag agg     2448
Asp Ile Pro Ala Glu Asp Phe Ala Asp His Val Arg Lys Asn Glu Arg
                    805                 810                 815 gac agc aac tgt ggt ttt gca gac gag tac cag caa ctc tcc ctg gtg     2496
Asp Ser Asn Cys Gly Phe Ala Asp Glu Tyr Gln Gln Leu Ser Leu Val
            820                 825                 830 ggc cac agc cag tct cag atg gtg gct tcg gct tca gag aac aac gcc     2544
Gly His Ser Gln Ser Gln Met Val Ala Ser Ala Ser Glu Asn Asn Ala
        835                 840                 845 aag aac cgc tac aga aat gtg ctg ccc tat gac tgg tcc cgg gtg ccc     2592
Lys Asn Arg Tyr Arg Asn Val Leu Pro Tyr Asp Trp Ser Arg Val Pro
    850                 855                 860 ctg aag ccc atc cat gag gag cca ggc tct gac tac atc aat gcc agc     2640
Leu Lys Pro Ile His Glu Glu Pro Gly Ser Asp Tyr Ile Asn Ala Ser
865                 870                 875                 880 ttc atg ccc ggt ctc tgg agc ccc cag gag ttc att gca acc cag ggt     2688
Phe Met Pro Gly Leu Trp Ser Pro Gln Glu Phe Ile Ala Thr Gln Gly
                    885                 890                 895 ccc ctg cca cag aca gtg ggt gac ttc tgg cgc ctg gtg tgg gaa cag     2736
Pro Leu Pro Gln Thr Val Gly Asp Phe Trp Arg Leu Val Trp Glu Gln
            900                 905                 910 cag agc cac acc ctg gtc atg ctg acc aac tgc atg gag gcc ggc cgg     2784
Gln Ser His Thr Leu Val Met Leu Thr Asn Cys Met Glu Ala Gly Arg
        915                 920                 925 gtg aag tgt gag cat tac tgg cct ctg gac tcg cag ccc tgc acc cat     2832
Val Lys Cys Glu His Tyr Trp Pro Leu Asp Ser Gln Pro Cys Thr His
    930                 935                 940
```

| | | | | | | | | | | | | |
|---|---|---|---|---|---|---|---|---|---|---|---|---|
| ggg | cac | ctg | cgg | gta | acc | ctg | gta | ggt | gag | gaa | gtg | atg | gag | aac | tgg | 2880 |
| Gly | His | Leu | Arg | Val | Thr | Leu | Val | Gly | Glu | Glu | Val | Met | Glu | Asn | Trp | |
| 945 | | | | 950 | | | | | 955 | | | | 960 | | | | acg gtg cgg gaa ctg ctc ctc cag gtg gag gag cag aag aca ctg       2928
Thr Val Arg Glu Leu Leu Leu Gln Val Glu Glu Gln Lys Thr Leu
            965                 970                 975 tct gtg cgc caa ttc cac tac cag gcc tgg ccg gat cac ggc gtt ccc   2976
Ser Val Arg Gln Phe His Tyr Gln Ala Trp Pro Asp His Gly Val Pro
        980                 985                 990 tcc tcc cca gac acc ttg ctg gct ttc tgg agg atg ctt cgg cag tgg   3024
Ser Ser Pro Asp Thr Leu Leu Ala Phe Trp Arg Met Leu Arg Gln Trp
            995                 1000                1005 ctg gat cag acc atg gag gga ggc cca ccc att gtg cac tgc agt gct   3072
Leu Asp Gln Thr Met Glu Gly Gly Pro Pro Ile Val His Cys Ser Ala
    1010                1015                1020 ggc gtg ggt cgc aca gga acc ctc att gcc ctg gac gtc ctg ctc cgg   3120
Gly Val Gly Arg Thr Gly Thr Leu Ile Ala Leu Asp Val Leu Leu Arg
1025                1030                1035                1040 cag ctg cag tcc gag ggt ctc ctt ggg ccc ttc agc ttt gta agg aag   3168
Gln Leu Gln Ser Glu Gly Leu Leu Gly Pro Phe Ser Phe Val Arg Lys
        1045                1050                1055 atg aga gag agt cgg ccg ttg atg gtg cag act gag gct cag tac gta   3216
Met Arg Glu Ser Arg Pro Leu Met Val Gln Thr Glu Ala Gln Tyr Val
    1060                1065                1070 ttc ctg cat cag tgc atc tgc ggt tcc tcc aac agt cag ccc agg ccc   3264
Phe Leu His Gln Cys Ile Cys Gly Ser Ser Asn Ser Gln Pro Arg Pro
1075                1080                1085 cag ccg aga agg aag tcc cgt atg agg atg tcg aaa acc tca tct acg   3312
Gln Pro Arg Arg Lys Ser Arg Met Arg Met Ser Lys Thr Ser Ser Thr
        1090                1095                1100 aga acg tgg ccg cca tcc agg ccc aca agt tgg agg tct aag tga       3357
Arg Thr Trp Pro Pro Ser Arg Pro Thr Ser Trp Arg Ser Lys *
1105                1110                1115

<210> SEQ ID NO 4
<211> LENGTH: 1093
<212> TYPE: PRT
<213> ORGANISM: Artificial Sequence
<220> FEATURE:
<223> OTHER INFORMATION: consensus sequence

<400> SEQUENCE: 4

Arg Ala Pro Ala Pro Asn Pro Gly Arg Asn Leu Thr Val Glu Thr Gln
1               5                   10                  15

Thr Thr Ser Ser Ile Ser Leu Ser Trp Glu Val Pro Asp Gly Leu Asp
                20                  25                  30

Ser Gln Asn Ser Asn Tyr Trp Val Gln Cys Thr Gly Asp Gly Gly Thr
            35                  40                  45

Thr Glu Thr Arg Asn Thr Thr Ala Thr Asn Val Thr Val Asp Gly Leu
        50                  55                  60

Gly Pro Gly Ser Leu Tyr Thr Cys Ser Val Trp Val Glu Lys Asp Gly
65                  70                  75                  80

Val Asn Ser Ser Val Gly Thr Val Thr Ala Thr Ala Pro Asn Pro
                85                  90                  95

Val Arg Asn Leu Arg Val Glu Ala Gln Thr Asn Ser Ser Ile Ala Leu
                100                 105                 110

Thr Trp Glu Val Pro Asp Gly Pro Asp Pro Gln Asn Ser Thr Tyr Gly
            115                 120                 125

Val Glu Tyr Thr Gly Asp Gly Gly Arg Ala Gly Thr Arg Ser Thr Ala

-continued

```
            130                 135                 140
His Thr Asn Ile Thr Val Asp Gly Leu Glu Pro Gly Cys Leu Tyr Ala
145                 150                 155                 160

Phe Ser Met Trp Val Gly Lys Asn Gly Ile Asn Ser Ser Arg Glu Thr
                165                 170                 175

Arg Asn Ala Thr Thr Ala His Asn Pro Val Arg Lys Pro Glu Ser Gly
            180                 185                 190

Gly Ser Asp His Gln Leu His Leu Pro Glu Leu Gly Gly Pro Arg Trp
            195                 200                 205

His Arg Pro Thr Glu Leu Asp Leu Leu Arg Thr Ser Ala Leu Glu Met
210                 215                 220

Val Ala Glu Gln Arg Leu Glu Thr Gln Gln Thr Pro Glu Ser Pro Val
225                 230                 235                 240

Asp Gly Leu Gly Pro Gly Ser Leu Tyr Thr Cys Ser Val Trp Val Glu
                245                 250                 255

Lys Asp Gly Val Asn Ser Ser Trp Arg Leu Val Thr Ser Thr Thr
            260                 265                 270

Ala Pro Asn Pro Val Arg Asn Leu Thr Val Glu Ala Gln Thr Asn Ser
            275                 280                 285

Ser Ile Ala Leu Thr Trp Glu Val Pro Asp Gly Pro Asp Pro Gln Asn
            290                 295                 300

Ser Thr Tyr Gly Val Glu Tyr Thr Gly Asp Gly Arg Ala Gly Thr
305                 310                 315                 320

Arg Ser Thr Ala His Thr Asn Ile Thr Val Asp Arg Leu Glu Pro Gly
                325                 330                 335

Cys Leu Tyr Val Phe Ser Val Trp Val Gly Lys Asn Gly Ile Asn Ser
            340                 345                 350

Ser Arg Glu Thr Arg Asn Ala Thr Thr Ala Pro Asn Pro Val Arg Asn
                355                 360                 365

Leu His Met Glu Thr Gln Thr Asn Ser Ser Ile Ala Leu Cys Trp Glu
            370                 375                 380

Val Pro Asp Gly Pro Tyr Pro Gln Asp Tyr Thr Tyr Trp Val Gly Tyr
385                 390                 395                 400

Thr Gly Asp Gly Gly Thr Glu Thr Arg Asn Thr Thr Asn Thr Ser
                405                 410                 415

Val Thr Ala Glu Arg Leu Glu Pro Gly Thr Leu Tyr Thr Phe Ser Val
            420                 425                 430

Trp Ala Glu Lys Asn Gly Ala Arg Gly Ser Arg Gln Asn Val Ser Ile
            435                 440                 445

Ser Thr Val Pro Asn Ala Val Thr Ser Leu Ser Lys Gln Asp Trp Thr
            450                 455                 460

Asn Ser Thr Ile Ala Leu Arg Trp Thr Ala Pro Gln Gly Pro Gly Gln
465                 470                 475                 480

Ser Ser Tyr Ser Tyr Trp Val Ser Trp Arg Glu Gly Met Thr Asp
                485                 490                 495

Pro Arg Thr Gln Ser Thr Ser Gly Thr Asp Ile Thr Leu Lys Glu Leu
                500                 505                 510

Glu Ala Gly Ser Leu Tyr His Leu Thr Val Trp Ala Glu Arg Asn Glu
            515                 520                 525

Val Arg Gly Tyr Asn Ser Thr Leu Thr Ala Ala Thr Ala Pro Asn Glu
            530                 535                 540

Val Thr Asp Leu Gln Asn Glu Thr Gln Thr Lys Asn Ser Val Met Leu
545                 550                 555                 560
```

```
Trp Trp Lys Ala Pro Gly Asp Pro His Ser Gln Leu Tyr Val Tyr Trp
            565                 570                 575

Val Gln Trp Ala Ser Lys Gly His Pro Arg Arg Gly Gln Asp Pro Gln
            580                 585                 590

Ala Asn Trp Val Asn Gln Thr Ser Arg Thr Asn Glu Thr Trp Tyr Lys
            595                 600                 605

Val Glu Ala Leu Glu Pro Gly Thr Leu Tyr Asn Phe Thr Val Trp Ala
            610                 615                 620

Glu Arg Asn Asp Val Ala Ser Ser Thr Gln Ser Leu Cys Ala Ser Thr
625                 630                 635                 640

Tyr Pro Asp Thr Val Thr Ile Thr Ser Cys Val Ser Thr Ser Ala Gly
            645                 650                 655

Tyr Gly Val Asn Leu Ile Trp Ser Cys Pro Gln Gly Gly Tyr Glu Ala
            660                 665                 670

Phe Glu Leu Glu Val Gly Gly Gln Arg Gly Ser Gln Asp Arg Ser Ser
            675                 680                 685

Cys Gly Glu Ala Val Ser Val Leu Gly Leu Gly Pro Ala Arg Ser Tyr
            690                 695                 700

Pro Ala Thr Ile Thr Thr Ile Trp Asp Gly Met Lys Val Val Ser His
705                 710                 715                 720

Ser Val Val Cys His Thr Glu Ser Ala Gly Val Ile Ala Gly Ala Phe
            725                 730                 735

Val Gly Ile Leu Leu Phe Leu Ile Leu Val Gly Leu Leu Ile Phe Phe
            740                 745                 750

Leu Lys Arg Arg Asn Lys Lys Gln Gln Lys Pro Glu Leu Arg Asp
            755                 760                 765

Leu Val Phe Ser Ser Pro Gly Asp Ile Pro Ala Glu Asp Phe Ala Asp
            770                 775                 780

His Val Arg Lys Asn Glu Arg Asp Ser Asn Cys Gly Phe Ala Asp Glu
785                 790                 795                 800

Tyr Gln Gln Leu Ser Leu Val Gly His Ser Gln Ser Gln Met Val Ala
            805                 810                 815

Ser Ala Ser Glu Asn Asn Ala Lys Asn Arg Tyr Arg Asn Val Leu Pro
            820                 825                 830

Tyr Asp Trp Ser Arg Val Pro Leu Lys Pro Ile His Glu Glu Pro Gly
            835                 840                 845

Ser Asp Tyr Ile Asn Ala Ser Phe Met Pro Gly Leu Trp Ser Pro Gln
            850                 855                 860

Glu Phe Ile Ala Thr Gln Gly Pro Leu Pro Gln Thr Val Gly Asp Phe
865                 870                 875                 880

Trp Arg Leu Val Trp Glu Gln Gln Ser His Thr Leu Val Met Leu Thr
            885                 890                 895

Asn Cys Met Glu Ala Gly Arg Val Lys Cys Glu His Tyr Trp Pro Leu
            900                 905                 910

Asp Ser Gln Pro Cys Thr His Gly His Leu Arg Val Thr Leu Val Gly
            915                 920                 925

Glu Glu Val Met Glu Asn Trp Thr Val Arg Glu Leu Leu Leu Leu Gln
            930                 935                 940

Val Glu Glu Gln Lys Thr Leu Ser Val Arg Gln Phe His Tyr Gln Ala
945                 950                 955                 960

Trp Pro Asp His Gly Val Pro Ser Ser Pro Asp Thr Leu Leu Ala Phe
            965                 970                 975
```

-continued

```
Trp Arg Met Leu Arg Gln Trp Leu Asp Gln Thr Met Glu Gly Gly Pro
            980                 985                 990

Pro Ile Val His Cys Ser Ala Gly Val Gly Arg Thr Gly Thr Leu Ile
            995                 1000                1005

Ala Leu Asp Val Leu Leu Arg Gln Leu Gln Ser Glu Gly Leu Leu Gly
        1010                1015                1020

Pro Phe Ser Phe Val Arg Lys Met Arg Glu Ser Arg Pro Leu Met Val
1025                1030                1035                1040

Gln Thr Glu Ala Gln Tyr Val Phe Leu His Gln Cys Ile Cys Gly Ser
                1045                1050                1055

Ser Asn Ser Gln Pro Arg Pro Gln Pro Arg Arg Lys Ser Arg Met Arg
                1060                1065                1070

Met Ser Lys Thr Ser Ser Thr Arg Thr Trp Pro Pro Ser Arg Pro Thr
                1075                1080                1085

Ser Trp Arg Ser Lys
            1090
```

<210> SEQ ID NO 5
<211> LENGTH: 87
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(87)
<223> OTHER INFORMATION: Xaa = Any Amino Acid

<400> SEQUENCE: 5

```
Pro Xaa Ser Ala Pro Xaa Thr Asn Leu Thr Val Thr Asp Val Thr Ser
1               5                   10                  15

Thr Ser Leu Thr Leu Ser Trp Ser Pro Pro Thr Xaa Gly Asn Gly Pro
            20                  25                  30

Ile Thr Gly Tyr Glu Val Thr Tyr Arg Gln Pro Lys Asn Gly Gly Glu
        35                  40                  45

Trp Asn Glu Leu Thr Val Pro Gly Thr Thr Thr Ser Tyr Thr Leu Thr
    50                  55                  60

Gly Leu Lys Pro Gly Thr Glu Tyr Glu Val Arg Val Gln Ala Val Asn
65                  70                  75                  80

Gly Gly Gly Gly Pro Glu Ser
                85
```

<210> SEQ ID NO 6
<211> LENGTH: 264
<212> TYPE: PRT
<213> ORGANISM: Artificial Sequence
<220> FEATURE:
<223> OTHER INFORMATION: consensus sequence

<400> SEQUENCE: 6

```
Asn Lys Lys Asn Arg Tyr Lys Asp Ile Leu Pro Tyr Asp His Ser
1               5                   10                  15

Arg Val Lys Leu Thr Pro Ile Asp Gly Glu Gly Ser Asp Tyr Ile
            20                  25                  30

Asn Ala Ser Tyr Ile Lys Tyr Ile Asp Gly Tyr Lys Gln Lys Lys Ala
        35                  40                  45

Ser Tyr Ile Ala Thr Gln Gly Pro Leu Pro Ser Asn Thr Val Glu Asp
    50                  55                  60

Phe Trp Arg Met Val Trp Glu Asn Gln Asn Ser Ala Ile Ile Val Met
```

```
                65                  70                  75                  80
Leu Thr Arg Leu Val Glu Arg Gly Arg Glu Lys Cys Asp Gln Tyr Trp
                    85                  90                  95
Pro Asp Glu Gly Glu Gly Glu Asn Asp Ser Glu Thr Tyr Gly Asp Ile
                100                 105                 110
Ser Val Thr Leu Lys Ser Glu Val Val Leu Glu Asp Tyr Thr Val
                115                 120                 125
Arg Thr Leu Glu Leu Thr Asn Thr Gly Ala Gly Gly Gln Asp Lys
            130                 135                 140
Glu Arg Asp Glu Thr Arg Glu Val Thr Gln Phe His Tyr Thr Gly Trp
145                 150                 155                 160
Pro Asp His Arg Gly Val Pro Glu Ser Pro Lys Ser Leu Leu Lys Phe
                165                 170                 175
Ile Arg Gln Val Arg Lys Ser Gln Glu Gln Ser Gly Pro Ser Ala Gly
                180                 185                 190
Ala Ser Asp Gly Pro Ile Val Val His Cys Ser Ala Gly Val Gly Arg
                195                 200                 205
Thr Gly Thr Phe Ile Ala Leu Asp Ile Met Leu Glu Gln Leu Glu Ala
            210                 215                 220
Glu Gly Pro Pro Ser Asp Val Val Asp Val Phe Gln Thr Val Lys Ser
225                 230                 235                 240
Leu Arg Ser Gln Arg Pro Gly Met Val Gln Thr Glu Gln Tyr Val
                245                 250                 255
Phe Ile Tyr Asp Ala Ile Leu Glu
            260

<210> SEQ ID NO 7
<211> LENGTH: 217
<212> TYPE: PRT
<213> ORGANISM: Artificial Sequence
<220> FEATURE:
<223> OTHER INFORMATION: consensus sequence

<400> SEQUENCE: 7

Gly Ser Leu Tyr His Leu Thr Val Trp Ala Glu Arg Asn Glu Val Arg
 1               5                   10                  15
Gly Tyr Asn Ser Thr Leu Thr Ala Ala Thr Ala Pro Asn Glu Val Thr
                20                  25                  30
Asp Leu Gln Asn Glu Thr Gln Thr Lys Asn Ser Val Met Leu Trp Trp
            35                  40                  45
Lys Ala Pro Gly Asp Pro His Ser Gln Leu Tyr Val Tyr Trp Val Gln
        50                  55                  60
Trp Ala Ser Lys Gly His Pro Arg Arg Gly Gln Asp Pro Gln Ala Asn
65                  70                  75                  80
Trp Val Asn Gln Thr Ser Arg Thr Asn Glu Thr Trp Tyr Lys Val Glu
                85                  90                  95
Ala Leu Glu Pro Gly Thr Leu Tyr Asn Phe Thr Val Trp Ala Glu Arg
                100                 105                 110
Asn Asp Val Ala Ser Ser Thr Gln Ser Leu Cys Ala Ser Thr Tyr Pro
            115                 120                 125
Asp Thr Val Thr Ile Thr Ser Cys Val Ser Thr Ser Ala Gly Tyr Gly
            130                 135                 140
Val Asn Leu Ile Trp Ser Cys Pro Gln Gly Tyr Glu Ala Phe Glu
145                 150                 155                 160
Leu Glu Val Gly Gly Gln Arg Gly Ser Gln Asp Arg Ser Ser Cys Gly
```

-continued

```
                165                 170                 175
Glu Ala Val Ser Val Leu Gly Leu Gly Pro Ala Arg Ser Tyr Pro Ala
            180                 185                 190

Thr Ile Thr Thr Ile Trp Asp Gly Met Lys Val Val Ser His Ser Val
            195                 200                 205

Val Cys His Thr Glu Ser Ala Gly Val
            210                 215

<210> SEQ ID NO 8
<211> LENGTH: 1118
<212> TYPE: PRT
<213> ORGANISM: Homo sapiens

<400> SEQUENCE: 8

Met Ala Gly Ala Gly Gly Leu Gly Val Trp Gly Asn Leu Val Leu
 1               5                  10                  15

Leu Gly Leu Cys Ser Trp Thr Gly Ala Arg Ala Pro Ala Pro Asn Pro
            20                  25                  30

Gly Arg Asn Leu Thr Val Glu Thr Gln Thr Thr Ser Ser Ile Ser Leu
            35                  40                  45

Ser Trp Glu Val Pro Asp Gly Leu Asp Ser Gln Asn Ser Asn Tyr Trp
        50                  55                  60

Val Gln Cys Thr Gly Asp Gly Thr Thr Glu Thr Arg Asn Thr Thr
 65                 70                  75                  80

Ala Thr Asn Val Thr Val Asp Gly Leu Gly Pro Gly Ser Leu Tyr Thr
                85                  90                  95

Cys Ser Val Trp Val Glu Lys Asp Gly Val Asn Ser Ser Val Gly Thr
            100                 105                 110

Val Thr Thr Ala Thr Ala Pro Asn Pro Val Arg Asn Leu Arg Val Glu
        115                 120                 125

Ala Gln Thr Asn Ser Ser Ile Ala Leu Thr Trp Glu Val Pro Asp Gly
    130                 135                 140

Pro Asp Pro Gln Asn Ser Thr Tyr Gly Val Glu Tyr Thr Gly Asp Gly
145                 150                 155                 160

Gly Arg Ala Gly Thr Arg Ser Thr Ala His Thr Asn Ile Thr Val Asp
                165                 170                 175

Gly Leu Glu Pro Gly Cys Leu Tyr Ala Phe Ser Met Trp Val Gly Lys
            180                 185                 190

Asn Gly Ile Asn Ser Ser Arg Glu Thr Arg Asn Ala Thr Thr Ala His
        195                 200                 205

Asn Pro Val Arg Lys Pro Glu Ser Gly Gly Ser Asp His Gln Leu His
    210                 215                 220

Leu Pro Glu Leu Gly Gly Pro Arg Trp His Arg Pro Thr Glu Leu Asp
225                 230                 235                 240

Leu Leu Arg Thr Ser Ala Leu Glu Met Val Ala Glu Gln Arg Leu Glu
                245                 250                 255

Thr Gln Gln Thr Pro Glu Ser Pro Val Asp Gly Leu Gly Pro Gly Ser
            260                 265                 270

Leu Tyr Thr Cys Ser Val Trp Val Glu Lys Asp Gly Val Asn Ser Ser
        275                 280                 285

Ser Trp Arg Leu Val Thr Ser Thr Ala Pro Asn Pro Val Arg Asn
    290                 295                 300

Leu Thr Val Glu Ala Gln Thr Asn Ser Ser Ile Ala Leu Thr Trp Glu
305                 310                 315                 320
```

```
Val Pro Asp Gly Pro Asp Pro Gln Asn Ser Thr Tyr Gly Val Glu Tyr
            325                 330                 335

Thr Gly Asp Gly Gly Arg Ala Gly Thr Arg Ser Thr Ala His Thr Asn
            340                 345                 350

Ile Thr Val Asp Arg Leu Glu Pro Gly Cys Leu Tyr Val Phe Ser Val
            355                 360                 365

Trp Val Gly Lys Asn Gly Ile Asn Ser Ser Arg Glu Thr Arg Asn Ala
            370                 375                 380

Thr Thr Ala Pro Asn Pro Val Arg Asn Leu His Met Glu Thr Gln Thr
385                 390                 395                 400

Asn Ser Ser Ile Ala Leu Cys Trp Glu Val Pro Asp Gly Pro Tyr Pro
                405                 410                 415

Gln Asp Tyr Thr Tyr Trp Val Gly Tyr Thr Gly Asp Gly Gly Gly Thr
            420                 425                 430

Glu Thr Arg Asn Thr Thr Asn Thr Ser Val Thr Ala Glu Arg Leu Glu
            435                 440                 445

Pro Gly Thr Leu Tyr Thr Phe Ser Val Trp Ala Glu Lys Asn Gly Ala
            450                 455                 460

Arg Gly Ser Arg Gln Asn Val Ser Ile Ser Thr Val Pro Asn Ala Val
465                 470                 475                 480

Thr Ser Leu Ser Lys Gln Asp Trp Thr Asn Ser Thr Ile Ala Leu Arg
                485                 490                 495

Trp Thr Ala Pro Gln Gly Pro Gly Gln Ser Ser Tyr Ser Tyr Trp Val
            500                 505                 510

Ser Trp Val Arg Glu Gly Met Thr Asp Pro Arg Thr Gln Ser Thr Ser
            515                 520                 525

Gly Thr Asp Ile Thr Leu Lys Glu Leu Glu Ala Gly Ser Leu Tyr His
530                 535                 540

Leu Thr Val Trp Ala Glu Arg Asn Glu Val Arg Gly Tyr Asn Ser Thr
545                 550                 555                 560

Leu Thr Ala Ala Thr Ala Pro Asn Glu Val Thr Asp Leu Gln Asn Glu
                565                 570                 575

Thr Gln Thr Lys Asn Ser Val Met Leu Trp Trp Lys Ala Pro Gly Asp
            580                 585                 590

Pro His Ser Gln Leu Tyr Val Tyr Trp Val Gln Trp Ala Ser Lys Gly
            595                 600                 605

His Pro Arg Arg Gly Gln Asp Pro Gln Ala Asn Trp Val Asn Gln Thr
            610                 615                 620

Ser Arg Thr Asn Glu Thr Trp Tyr Lys Val Glu Ala Leu Glu Pro Gly
625                 630                 635                 640

Thr Leu Tyr Asn Phe Thr Val Trp Ala Glu Arg Asn Asp Val Ala Ser
                645                 650                 655

Ser Thr Gln Ser Leu Cys Ala Ser Thr Tyr Pro Asp Thr Val Thr Ile
                660                 665                 670

Thr Ser Cys Val Ser Thr Ser Ala Gly Tyr Gly Val Asn Leu Ile Trp
            675                 680                 685

Ser Cys Pro Gln Gly Gly Tyr Glu Ala Phe Glu Leu Glu Val Gly Gly
            690                 695                 700

Gln Arg Gly Ser Gln Asp Arg Ser Ser Cys Gly Glu Ala Val Ser Val
705                 710                 715                 720

Leu Gly Leu Gly Pro Ala Arg Ser Tyr Pro Ala Thr Ile Thr Thr Ile
                725                 730                 735

Trp Asp Gly Met Lys Val Val Ser His Ser Val Val Cys His Thr Glu
```

```
                    740                 745                 750
Ser Ala Gly Val Ile Ala Gly Ala Phe Val Gly Ile Leu Leu Phe Leu
                755                 760                 765
Ile Leu Val Gly Leu Leu Ile Phe Phe Leu Lys Arg Arg Asn Lys Lys
            770                 775                 780
Lys Gln Gln Lys Pro Glu Leu Arg Asp Leu Val Phe Ser Ser Pro Gly
785                 790                 795                 800
Asp Ile Pro Ala Glu Asp Phe Ala Asp His Val Arg Lys Asn Glu Arg
                805                 810                 815
Asp Ser Asn Cys Gly Phe Ala Asp Glu Tyr Gln Gln Leu Ser Leu Val
            820                 825                 830
Gly His Ser Gln Ser Gln Met Val Ala Ser Ala Ser Glu Asn Asn Ala
                835                 840                 845
Lys Asn Arg Tyr Arg Asn Val Leu Pro Tyr Asp Trp Ser Arg Val Pro
            850                 855                 860
Leu Lys Pro Ile His Glu Glu Pro Gly Ser Asp Tyr Ile Asn Ala Ser
865                 870                 875                 880
Phe Met Pro Gly Leu Trp Ser Pro Gln Glu Phe Ile Ala Thr Gln Gly
                885                 890                 895
Pro Leu Pro Gln Thr Val Gly Asp Phe Trp Arg Leu Val Trp Glu Gln
                900                 905                 910
Gln Ser His Thr Leu Val Met Leu Thr Asn Cys Met Glu Ala Gly Arg
            915                 920                 925
Val Lys Cys Glu His Tyr Trp Pro Leu Asp Ser Gln Pro Cys Thr His
            930                 935                 940
Gly His Leu Arg Val Thr Leu Val Gly Glu Glu Val Met Glu Asn Trp
945                 950                 955                 960
Thr Val Arg Glu Leu Leu Leu Gln Val Glu Glu Lys Thr Leu
                965                 970                 975
Ser Val Arg Gln Phe His Tyr Gln Ala Trp Pro Asp His Gly Val Pro
                980                 985                 990
Ser Ser Pro Asp Thr Leu Leu Ala Phe Trp Arg Met Leu Arg Gln Trp
            995                 1000                1005
Leu Asp Gln Thr Met Glu Gly Gly Pro Pro Ile Val His Cys Ser Ala
    1010                1015                1020
Gly Val Gly Arg Thr Gly Thr Leu Ile Ala Leu Asp Val Leu Leu Arg
1025                1030                1035                1040
Gln Leu Gln Ser Glu Gly Leu Leu Gly Pro Phe Ser Phe Val Arg Lys
                1045                1050                1055
Met Arg Glu Ser Arg Pro Leu Met Val Gln Thr Glu Ala Gln Tyr Val
                1060                1065                1070
Phe Leu His Gln Cys Ile Cys Gly Ser Ser Asn Ser Gln Pro Arg Pro
        1075                1080                1085
Gln Pro Arg Arg Lys Ser Arg Met Arg Met Ser Lys Thr Ser Ser Thr
        1090                1095                1100
Arg Thr Trp Pro Pro Ser Arg Pro Thr Ser Trp Arg Ser Lys
1105                1110                1115

<210> SEQ ID NO 9
<211> LENGTH: 8
<212> TYPE: PRT
<213> ORGANISM: Artificial Sequence
<220> FEATURE:
<223> OTHER INFORMATION: amino acids 2-9 of Prosite tyrosine specific
      protein phosphatase active site signature sequence
```

```
        PS00383
<220> FEATURE:
<221> NAME/KEY: VARIANT
<222> LOCATION: 3, 4, 6, 7, 8
<223> OTHER INFORMATION: Xaa = Any Amino Acid

<400> SEQUENCE: 9

His Cys Xaa Xaa Gly Xaa Xaa Xaa
  1               5

<210> SEQ ID NO 10
<211> LENGTH: 84
<212> TYPE: PRT
<213> ORGANISM: Artificial Sequence
<220> FEATURE:
<223> OTHER INFORMATION: Pfam protein-tyrosine  consensus amino acid
      sequence

<400> SEQUENCE: 10

Pro Ser Ala Pro Thr Asn Leu Thr Val Thr Asp Val Thr Ser Thr Ser
  1               5                  10                  15

Leu Thr Leu Ser Trp Ser Pro Pro Thr Gly Asn Gly Pro Ile Thr Gly
             20                  25                  30

Tyr Glu Val Thr Tyr Arg Gln Pro Lys Asn Gly Gly Glu Trp Asn Glu
         35                  40                  45

Leu Thr Val Pro Gly Thr Thr Ser Tyr Thr Leu Thr Gly Leu Lys
     50                  55                  60

Pro Gly Thr Glu Tyr Glu Val Arg Val Gln Ala Val Asn Gly Gly Gly
 65                  70                  75                  80

Gly Pro Glu Ser

<210> SEQ ID NO 11
<211> LENGTH: 207
<212> TYPE: PRT
<213> ORGANISM: Artificial Sequence
<220> FEATURE:
<223> OTHER INFORMATION: PD312226 consensus sequence

<400> SEQUENCE: 11

Gly Ser Leu Tyr His Leu Thr Val Trp Ala Glu Arg Asn Glu Val Arg
  1               5                  10                  15

Gly Tyr Asn Ser Thr Leu Thr Ala Ala Thr Ala Pro Asn Glu Val Thr
             20                  25                  30

Asp Leu Gln Asn Glu Thr Gln Thr Lys Asn Ser Val Met Leu Trp Trp
         35                  40                  45

Lys Ala Pro Gly Asp Pro His Ser Gln Leu Tyr Val Tyr Trp Val Gln
     50                  55                  60

Trp Ala Ser Lys Gly His Pro Arg Arg Gly Gln Asp Pro Gln Ala Asn
 65                  70                  75                  80

Trp Val Asn Gln Thr Ser Arg Thr Asn Glu Thr Trp Tyr Lys Val Glu
                 85                  90                  95

Ala Leu Glu Pro Gly Thr Leu Tyr Asn Phe Thr Val Trp Ala Glu Arg
            100                 105                 110

Asn Asp Val Ala Ser Ser Thr Gln Ser Leu Cys Ala Ser Thr Tyr Pro
        115                 120                 125

Asp Thr Val Thr Ile Thr Ser Cys Val Ser Thr Ala Gly Tyr Gly
    130                 135                 140

Val Asn Leu Ile Trp Ser Cys Pro Gln Gly Gly Tyr Glu Ala Phe Glu
145                 150                 155                 160
```

```
                                 -continued
Leu Glu Val Gly Gly Gln Arg Gly Ser Gln Asp Arg Ser Ser Cys Gly
                165             170             175

Glu Ala Val Ser Val Leu Gly Leu Gly Pro Ala Arg Ser Tyr Pro Ala
                180             185             190

Thr Ile Thr Thr Ile Trp Asp Gly Met Lys Val Val Ser His Ser
            195             200             205
```